US008454960B2

(12) United States Patent
Barbas, III

(10) Patent No.: US 8,454,960 B2
(45) Date of Patent: Jun. 4, 2013

(54) MULTISPECIFIC ANTIBODY TARGETING AND MULTIVALENCY THROUGH MODULAR RECOGNITION DOMAINS

(75) Inventor: Carlos F. Barbas, III, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/135,754

(22) Filed: Jul. 14, 2011

(65) Prior Publication Data

US 2012/0020966 A1    Jan. 26, 2012

Related U.S. Application Data

(63) Continuation-in-part of application No. 12/747,883, filed as application No. PCT/US2008/088337 on Dec. 24, 2008, now abandoned.

(60) Provisional application No. 61/364,766, filed on Jul. 15, 2010, provisional application No. 61/018,816, filed on Jan. 3, 2008, provisional application No. 61/022,767, filed on Jan. 22, 2008.

(51) Int. Cl.
*C07K 16/28* (2006.01)
*C07K 16/30* (2006.01)
*C07K 14/00* (2006.01)
*A61K 38/16* (2006.01)
*A61K 39/395* (2006.01)

(52) U.S. Cl.
USPC ............... 424/134.1; 424/143.1; 424/155.1; 424/185.1; 424/193.1; 530/387.3

(58) Field of Classification Search
None
See application file for complete search history.

(56) References Cited

U.S. PATENT DOCUMENTS

| | | | |
|---|---|---|---|
| 5,196,193 A | 3/1993 | Carroll | |
| 5,637,481 A | 6/1997 | Ledbetter et al. | |
| 5,677,171 A | 10/1997 | Hudziak et al. | |
| 5,720,954 A | 2/1998 | Hudziak et al. | |
| 5,725,856 A | 3/1998 | Hudziak et al. | |
| 5,770,195 A | 6/1998 | Hudziak et al. | |
| 5,772,997 A | 6/1998 | Hudziak et al. | |
| 5,821,337 A * | 10/1998 | Carter et al. | 530/387.3 |
| 5,844,094 A | 12/1998 | Hudson et al. | |
| 5,877,289 A | 3/1999 | Thorpe et al. | |
| 5,977,322 A | 11/1999 | Marks et al. | |
| 6,054,561 A | 4/2000 | Ring | |
| 6,103,889 A | 8/2000 | Whitlow et al. | |
| 6,132,992 A | 10/2000 | Ledbetter et al. | |
| 6,165,464 A | 12/2000 | Hudziak et al. | |
| 6,166,185 A | 12/2000 | Davis et al. | |
| 6,194,177 B1 | 2/2001 | Campbell et al. | |
| 6,235,883 B1 * | 5/2001 | Jakobovits et al. | 530/388.22 |
| 6,267,958 B1 | 7/2001 | Andya et al. | |
| 6,268,488 B1 * | 7/2001 | Barbas, III et al. | 536/6.4 |
| 6,339,142 B1 | 1/2002 | Basey et al. | |
| 6,387,371 B1 | 5/2002 | Hudziak et al. | |
| 6,399,063 B1 | 6/2002 | Hudziak et al. | |
| 6,413,932 B1 | 7/2002 | Cerretti et al. | |
| 6,417,168 B1 | 7/2002 | Greene et al. | |
| 6,458,356 B1 | 10/2002 | Arakawa et al. | |
| 6,512,096 B2 | 1/2003 | Weiner et al. | |
| 6,515,110 B1 | 2/2003 | Whitlow et al. | |
| 6,521,424 B2 | 2/2003 | Cerretti et al. | |
| 6,627,196 B1 | 9/2003 | Baughman et al. | |
| 6,719,971 B1 | 4/2004 | Carter et al. | |
| 6,800,738 B1 | 10/2004 | Carter et al. | |
| 6,821,515 B1 | 11/2004 | Cleland et al. | |
| 6,884,879 B1 * | 4/2005 | Baca et al. | 536/23.53 |
| 7,063,840 B2 | 6/2006 | Davis et al. | |
| 7,067,475 B2 | 6/2006 | Cerretti et al. | |
| 7,074,404 B2 | 7/2006 | Basey et al. | |
| 7,101,580 B2 * | 9/2006 | Metzger | 426/253 |
| 7,112,317 B2 | 9/2006 | Thorpe et al. | |
| 7,125,541 B2 | 10/2006 | Thorpe et al. | |
| 7,138,370 B2 * | 11/2006 | Oliner et al. | 514/1.1 |
| 7,148,321 B2 * | 12/2006 | Gillies et al. | 530/300 |
| 7,183,076 B2 | 2/2007 | Arathoon et al. | |
| 7,205,275 B2 | 4/2007 | Oliner et al. | |
| 7,211,252 B2 | 5/2007 | Mundy et al. | |
| 7,226,592 B2 | 6/2007 | Kreysch | |
| 7,365,054 B2 | 4/2008 | Lode et al. | |
| 7,371,379 B2 | 5/2008 | Baughman et al. | |
| 7,449,184 B2 | 11/2008 | Allison et al. | |
| 7,456,016 B2 | 11/2008 | Young et al. | |
| 7,462,352 B2 | 12/2008 | Hansen et al. | |
| 7,485,302 B2 | 2/2009 | Adams et al. | |
| 7,521,053 B2 | 4/2009 | Oliner | |
| 7,537,931 B2 | 5/2009 | Adams et al. | |
| 7,541,440 B2 | 6/2009 | Goldenberg et al. | |
| 7,612,181 B2 | 11/2009 | Wu et al. | |
| 7,625,558 B2 | 12/2009 | Greene et al. | |
| 7,638,124 B2 | 12/2009 | Reiter et al. | |
| 7,645,861 B2 | 1/2010 | Gegg et al. | |
| 7,655,764 B2 | 2/2010 | Gegg et al. | |
| 7,655,765 B2 | 2/2010 | Gegg et al. | |
| 7,662,931 B2 | 2/2010 | Gegg et al. | |
| 7,666,832 B2 | 2/2010 | Oliner et al. | |

(Continued)

FOREIGN PATENT DOCUMENTS

EP    1 591 527 A1    11/2005
EP    1 600 459 A2    11/2005

(Continued)

OTHER PUBLICATIONS

Dela Cruz et al, J Immunology 165: 5112-5121, 2000.*

(Continued)

*Primary Examiner* — Phuong Huynh
(74) *Attorney, Agent, or Firm* — Hugh Wang; Thomas Fitting; Kenley Hoover

(57) ABSTRACT

Antibodies containing one or more modular recognition domains (MRDs) that can be used to target the antibodies to specific sites are described. The use of antibodies containing one or more modular recognition domains to treat disease, and methods of making antibodies containing one or more modular recognition domains are also described.

32 Claims, 15 Drawing Sheets

U.S. PATENT DOCUMENTS

| | | | |
|---|---|---|---|
| 7,666,839 B2 | 2/2010 | Oliner et al. | |
| 7,682,609 B2 | 3/2010 | Andya et al. | |
| 7,723,499 B2 | 5/2010 | Oliner et al. | |
| 7,736,652 B2* | 6/2010 | Penichet et al. | 424/178.1 |
| 7,749,501 B2 | 7/2010 | Gelfand | |
| 7,750,127 B2 | 7/2010 | Gegg et al. | |
| 7,750,128 B2 | 7/2010 | Gegg et al. | |
| 7,786,267 B2 | 8/2010 | Zurawski et al. | |
| 7,790,674 B2 | 9/2010 | Oliner et al. | |
| 7,862,817 B2 | 1/2011 | Adams et al. | |
| 7,951,369 B2 | 5/2011 | Goldenberg et al. | |
| 7,973,140 B2 | 7/2011 | Green et al. | |
| 7,981,418 B2 | 7/2011 | Amler et al. | |
| 7,993,834 B2 | 8/2011 | Mass | |
| 8,008,453 B2 | 8/2011 | Gegg et al. | |
| 2003/0130496 A1 | 7/2003 | Winter et al. | |
| 2003/0229023 A1 | 12/2003 | Oliner et al. | |
| 2004/0001827 A1 | 1/2004 | Dennis | |
| 2004/0052785 A1 | 3/2004 | Goodman et al. | |
| 2004/0057969 A1 | 3/2004 | Smith et al. | |
| 2005/0136044 A1 | 6/2005 | Watkins et al. | |
| 2005/0287153 A1 | 12/2005 | Dennis | |
| 2006/0106203 A1 | 5/2006 | Winter et al. | |
| 2006/0128944 A1 | 6/2006 | Botti et al. | |
| 2006/0140936 A1 | 6/2006 | Goldenberg et al. | |
| 2006/0222653 A1 | 10/2006 | Abel et al. | |
| 2006/0269540 A1 | 11/2006 | Robert et al. | |
| 2007/0031402 A1 | 2/2007 | Zhang et al. | |
| 2007/0086998 A1 | 4/2007 | Nagy | |
| 2007/0166753 A1 | 7/2007 | Mass | |
| 2007/0196274 A1 | 8/2007 | Sun | |
| 2007/0202041 A1 | 8/2007 | Young et al. | |
| 2007/0248994 A1 | 10/2007 | Su | |
| 2007/0254316 A1 | 11/2007 | Rodriguez et al. | |
| 2008/0233130 A1 | 9/2008 | Tomlinson et al. | |
| 2008/0241145 A1 | 10/2008 | Goldenberg et al. | |
| 2008/0299120 A1 | 12/2008 | Miller et al. | |
| 2009/0054323 A1 | 2/2009 | Oliner et al. | |
| 2009/0087432 A1 | 4/2009 | Sliwkowski | |
| 2009/0148905 A1 | 6/2009 | Ashman et al. | |
| 2009/0181022 A1 | 7/2009 | Nielsen et al. | |
| 2009/0191212 A1 | 7/2009 | Oliner et al. | |
| 2009/0226447 A1 | 9/2009 | Boone et al. | |
| 2009/0246206 A1 | 10/2009 | Nielsen et al. | |
| 2009/0298195 A1 | 12/2009 | Rüker et al. | |
| 2009/0304694 A1 | 12/2009 | Oliner et al. | |
| 2010/0016556 A1 | 1/2010 | Carter et al. | |
| 2010/0021379 A1 | 1/2010 | Lam et al. | |
| 2010/0021473 A1 | 1/2010 | De Angelis et al. | |
| 2010/0047239 A1 | 2/2010 | Wu et al. | |
| 2010/0048877 A1 | 2/2010 | Ruker et al. | |
| 2010/0104588 A1 | 4/2010 | Dennis | |
| 2010/0111967 A1 | 5/2010 | Baehner et al. | |
| 2010/0158926 A1 | 6/2010 | Cartilage et al. | |
| 2010/0159587 A1 | 6/2010 | Brinkmann et al. | |
| 2010/0166695 A1 | 7/2010 | Bundle et al. | |
| 2010/0166746 A1 | 7/2010 | Chowdhury et al. | |
| 2010/0178298 A1 | 7/2010 | Lindhofer | |
| 2010/0233173 A1 | 9/2010 | Wu et al. | |
| 2010/0286060 A1 | 11/2010 | Oliner et al. | |
| 2010/0297103 A1 | 11/2010 | Murakami | |
| 2010/0322934 A1 | 12/2010 | Imhof-Jung et al. | |
| 2010/0330115 A1 | 12/2010 | Zurawski et al. | |
| 2011/0020332 A1 | 1/2011 | Greene et al. | |
| 2011/0027286 A1 | 2/2011 | Thurston et al. | |
| 2011/0044998 A1 | 2/2011 | Bedian et al. | |
| 2011/0046355 A1 | 2/2011 | Himmler et al. | |
| 2011/0076723 A1 | 3/2011 | Min et al. | |
| 2011/0097300 A1 | 4/2011 | Van Slyke et al. | |
| 2011/0097321 A1 | 4/2011 | Blakey et al. | |
| 2011/0110851 A1 | 5/2011 | Chang et al. | |
| 2011/0129464 A1 | 6/2011 | Adams et al. | |
| 2011/0150895 A1 | 6/2011 | Ryu et al. | |
| 2011/0158978 A1 | 6/2011 | Kirchner et al. | |
| 2011/0189206 A1 | 8/2011 | Barbas, III | |
| 2012/0020967 A1* | 1/2012 | Barbas, III | 424/134.1 |
| 2012/0034211 A1* | 2/2012 | Barbas, III | 424/133.1 |
| 2012/0057114 A1* | 3/2012 | Chen et al. | 349/123 |
| 2012/0058114 A1 | 3/2012 | Barbas, III | |

FOREIGN PATENT DOCUMENTS

| | | |
|---|---|---|
| EP | 1 517 921 B1 | 6/2006 |
| EP | 1 752 471 B9 | 11/2008 |
| EP | 2 070 944 A1 | 6/2009 |
| EP | 1 189 641 B1 | 7/2009 |
| EP | 1 210 115 B1 | 8/2009 |
| EP | 1 434 791 B1 | 10/2009 |
| EP | 2 110 138 A1 | 10/2009 |
| EP | 2 116 262 A2 | 11/2009 |
| EP | 2 272 869 A2 | 1/2011 |
| EP | 2 275 119 A1 | 1/2011 |
| EP | 2 284 194 A1 | 2/2011 |
| EP | 2 311 849 A1 | 4/2011 |
| EP | 2 316 845 A1 | 5/2011 |
| EP | 2 336 180 A1 | 6/2011 |
| EP | P50112 | 10/2012 |
| WO | WO 95/24220 A1 | 9/1995 |
| WO | WO 96/11269 A2 | 4/1996 |
| WO | WO 97/20858 | 6/1997 |
| WO | WO 98/50431 A2 | 11/1998 |
| WO | WO 01/81377 A2 | 11/2001 |
| WO | WO 03/016330 A2 | 2/2003 |
| WO | WO 03/027246 | 4/2003 |
| WO | WO 2004/032857 A2 | 4/2004 |
| WO | WO 2004/032961 A1 | 4/2004 |
| WO | WO 2004/092215 | 10/2004 |
| WO | WO 2005/023859 A1 | 3/2005 |
| WO | WO 2005/070966 A2 | 8/2005 |
| WO | WO 2005/117973 A2 | 12/2005 |
| WO | WO 2006/063150 A2 | 6/2006 |
| WO | WO 2006/078307 A1 | 7/2006 |
| WO | WO 2006/091209 A2 | 8/2006 |
| WO | WO 2007/001457 A2 | 1/2007 |
| WO | WO 2007/016185 A2 | 2/2007 |
| WO | WO 2007/019232 A2 | 2/2007 |
| WO | WO 2007/024715 A2 | 3/2007 |
| WO | WO 2007/060192 A1 | 5/2007 |
| WO | WO 2007/066109 A1 | 6/2007 |
| WO | WO 2007/068895 A1 | 6/2007 |
| WO | WO 2007/075270 A2 | 7/2007 |
| WO | WO 2007/136892 A2 | 11/2007 |
| WO | WO 2008/003103 A2 | 1/2008 |
| WO | WO 2008/019290 A2 | 2/2008 |
| WO | WO 2008/088658 A2 | 7/2008 |
| WO | WO 2008/116293 A1 | 10/2008 |
| WO | WO 2008/132568 A2 | 11/2008 |
| WO | WO 2008/144029 A1 | 11/2008 |
| WO | WO 2009/097325 A1 | 8/2009 |
| WO | WO 2009/105269 A1 | 8/2009 |
| WO | WO 2009/132876 A1 | 11/2009 |
| WO | WO 2009/158432 A2 | 12/2009 |
| WO | WO 2010/010551 A2 | 1/2010 |
| WO | WO 2010/040508 A1 | 4/2010 |
| WO | WO 2010/066836 A2 | 6/2010 |
| WO | WO 2010/108153 A2 | 9/2010 |
| WO | WO 2011/014469 A1 | 2/2011 |
| WO | WO 2012/009705 A1 | 1/2012 |

OTHER PUBLICATIONS

Helguera et al, Vaccine 24: 304-316, 2006.*
Colman et al., In Research in Immunology 145(1):33-36, 1994.*
Dufner et al., Trends Biotechnol24(11 ): 523-529, 2006.*
Ruoslahti, Erkki, "Integrins," *J. Clin. Invest.* 87:1-5, The American Society for Clinical Investigation, Inc., United States (1991).
Stancovski, I., et al., "Mechanistic aspects of the opposing effects of monoclonal antibodies to the ERBB2 receptor on tumor growth," *Proc. Natl. Acad. Sci.* 88:8691-95, United States National Academy of Sciences, United States (1991).
Taipale, J. and Keski-Oja, J., "Growth factors in the extracellular matrix," *The FASEB Journal* 11:51-59, Federation of American Societies for Experimental Biology, United States (1997).
Kutty, G., et al., "Identification of a new member of transforming growth factor=beta superfamily in *Drosophila*: the first invertebrate activin gene," *Biochem. Biophys. Res. Commun.* 246(3):644-49, Elsevier B.V., Netherlands (1998).
Grzesik, W.J., et al., "Synthetic integrin-binding peptides promote adhesion and proliferation of human periodontal ligament cells in vitro," *J. Dent. Res.* 77(8):1606-12, International & American Associations for Dental Research, United States (1998).

Dennis, M.S., et al., "Albumin Binding as a General Strategy for Improving the Pharmacokinetics of Proteins," *JBC* 277(33):35035-43, The American Society for Biochemistry and Molecular Biology, Inc., United States (2002).

Li, L-S., et al., "Chemical Adaptor Immunotherapy: Design, Synthesis, and Evaluation of Novel Integrin-Targeting Devices," *J. Med. Chem.* 47:5630-40, American Chemical Society, United States (2004).

Riemer, A.B., et al., "Matching of trastuzumab (Herceptin) epitope mimics onto the surface of her-2/neu—a new method of epitope definition," *Mol. Immunol.* 42(9):1121-24, Elsevier B.V., Netherlands (2005).

Corte-Real, S., et al., "Intrabodies targeting the Kaposi sarcoma-associated herpesvirus latency antigen inhibit persistence in lymphoma cells," *Blood* 106:3797-802, American Society of Hematology, United States (2005).

Niu, G. and Carter, B., "Human Epidermal Growth Factor Receptor 2 Regulates Angiopoietin-2 Expression in Breast Cancer via AKT and Mitogen-Activated Protein Kinase Pathways," *Cancer Res.* 67:1487-93, American Association for Cancer Research, United States (2007).

Asano, R., et al., "Highly Effective Recombinant Format of a Humanized IgG-like Bispecific Antibody for Cancer Immunotherapy with Retargeting of Lymphocytes to Tumor Cells," *JBC* 282(38):27659-65, The American Society for Biochemistry and Molecular Biology, Inc., United States (2007).

Yu, L., et al., "Interaction between Bevavizumab and Murine VEGF-A: A Reassessment," *IOVS* 49(2):522-27, Association for Research in Vision and Ophthalmology, United States (2008).

Conner, et al., "Ex Vivo Evaluation of Anti-EpCAM Immunocytokine huKS-IL2 in Ovarian Cancer". *Journal of Immunotherapy* 27 (3): 211-219 (2004).

Schraa, et al., "RGD-Modified Anti-CD3 Antibodies Redirect Cytolytic Capacity of Cytotoxic T Lymphocytes Toward $\alpha_v\beta_3$ Expressing Endothelial Cells", *International Journal of Cancer 112* (2): 279-285 (2004).

Abraham, et al., "Synthesis of the Next-Generation Therapeutic Antibodies that Combine Cell Targeting and Antibody-Catalyzed Prodrug Activation", *PNAS 104* (13): 5584-5589 (2007).

Serini, et al., "Integrins and Angiogenesis: A Sticky Business", *Experimental Cell Research 312* (5): 651-658 (2006).

Landon, et al., "Combinatorial Discovery of Tumor Targeting Peptides Using Phage Display", *Journal of Cellular Biochemistry 90* (3): 509-517 (2003).

Colman, "Effects of amino acid sequence changes on antibody-antigen interactions", *Research in Immunology 145* (1): 33-36 (1994).

Dela Cruz, et al., "Recombinant Anti-Human HER2/neu IgG3-(GM-CSF) Fusion Protein Retains Antigen Specificity and Cytokine Function and Demonstrates Antitumor Activity", *J Immunology 165*: 5112-5121 (2000).

Dufner, et al., "Harnessing phage and ribosome display for antibody optimisation", *Trends in Biotechnology 24* (11): 523-529 (2006).

Helguera, et al., "Vaccination with novel combinations of anti-HER2/neu cytokines fusion proteins and soluble protein antigen elicits a protective immune response against HER2/neu expressing tumors", *Vaccine 24*: 304-316 (2006).

\* cited by examiner

SEQUENCE LISTING

```
<160> NUMBER OF SEQ ID NOS: 66

<210> SEQ ID NO 1
<211> LENGTH: 4
<212> TYPE: PRT
<213> ORGANISM: Artificial Sequence
<220> FEATURE:
<223> OTHER INFORMATION: Synthetic sequence

<400> SEQUENCE: 1

Gly Gly Gly Ser
1

<210> SEQ ID NO 2
<211> LENGTH: 15
<212> TYPE: PRT
<213> ORGANISM: Artificial Sequence
<220> FEATURE:
<223> OTHER INFORMATION: Synthetic sequence

<400> SEQUENCE: 2

Ser Ser Gly Gly Gly Gly Ser Gly Gly Gly Gly Gly Gly Ser Ser
1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: Synthetic sequence

<400> SEQUENCE: 3

Tyr Cys Arg Gly Asp Cys Thr
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic sequence

<400> SEQUENCE: 4

Pro Cys Arg Gly Asp Cys Leu
1               5

<210> SEQ ID NO 5
<211> LENGTH: 7
<212> TYPE: PRT
```

```
<213> ORGANISM: Artificial Sequence
<220> FEATURE:
<223> OTHER INFORMATION: Synthetic sequence

<400> SEQUENCE: 5

Thr Cys Arg Gly Asp Cys Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic sequence

<400> SEQUENCE: 6

Leu Cys Arg Gly Asp Cys Phe
1               5

<210> SEQ ID NO 7
<211> LENGTH: 28
<212> TYPE: PRT
<213> ORGANISM: Artificial Sequence
<220> FEATURE:
<223> OTHER INFORMATION: Synthetic sequence

<400> SEQUENCE: 7

Met Gly Ala Gln Thr Asn Phe Met Pro Met Asp Asp Leu Glu Gln Arg
1               5                   10                  15

Leu Tyr Glu Gln Phe Ile Leu Gln Gln Gly Leu Glu
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic sequence

<400> SEQUENCE: 8

Met Gly Ala Gln Thr Asn Phe Met Pro Met Asp Asn Asp Glu Leu Leu
1               5                   10                  15

Leu Tyr Glu Gln Phe Ile Leu Gln Gln Gly Leu Glu
            20                  25

<210> SEQ ID NO 9
<211> LENGTH: 28
<212> TYPE: PRT
<213> ORGANISM: Artificial Sequence
<220> FEATURE:
<223> OTHER INFORMATION: Synthetic sequence

<400> SEQUENCE: 9

Met Gly Ala Gln Thr Asn Phe Met Pro Met Asp Ala Thr Glu Thr Arg
1               5                   10                  15

Leu Tyr Glu Gln Phe Ile Leu Gln Gln Gly Leu Glu
            20                  25

<210> SEQ ID NO 10
<211> LENGTH: 54
<212> TYPE: PRT
<213> ORGANISM: Artificial Sequence
<220> FEATURE:
<223> OTHER INFORMATION: Synthetic sequence

<400> SEQUENCE: 10
```

```
Ala Gln Gln Glu Glu Cys Glu Trp Asp Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Trp Asp Pro Trp Thr
            35                  40                  45

Cys Glu His Met Leu Glu
            50

<210> SEQ ID NO 11
<211> LENGTH: 28
<212> TYPE: PRT
<213> ORGANISM: Artificial Sequence
<220> FEATURE:
<223> OTHER INFORMATION: Synthetic sequence

<400> SEQUENCE: 11

Met Gly Ala Gln Thr Asn Phe Met Pro Met Asp Asn Asp Glu Leu Leu
1               5                   10                  15

Asn Tyr Glu Gln Phe Ile Leu Gln Gln Gly Leu Glu
            20                  25

<210> SEQ ID NO 12
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 12

Pro Xaa Asp Asn Asp Xaa Leu Leu Asn Tyr
1               5                   10

<210> SEQ ID NO 13
<211> LENGTH: 19
<212> TYPE: PRT
<213> ORGANISM: Artificial Sequence
<220> FEATURE:
<223> OTHER INFORMATION: Synthetic sequence

<400> SEQUENCE: 13

Val Glu Pro Asn Cys Asp Ile His Val Met Trp Glu Trp Glu Cys Phe
1               5                   10                  15

Glu Arg Leu

<210> SEQ ID NO 14
<211> LENGTH: 27
<212> TYPE: PRT
<213> ORGANISM: Artificial Sequence
<220> FEATURE:
<223> OTHER INFORMATION: Synthetic sequence

<400> SEQUENCE: 14

Ser Phe Tyr Ser Cys Leu Glu Ser Leu Val Asn Gly Pro Ala Glu Lys
1               5                   10                  15

Ser Arg Gly Gln Trp Asp Gly Cys Arg Lys Lys
            20                  25
```

<210> SEQ ID NO 15
<211> LENGTH: 11
<212> TYPE: PRT
<213> ORGANISM: Artificial Sequence
<220> FEATURE:
<223> OTHER INFORMATION: Synthetic sequence

<400> SEQUENCE: 15

Ala Cys Asp Cys Arg Gly Asp Cys Phe Cys Gly
1               5                   10

<210> SEQ ID NO 16
<211> LENGTH: 58
<212> TYPE: PRT
<213> ORGANISM: Artificial Sequence
<220> FEATURE:
<223> OTHER INFORMATION: Synthetic sequence

<400> SEQUENCE: 16

Val Asp Asn Lys Phe Asn Lys Glu Leu Glu Lys Ala Tyr Asn Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 17
<211> LENGTH: 58
<212> TYPE: PRT
<213> ORGANISM: Artificial Sequence
<220> FEATURE:
<223> OTHER INFORMATION: Synthetic sequence

<400> SEQUENCE: 17

Val Asp Asn Lys Phe Asn Lys Glu Met Trp Ile Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 18
<211> LENGTH: 58
<212> TYPE: PRT
<213> ORGANISM: Artificial Sequence
<220> FEATURE:
<223> OTHER INFORMATION: Synthetic sequence

<400> SEQUENCE: 18

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 19
<211> LENGTH: 18
<212> TYPE: PRT
<213> ORGANISM: Artificial Sequence
<220> FEATURE:
<223> OTHER INFORMATION: Synthetic sequence

<400> SEQUENCE: 19

Ser Ser Gly Gly Gly Gly Ser Gly Gly Gly Gly Gly Gly Ser Ser Arg
1               5                   10                  15

Ser Ser

<210> SEQ ID NO 20
<211> LENGTH: 60
<212> TYPE: PRT
<213> ORGANISM: Artificial Sequence
<220> FEATURE:
<223> OTHER INFORMATION: Synthetic sequence

<400> SEQUENCE: 20

Met Gly Ala Gln Thr Asn Phe Met Pro Met Asp Asn Asp Glu Leu Leu
1               5                   10                  15

Leu Tyr Glu Gln Phe Ile Leu Gln Gln Gly Leu Glu Gly Gly Ser Gly
                20                  25                  30

Ser Thr Ala Ser Ser Gly Ser Gly Ser Ser Leu Gly Ala Gln Thr Asn
            35                  40                  45

Phe Met Pro Met Asp Asn Asp Glu Leu Leu Leu Tyr
        50                  55                  60

<210> SEQ ID NO 21
<211> LENGTH: 16
<212> TYPE: PRT
<213> ORGANISM: Artificial Sequence
<220> FEATURE:
<223> OTHER INFORMATION: Synthetic sequence

<400> SEQUENCE: 21

Ala Gln Gln Glu Glu Cys Glu Phe Ala Pro Trp Thr Cys Glu His Met
1               5                   10                  15

<210> SEQ ID NO 22
<211> LENGTH: 106
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(50)
<223> OTHER INFORMATION: Any one or all of residues 1-50 can either be
      present or absent. If present, Xaa can be any naturally occurring
      amino acid.
<220> FEATURE:
<221> NAME/KEY: misc_feature
<222> LOCATION: (57)..(106)
<223> OTHER INFORMATION: Any one or all of residues 57-106 can either be
      present or absent. If present, Xaa can be any naturally occurring
      amino acid.

<400> SEQUENCE: 22

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45
```

```
Xaa Xaa Glu Phe Ala Pro Trp Thr Xaa Xaa Xaa Xaa Xaa Xaa
     50              55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa
            100                 105

<210> SEQ ID NO 23
<211> LENGTH: 54
<212> TYPE: PRT
<213> ORGANISM: Artificial Sequence
<220> FEATURE:
<223> OTHER INFORMATION: Synthetic sequence

<400> SEQUENCE: 23

Ala Gln Gln Glu Glu Cys Glu Phe Ala Pro Trp Thr Cys Glu His Met
 1               5                  10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Phe Ala Pro Trp Thr
        35                  40                  45

Cys Glu His Met Leu Glu
    50

<210> SEQ ID NO 24
<211> LENGTH: 16
<212> TYPE: PRT
<213> ORGANISM: Artificial Sequence
<220> FEATURE:
<223> OTHER INFORMATION: Synthetic sequence

<400> SEQUENCE: 24

Ala Gln Gln Glu Glu Cys Glu Leu Ala Pro Trp Thr Cys Glu His Met
 1               5                  10                  15

<210> SEQ ID NO 25
<211> LENGTH: 106
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(50)
<223> OTHER INFORMATION: Any one or all of residues 1-50 can either be
      present or absent. If present, Xaa can be any naturally occurring
      amino acid.
<220> FEATURE:
<221> NAME/KEY: misc_feature
<222> LOCATION: (57)..(106)
<223> OTHER INFORMATION: Any one or all of residues 57-106 can either be
      present or absent. If present, Xaa can be any naturally occurring
      amino acid.

<400> SEQUENCE: 25

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Glu Leu Ala Pro Trp Thr Xaa Xaa Xaa Xaa Xaa Xaa Xaa Xaa
     50              55                  60
```

```
Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa
            100                 105
```

```
<210> SEQ ID NO 26
<211> LENGTH: 54
<212> TYPE: PRT
<213> ORGANISM: Artificial Sequence
<220> FEATURE:
<223> OTHER INFORMATION: Synthetic sequence

<400> SEQUENCE: 26

Ala Gln Gln Glu Glu Cys Glu Leu Ala Pro Trp Thr Cys Glu His Met
 1               5                  10                  15

Gly Ser Gly Ser Ala Thr Gly Gly Ser Gly Ser Thr Ala Ser Ser Gly
             20                  25                  30

Ser Gly Ser Ala Thr His Gln Glu Glu Cys Glu Leu Ala Pro Trp Thr
         35                  40                  45

Cys Glu His Met Leu Glu
     50
```

```
<210> SEQ ID NO 27
<211> LENGTH: 16
<212> TYPE: PRT
<213> ORGANISM: Artificial Sequence
<220> FEATURE:
<223> OTHER INFORMATION: Synthetic sequence

<400> SEQUENCE: 27

Ala Gln Gln Glu Glu Cys Glu Phe Ser Pro Trp Thr Cys Glu His Met
 1               5                  10                  15
```

```
<210> SEQ ID NO 28
<211> LENGTH: 106
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(50)
<223> OTHER INFORMATION: Any one or all of residues 1-50 can either be
      present or absent. If present, Xaa can be any naturally occurring
      amino acid.
<220> FEATURE:
<221> NAME/KEY: misc_feature
<222> LOCATION: (57)..(106)
<223> OTHER INFORMATION: Any one or all of residues 57-106 can either be
      present or absent. If present, Xaa can be any naturally occurring
      amino acid.

<400> SEQUENCE: 28

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa
         35                  40                  45

Xaa Xaa Glu Phe Ser Pro Trp Thr Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
```

```
                65                  70                  75                  80
Xaa Xaa Xaa Xaa Xaa Xaa Xaa Xaa Xaa Xaa Xaa Xaa Xaa Xaa Xaa Xaa
                    85                  90                  95

Xaa Xaa Xaa Xaa Xaa Xaa Xaa Xaa Xaa Xaa
            100                 105

<210> SEQ ID NO 29
<211> LENGTH: 54
<212> TYPE: PRT
<213> ORGANISM: Artificial Sequence
<220> FEATURE:
<223> OTHER INFORMATION: Synthetic sequence

<400> SEQUENCE: 29

Ala Gln Gln Glu Glu Cys Glu Phe Ser Pro Trp Thr Cys Glu His Met
1               5                   10                  15

Gly Ser Gly Ser Ala Thr Gly Gly Ser Gly Ser Thr Ala Ser Ser Gly
                20                  25                  30

Ser Gly Ser Ala Thr His Gln Glu Glu Cys Glu Phe Ser Pro Trp Thr
            35                  40                  45

Cys Glu His Met Leu Glu
        50

<210> SEQ ID NO 30
<211> LENGTH: 16
<212> TYPE: PRT
<213> ORGANISM: Artificial Sequence
<220> FEATURE:
<223> OTHER INFORMATION: Synthetic sequence

<400> SEQUENCE: 30

Ala Gln Gln Glu Glu Cys Glu Leu Glu Pro Trp Thr Cys Glu His Met
1               5                   10                  15

<210> SEQ ID NO 31
<211> LENGTH: 106
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(50)
<223> OTHER INFORMATION: Any one or all of residues 1-50 can either be
      present or absent. If present, Xaa can be any naturally occurring
      amino acid.
<220> FEATURE:
<221> NAME/KEY: misc_feature
<222> LOCATION: (57)..(106)
<223> OTHER INFORMATION: Any one or all of residues 57-106 can either be
      present or absent. If present, Xaa can be any naturally occurring
      amino acid.

<400> SEQUENCE: 31

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Glu Leu Glu Pro Trp Thr Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80
```

Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa
            100                 105

<210> SEQ ID NO 32
<211> LENGTH: 54
<212> TYPE: PRT
<213> ORGANISM: Artificial Sequence
<220> FEATURE:
<223> OTHER INFORMATION: Synthetic sequence

<400> SEQUENCE: 32

Ala Gln Gln Glu Glu Cys Glu Leu Glu Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Leu Glu Pro Trp Thr
        35                  40                  45

Cys Glu His Met Leu Glu
    50

<210> SEQ ID NO 33
<211> LENGTH: 54
<212> TYPE: PRT
<213> ORGANISM: Artificial Sequence
<220> FEATURE:
<223> OTHER INFORMATION: Synthetic sequence

<400> SEQUENCE: 33

Ala Gln Gln Glu Glu Cys Glu Phe Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Leu Ala Pro Trp Thr
        35                  40                  45

Cys Glu His Met Leu Glu
    50

<210> SEQ ID NO 34
<211> LENGTH: 54
<212> TYPE: PRT
<213> ORGANISM: Artificial Sequence
<220> FEATURE:
<223> OTHER INFORMATION: Synthetic sequence

<400> SEQUENCE: 34

Ala Gln Gln Glu Glu Cys Glu Phe Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Phe Ser Pro Trp Thr
        35                  40                  45

Cys Glu His Met Leu Glu
    50

<210> SEQ ID NO 35
<211> LENGTH: 28
<212> TYPE: PRT
<213> ORGANISM: Artificial Sequence
<220> FEATURE:
<223> OTHER INFORMATION: Synthetic sequence

```
<400> SEQUENCE: 35

Asn Phe Tyr Gln Cys Ile Glu Met Leu Ala Ser His Pro Ala Glu Lys
1               5                   10                  15

Ser Arg Gly Gln Trp Gln Glu Cys Arg Thr Gly Gly
            20                  25

<210> SEQ ID NO 36
<211> LENGTH: 28
<212> TYPE: PRT
<213> ORGANISM: Artificial Sequence
<220> FEATURE:
<223> OTHER INFORMATION: Synthetic sequence

<400> SEQUENCE: 36

Asn Phe Tyr Gln Cys Ile Glu Gln Leu Ala Leu Arg Pro Ala Glu Lys
1               5                   10                  15

Ser Arg Gly Gln Trp Gln Glu Cys Arg Thr Gly Gly
            20                  25

<210> SEQ ID NO 37
<211> LENGTH: 28
<212> TYPE: PRT
<213> ORGANISM: Artificial Sequence
<220> FEATURE:
<223> OTHER INFORMATION: Synthetic sequence

<400> SEQUENCE: 37

Asn Phe Tyr Gln Cys Ile Asp Leu Leu Met Ala Tyr Pro Ala Glu Lys
1               5                   10                  15

Ser Arg Gly Gln Trp Gln Glu Cys Arg Thr Gly Gly
            20                  25

<210> SEQ ID NO 38
<211> LENGTH: 28
<212> TYPE: PRT
<213> ORGANISM: Artificial Sequence
<220> FEATURE:
<223> OTHER INFORMATION: Synthetic sequence

<400> SEQUENCE: 38

Asn Phe Tyr Gln Cys Ile Glu Arg Leu Val Thr Gly Pro Ala Glu Lys
1               5                   10                  15

Ser Arg Gly Gln Trp Gln Glu Cys Arg Thr Gly Gly
            20                  25

<210> SEQ ID NO 39
<211> LENGTH: 28
<212> TYPE: PRT
<213> ORGANISM: Artificial Sequence
<220> FEATURE:
<223> OTHER INFORMATION: Synthetic sequence

<400> SEQUENCE: 39

Asn Phe Tyr Gln Cys Ile Glu Tyr Leu Ala Met Lys Pro Ala Glu Lys
1               5                   10                  15

Ser Arg Gly Gln Trp Gln Glu Cys Arg Thr Gly Gly
            20                  25

<210> SEQ ID NO 40
<211> LENGTH: 28
<212> TYPE: PRT
<213> ORGANISM: Artificial Sequence
<220> FEATURE:
<223> OTHER INFORMATION: Synthetic sequence
```

```
<400> SEQUENCE: 40

Asn Phe Tyr Gln Cys Ile Glu Ala Leu Gln Ser Arg Pro Ala Glu Lys
1               5                   10                  15

Ser Arg Gly Gln Trp Gln Glu Cys Arg Thr Gly Gly
            20                  25

<210> SEQ ID NO 41
<211> LENGTH: 28
<212> TYPE: PRT
<213> ORGANISM: Artificial Sequence
<220> FEATURE:
<223> OTHER INFORMATION: Synthetic sequence

<400> SEQUENCE: 41

Asn Phe Tyr Gln Cys Ile Glu Ala Leu Ser Arg Ser Pro Ala Glu Lys
1               5                   10                  15

Ser Arg Gly Gln Trp Gln Glu Cys Arg Thr Gly Gly
            20                  25

<210> SEQ ID NO 42
<211> LENGTH: 27
<212> TYPE: PRT
<213> ORGANISM: Artificial Sequence
<220> FEATURE:
<223> OTHER INFORMATION: Synthetic sequence

<400> SEQUENCE: 42

Asn Phe Tyr Gln Cys Ile Glu His Leu Ser Gly Ser Pro Ala Glu Lys
1               5                   10                  15

Ser Arg Gly Gln Trp Gln Glu Cys Arg Thr Gly
            20                  25

<210> SEQ ID NO 43
<211> LENGTH: 27
<212> TYPE: PRT
<213> ORGANISM: Artificial Sequence
<220> FEATURE:
<223> OTHER INFORMATION: Synthetic sequence

<400> SEQUENCE: 43

Asn Phe Tyr Gln Cys Ile Glu Ser Leu Ala Gly Gly Pro Ala Glu Lys
1               5                   10                  15

Ser Arg Gly Gln Trp Gln Glu Cys Arg Thr Gly
            20                  25

<210> SEQ ID NO 44
<211> LENGTH: 27
<212> TYPE: PRT
<213> ORGANISM: Artificial Sequence
<220> FEATURE:
<223> OTHER INFORMATION: Synthetic sequence

<400> SEQUENCE: 44

Asn Phe Tyr Gln Cys Ile Glu Ala Leu Val Gly Val Pro Ala Glu Lys
1               5                   10                  15

Ser Arg Gly Gln Trp Gln Glu Cys Arg Thr Gly
            20                  25

<210> SEQ ID NO 45
<211> LENGTH: 27
<212> TYPE: PRT
<213> ORGANISM: Artificial Sequence
<220> FEATURE:
<223> OTHER INFORMATION: Synthetic sequence
```

-continued

```
<400> SEQUENCE: 45

Asn Phe Tyr Gln Cys Ile Glu Met Leu Ser Leu Pro Pro Ala Glu Lys
1               5                   10                  15

Ser Arg Gly Gln Trp Gln Glu Cys Arg Thr Gly
            20                  25

<210> SEQ ID NO 46
<211> LENGTH: 27
<212> TYPE: PRT
<213> ORGANISM: Artificial Sequence
<220> FEATURE:
<223> OTHER INFORMATION: Synthetic sequence

<400> SEQUENCE: 46

Asn Phe Tyr Gln Cys Ile Glu Val Phe Trp Gly Arg Pro Ala Glu Lys
1               5                   10                  15

Ser Arg Gly Gln Trp Gln Glu Cys Arg Thr Gly
            20                  25

<210> SEQ ID NO 47
<211> LENGTH: 27
<212> TYPE: PRT
<213> ORGANISM: Artificial Sequence
<220> FEATURE:
<223> OTHER INFORMATION: Synthetic sequence

<400> SEQUENCE: 47

Asn Phe Tyr Gln Cys Ile Glu Gln Leu Ser Ser Gly Pro Ala Glu Lys
1               5                   10                  15

Ser Arg Gly Gln Trp Gln Glu Cys Arg Thr Gly
            20                  25

<210> SEQ ID NO 48
<211> LENGTH: 27
<212> TYPE: PRT
<213> ORGANISM: Artificial Sequence
<220> FEATURE:
<223> OTHER INFORMATION: Synthetic sequence

<400> SEQUENCE: 48

Asn Phe Tyr Gln Cys Ile Glu Leu Leu Ser Ala Arg Pro Ala Glu Lys
1               5                   10                  15

Ser Arg Gly Gln Trp Ala Glu Cys Arg Ala Gly
            20                  25

<210> SEQ ID NO 49
<211> LENGTH: 27
<212> TYPE: PRT
<213> ORGANISM: Artificial Sequence
<220> FEATURE:
<223> OTHER INFORMATION: Synthetic sequence

<400> SEQUENCE: 49

Asn Phe Tyr Gln Cys Ile Glu Ala Leu Ala Arg Thr Pro Ala Glu Lys
1               5                   10                  15

Ser Arg Gly Gln Trp Val Glu Cys Arg Ala Pro
            20                  25

<210> SEQ ID NO 50
<211> LENGTH: 18
<212> TYPE: DNA
<213> ORGANISM: Artificial Sequence
<220> FEATURE:
<223> OTHER INFORMATION: Synthetic sequence
```

```
<400> SEQUENCE: 50
gtggagtgca gggcgccg                                                   18

<210> SEQ ID NO 51
<211> LENGTH: 6
<212> TYPE: PRT
<213> ORGANISM: Artificial Sequence
<220> FEATURE:
<223> OTHER INFORMATION: Synthetic sequence

<400> SEQUENCE: 51

Val Glu Cys Arg Ala Pro
1               5

<210> SEQ ID NO 52
<211> LENGTH: 18
<212> TYPE: DNA
<213> ORGANISM: Artificial Sequence
<220> FEATURE:
<223> OTHER INFORMATION: Synthetic sequence

<400> SEQUENCE: 52
gctgagtgca gggctggg                                                   18

<210> SEQ ID NO 53
<211> LENGTH: 6
<212> TYPE: PRT
<213> ORGANISM: Artificial Sequence
<220> FEATURE:
<223> OTHER INFORMATION: Synthetic sequence

<400> SEQUENCE: 53

Ala Glu Cys Arg Ala Gly
1               5

<210> SEQ ID NO 54
<211> LENGTH: 18
<212> TYPE: DNA
<213> ORGANISM: Artificial Sequence
<220> FEATURE:
<223> OTHER INFORMATION: Synthetic sequence

<400> SEQUENCE: 54
caggagtgca ggacgggg                                                   18

<210> SEQ ID NO 55
<211> LENGTH: 6
<212> TYPE: PRT
<213> ORGANISM: Artificial Sequence
<220> FEATURE:
<223> OTHER INFORMATION: Synthetic sequence

<400> SEQUENCE: 55

Gln Glu Cys Arg Thr Gly
1               5

<210> SEQ ID NO 56
<211> LENGTH: 26
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (12)..(26)
<223> OTHER INFORMATION: Any one or all of residues 12-26 can either be
      present or absent. If present, Xaa can be any naturally occurring
      amino acid.
```

<400> SEQUENCE: 56

Met Gly Ala Gln Thr Asn Phe Met Pro Met Asp Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 57
<211> LENGTH: 116
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(50)
<223> OTHER INFORMATION: Any one of residues 1-50 can either be present
      or absent. If present, Xaa can be any naturally occurring amino
      acid.
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (67)..(116)
<223> OTHER INFORMATION: Any one of residues 67-116 can either be
      present or absent. If present, Xaa can be any naturally occurring
      amino acid.

<400> SEQUENCE: 57

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Ala Gln Gln Glu Glu Cys Glu Xaa Xaa Pro Trp Thr Cys Glu
    50                  55                  60

His Met Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa
        115

<210> SEQ ID NO 58
<211> LENGTH: 28
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: residue 7 is Asp or Glu
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 58

Asn Phe Tyr Gln Cys Ile Xaa Xaa Leu Xaa Xaa Xaa Pro Ala Glu Lys
1               5                   10                  15

Ser Arg Gly Gln Trp Gln Glu Cys Arg Thr Gly Gly
            20                  25

<210> SEQ ID NO 59
<211> LENGTH: 12
<212> TYPE: PRT
<213> ORGANISM: Artificial Sequence
<220> FEATURE:
<223> OTHER INFORMATION: Synthetic sequence

<400> SEQUENCE: 59

Arg Ala Ser Gln Asp Val Asn Thr Ala Val Ala Trp
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Synthetic sequence

<400> SEQUENCE: 60

Ser Ala Ser Phe Leu Tyr Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic sequence

<400> SEQUENCE: 61

Gln Gln His Tyr Thr Thr Pro Pro Thr
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic sequence

<400> SEQUENCE: 62

Gly Arg Asn Ile Lys Asp Thr Tyr Ile His
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Synthetic sequence

<400> SEQUENCE: 63

Arg Ile Tyr Pro Thr Asn Gly Tyr Thr Arg Tyr Ala Asp Ser Val Lys
1               5                   10                  15
Gly

<210> SEQ ID NO 64
<211> LENGTH: 11
<212> TYPE: PRT
<213> ORGANISM: Artificial Sequence
<220> FEATURE:

<223> OTHER INFORMATION: Synthetic sequence

<400> SEQUENCE: 64

Trp Gly Gly Asp Gly Phe Tyr Ala Met Asp Tyr
1               5                  10

<210> SEQ ID NO 65
<211> LENGTH: 109
<212> TYPE: PRT
<213> ORGANISM: Artificial Sequence
<220> FEATURE:
<223> OTHER INFORMATION: Synthetic sequence

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 66
<211> LENGTH: 120
<212> TYPE: PRT
<213> ORGANISM: Artificial Sequence
<220> FEATURE:
<223> OTHER INFORMATION: Synthetic sequence

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

US 8,454,960 B2

MULTISPECIFIC ANTIBODY TARGETING AND MULTIVALENCY THROUGH MODULAR RECOGNITION DOMAINS

CROSS-REFERENCE TO RELATED APPLICATIONS

This application is a non-provisional application that claims priority to U.S. Provisional Application Ser. No. 61/364,766 (filed Jul. 15, 2010, now abandoned). This application is also a continuation-in-part of U.S. patent application Ser. No. 12/747,883 (filed Jun. 11, 2010, now pending), which claims priority to International Patent Application No. PCT/US2008/088337 (filed Dec. 24, 2008, now expired), which claims priority to U.S. Provisional Application Ser. No. 61/018,816 (filed Jan. 3, 2008, now abandoned) and U.S. Provisional Application Ser. No. 61/022,767 (filed Jan. 22, 2008, now abandoned). The disclosures of the aforementioned patent applications are herein incorporated by reference in their entirety and for all purposes.

BACKGROUND OF THE INVENTION

1. Field of the Invention

This invention relates generally to antibodies containing one or more modular recognition domains, and more specifically to the use of antibodies containing one or more modular recognition domains to treat disease, as well as methods of making antibodies containing one or more modular recognition domains.

2. Background

Monoclonal antibodies (Abs) with catalytic activity can be used for selective prodrug activation and chemical transformations. Specifically, monoclonal Abs with aldolase activity have emerged as highly efficient catalysts for a number of chemical transformations, particularly aldol and retro-aldol reactions. The retro-aldolase activity of Abs, such as 38C2 and 93F3, have allowed researchers to design, synthesize, and evaluate prodrugs of various chemotherapeutic agents that can be activated by retro-aldol reactions. (Construction of 38C2 was described in WO 97/21803, which is herein incorporated by reference). 38C2 contains an antibody combining site that catalyzes the aldol addition reaction between an aliphatic donor and an aldehyde acceptor. In a syngeneic mouse model of neuroblastoma, systemic administration of an etoposide prodrug and intra-tumor injection of 38C2 inhibited tumor growth.

One drawback in the use of catalytic Abs is that they lack a device to target the catalytic Ab to the malignant cells. Previous studies demonstrated that in an antibody-directed enzyme prodrug therapy (ADEPT) or antibody-directed abzyme prodrug therapy (ADAPT) approach, enzymes or catalytic antibodies can be directed to tumor cells by chemical conjugation or recombinant fusion to targeting antibodies.

The development of bispecific or multi-specific molecules that target two or more cancer targets simultaneously and/or activate prodrugs offers a novel and promising solution to attacking cancer and other diseases. Such molecules can be based on immunoglobulin-like domains or subdomains as exemplified in FIG. 1 of the present application. Studies of bispecific antibodies that simultaneously target two tumor-associated antigens (e.g., growth factor receptors) for down-regulation of multiple cell proliferation/survival pathways have provided support for this approach. Traditionally, bispecific antibodies have been prepared by chemically linking two different monoclonal antibodies or by fusing two hybridoma cell lines to produce a hybrid-hybridoma. Other technologies that have created multispecific, and/or multi-valent molecules include dAbs, diabodies, T and Abs, nanobodies, BiTEs, SMIPs, darpins, DNLs, Affibodies, Duocalins, Adnectins, Fynomers Kunitz Domains Albu-dabs, DARTs, DVD-IG, Covx-bodies, peptibodies, scFv-Igs, SVD-Igs, dAb-Igs, Knob-in-Holes, and triomAbs. Although each of these molecules may bind one or more targets, they each present challenges with respect to retention of typical Ig function (e.g., half-life, effector function), production (e.g., yield, purity), valency, and simultaneous target recognition.

Some of the smaller, Ig subdomain- and non-Ig-domain-based multi-specific molecules may possess some advantages over the full-length or larger IgG-like molecules for certain clinical applications, such as for tumor radio-imaging and targeting, because of better tissue penetration and faster clearance from the circulation. On the other hand, IgG-like molecules may prove to be preferred over smaller fragments for other in vivo applications, specifically for oncology indications, by providing the Fc domain that confers long serum half-life and supports secondary immune function, such as antibody-dependent cellular cytotoxicity and complement-mediated cytotoxicity. Unlike their fragment counterparts, engineering and production of recombinant IgG-like multi-specific, multi-valent molecules has been, however, rather technically challenging due to their large size (150-200 kDa) and structural complexity. Success in the field, as judged by successful application in animal models, has been very limited. Recently, with the examination of a variety of constructs, the efficient expression of Fc domain-containing bi-specific molecules in mammalian cells has made some strides.

Another approach that has been used to target antibodies is through the use of peptibodies. Peptibodies are essentially peptide fusions with antibody Fc regions. Given the success of studies using random peptide libraries to find high-affinity peptide ligands for a wide variety of targets, fusion of such peptides to antibody Fc regions provides a means of making peptides into therapeutic candidates by increasing their circulatory half-life and activity through increased valency.

Protein interactions with other molecules are basic to biochemistry. Protein interactions include receptor-ligand interactions, antibody-antigen interactions, cell-cell contact and pathogen interactions with target tissues. Protein interactions can involve contact with other proteins, with carbohydrates, oligosaccharides, lipids, metal ions and like materials. The basic unit of protein interaction is the region of the protein involved in contact and recognition, and is referred to as the binding site or target site. Such units may be linear sequence(s) of amino acids or discontinuous amino acids that collectively form the binding site or target site.

Peptides derived from phage display libraries typically retain their binding characteristics when linked to other molecules. Specific peptides of this type can be treated as modular specificity blocks or molecular recognition domains (MRDs) that can, independently, or in combination with other protein scaffolds, create a single protein with binding specificities for several defined targets.

An example of such a defined target site is integrin. Integrins are a family of transmembrane cell adhesion receptors that are composed of α and β subunits and mediate cell attachment to proteins within the extracellular matrix. At present, eighteen α and eight β subunits are known; these form 24 different αβ heterodimers with different specificities for various extracellular matrix (ECM) cell-adhesive proteins. Ligands for various integrins include fibronectin, collagen, laminin, von Willebrand factor, osteopontin, thrombospondin, and vitronectin, which are all components of the ECM. Certain integrins can also bind to soluble ligands such as fibrinogen or to other adhesion molecules on adjacent cells. Integrins are known to exist in distinct activation states that exhibit different affinities for ligand. Recognition of soluble ligands by integrins strictly depends on specific changes in receptor conformation. This provides a molecular switch that controls the ability of cells to aggregate in an integrin dependent manner and to arrest under the dynamic flow conditions of the vasculature. This mechanism is well established for leukocytes and platelets that circulate within the blood stream in a resting state while expressing non-activated integrins. Upon stimulation through proinflammatory or prothrombotic agonists, these cell types promptly respond with a number of molecular changes including the switch of key integrins, β2 integrins for leukocytes and αvβ3 for platelets, from "resting" to "activated" conformations. This enables these cell types to arrest within the vasculature, promoting cell cohesion and leading to thrombus formation.

It has been demonstrated that a metastatic subset of human breast cancer cells expresses integrin αvβ3 in a constitutively activated form. This aberrant expression of αvβ3 plays a role in metastasis of breast cancer as well as prostate cancer, melanoma, and neuroblastic tumors. The activated receptor strongly promotes cancer cell migration and enables the cells to arrest under blood flow conditions. In this way, activation of αvβ3 endows metastatic cells with key properties likely to be critical for successful dissemination and colonization of target organs. Tumor cells that have successfully entered a target organ may further utilize αvβ3 to thrive in the new environment, as αvβ3 matrix interactions can promote cell survival and proliferation. For example, αvβ3 binding to osteopontin promotes malignancy and elevated levels of osteopontin correlate with a poor prognosis in breast cancer.

For these reasons, and for its established role in angiogenesis, the αvβ3 integrin is one of the most widely studied integrins. Antagonists of this molecule have significant potential for use in targeted drug delivery. One approach that has been used to target αvβ3 integrin uses the high binding specificity to αvβ3 of peptides containing the Arg-Gly-Asp (RGD) sequence. This tripeptide, naturally present in extracellular matrix proteins, is the primary binding site of the αvβ3 integrin. However, RGD based reporter probes are problematic due to fast blood clearance, high kidney and liver uptake, and fast tumor washout. Chemical modification of cyclized RGD peptides has been shown to increase their stability and valency. These modified peptides are then coupled to radio-isotopes and used either for tumor imaging or to inhibit tumor growth.

Integrin αvβ3 is one of the most well characterized integrin heterodimers and is one of several heterodimers that have been implicated in tumor-induced angiogenesis. While sparingly expressed in mature blood vessels, αvβ3 is significantly up-regulated during angiogenesis in vivo. The expression of αvβ3 correlates with aggressiveness of disease in breast and cervical cancer as well as in malignant melanoma. Recent studies suggest that αvβ3 may be useful as a diagnostic or prognostic indicator for some tumors. Integrin αvβ3 is particularly attractive as a therapeutic target due to its relatively limited cellular distribution. Integrin αvβ3 is not generally expressed on epithelial cells, and minimally expressed on other cell types. Furthermore, αvβ3 antagonists, including both cyclic RGD peptides and monoclonal antibodies, significantly inhibit cytokine-induced angiogenesis and the growth of solid tumor on the chick chorioallantoic membrane.

Another integrin heterodimer, αvβ5, is more widely expressed on malignant tumor cells and is likely involved in VEGF-mediated angiogenesis. It has been shown that αvβ3 and αvβ5 promote angiogenesis via distinct pathways: αvβ3 through bFGF and TNF-a, and αvβ5 through VEGF and TGF-α. It has also been shown that inhibition of Src kinase can block VEGF-induced, but not FGF2-induced, angiogenesis. These results strongly imply that FGF2 and VEGF activate different angiogenic pathways that require αvβ3 and αvβ5, respectively.

Integrins have also been implicated in tumor metastasis. Metastasis is the primary cause of morbidity and mortality in cancer. Malignant progression of melanoma, glioma, ovarian, and breast cancer have all been strongly linked with the expression of the integrin αvβ3 and in some cases with αvβ5. More recently, it has been shown that activation of integrin αvβ3 plays a significant role in metastasis in human breast cancer. A very strong correlation between expression of αvβ3 and breast cancer metastasis has been noted where normal breast epithelia are αvβ3 negative and approximately 50% of invasive lobular carcinomas and nearly all bone metastases in breast cancer express αvβ3. Antagonism of αvβ3 with a cyclic peptide has been shown to synergize with radioimmunotherapy in studies involving breast cancer xenografts.

Angiogenesis, the formation of new blood vessels from existing ones, is essential to many physiological and pathological processes. Normally, angiogenesis is tightly regulated by pro- and anti-angiogenic factors, but in the case of diseases such as cancer, ocular neovascular disease, arthritis and psoriasis, the process can go awry. The association of angiogenesis with disease has made the discovery of anti-angiogenic compounds attractive. Among the most promising phage-derived anti-angiogenic peptides described to date, are those that neutralize vascular endothelial growth factor (VEGF), and cytokine Ang2. See e.g., U.S. Pat. Nos. 6,660,843 and 7,138,370 respectively.

While the VEGFs and their receptors have been among the most extensively targeted molecules in the angiogenesis field, preclinical efforts targeting the more recently discovered angiopoietin-Tie2 pathway are underway. Both protein families involve ligand receptor interactions, and both include members whose functions are largely restricted postnatally to endothelial cells and some hematopoietic stem cell lineages. Tie2 is a receptor tyrosine kinase with four known ligands, angiopoietin-1 (Ang1) through angiopoietin-4 (Ang4), the best studied being Ang1 and Ang2. Ang1 stimulates phosphorylation of Tie2 and the Ang2 interaction with Tie2 has been shown to both antagonize and agonize Tie2 receptor phosphorylation. Elevated Ang2 expression at sites of normal and pathological postnatal angiogenesis circumstantially implies a proangiogenic role for Ang2. Vessel-selective Ang2 induction associated with angiogenesis has been demonstrated in diseases including cancer. In patients with colon carcinoma, Ang2 is expressed ubiquitously in tumor epithelium, whereas expression of Ang1 in tumor epithelium has been shown to be rare. The net gain of Ang2 activity has been suggested to be an initiating factor for tumor angiogenesis.

Other proteins directed towards cellular receptors are under clinical evaluation. HERCEPTIN® (Trastuzumab), developed by Genentech, is a recombinant humanized monoclonal antibody directed against the extracellular domain of the human epidermal tyrosine kinase receptor 2 (HER2 or ErbB2). The HER2 gene is overexpressed in 25% of invasive breast cancers, and is associated with poor prognosis and altered sensitivity to chemotherapeutic agents. HERCEPTIN® blocks the proliferation of ErbB2-overexpressing breast cancers, and is currently the only ErbB2 targeted antibody therapy approved by the FDA for the treatment of ErbB2 over-expressing metastatic breast cancer (MBC). In normal adult cells, few ErbB2 molecules exist at the cell surface ~20,000 per cell thereby limiting their signaling capacity and the likelihood of forming homo- and hetero-receptor complexes on the cell surface. When ErbB2 is overexpressed on the cell surface, ~500,000 per cell, multiple ErbB2 homo- and hetero-complexes are formed and cell signaling is stronger, resulting in enhanced responsiveness to growth factors and malignant growth. This explains why ErbB2 overexpression is an indicator of poor prognosis in breast tumors and may be predictive of response to treatment.

ErbB2 is a promising and validated target for breast cancer, where it is found both in primary tumor and metastatic sites. HERCEPTIN® induces rapid removal of ErbB2 from the cell surface, thereby reducing its availability to multimerize and ability to promote growth. Mechanisms of action of HERCEPTIN® observed in experimental in vitro and in vivo models include inhibition of proteolysis of ErbB2's extracellular domain, disruption of downstream signaling pathways such as phosphatidylinositiol 3-kinase (PI3K) and mitogen-activated protein kinase (MAPK) cascades, GI cell-cycle arrest, inhibition of DNA repair, suppression of angiogenesis and induction of antibody dependent cellular cytotoxicity (ADCC). Many patients with metastatic breast cancer who initially respond to HERCEPTIN®, however, demonstrate disease progression within one year of treatment initiation.

Another target cellular receptor is type 1 insulin-like growth factor-1 receptor (IGF1R), IGF1R is a receptor-tyrosine kinase that plays a critical role in signaling cell survival and proliferation. The IGF system is frequently deregulated in cancer cells by the establishment of autocrine loops involving IGF-I or IGF-II and/or IGF1R overexpression. Moreover, epidemiological studies have suggested a link between elevated IGF levels and the development of major human cancers, such as breast, colon, lung and prostate cancer. Expression of IGFs and their cognate receptors has been correlated with disease stage, reduced survival, development of metastases and tumor de-differentiation.

Besides IGF1R, epidermal growth factor receptor (EGFR) has also been implicated in the tumorigenesis of numerous cancers. Effective tumor inhibition has been achieved both experimentally and clinically with a number of strategies that antagonize either receptor activity. Because of the redundancy of growth signaling pathways in tumor cells, inhibition of one receptor function (e.g., EGFR) could be effectively compensated by up-regulation of other growth factor receptor (e.g., IGF 1R) mediated pathways. For example, a recent study has shown that malignant glioma cell lines expressing equivalent EGFR had significantly different sensitivity to EGFR inhibition depending on their capability to activate IGF1R and its downstream signaling pathways. Other studies have also demonstrated that overexpression and/or activation of IGF1R in tumor cells might contribute to their resistance to chemotherapeutic agents, radiation, or antibody therapy such as HERCEPTIN®. And consequently, inhibition of IGF1R signaling has resulted in increased sensitivity of tumor cells to HERCEPTIN®.

EGFR is a receptor tyrosine kinase that is expressed on many normal tissues as well as neoplastic lesions of most organs. Overexpression of EGFR or expression of mutant forms of EGFR has been observed in many tumors, particularly epithelial tumors, and is associated with poor clinical prognosis. Inhibition of signaling through EGFR induces an anti-tumor effect. With the FDA approval of cetuximab, also known as ERBITUX® (a mouse/human chimeric antibody) in February of 2004, EGFR became an approved antibody drug target for the treatment of metastatic colorectal cancer. In March of 2006, ERBITUX® also received FDA approval for the treatment of squamous cell carcinoma of the head and neck (SCCHN). More recently, panitumumab, also known as VECTIBIX®, a fully human antibody directed against EGFR, was approved for metastatic colorectal cancer. Neither ERBITUX® or VECTIBIX® is a stand-alone agent in colorectal cancer—they were approved as add-ons to existing colorectal regimens. In colorectal cancer, ERBITUX® is given in combination with the drug irinotecan and VECTIBIX® is administered after disease progression on, or following fluoropyrimidine-, oxaliplatin-, and irinotecan-containing chemotherapy regimens. ERBITUX® has been approved as a single agent in recurrent or metastatic SCCHN only where prior platinum-based chemotherapy has failed. Advanced clinical trials which use these drugs to target non-small cell lung carcinoma are ongoing. The sequence of the heavy and light chains of ERBITUX® are well known in the art (see for example, Goldstein, et al., Clin. Cancer Res. 1:1311 (1995); U.S. Pat. No. 6,217,866, which are herein incorporated by reference).

An obstacle in the utilization of a catalytic antibody for selective prodrug activation in cancer therapy has been systemic tumor targeting. An efficient alternative would be using the catalytic antibody fused to a targeting peptide located outside the antibody combining site, thereby leaving the active site available for the prodrug activation as described herein. For example, the fusion of Ab 38C2 to an integrin $\alpha v\beta 3$-binding peptide would selectively localize the antibody to the tumor and/or the tumor vasculature and trigger prodrug activation at that site. The potential therapy of this approach is supported by preclinical and clinical data suggesting that peptides can be converted into viable drugs through attachment to the isolated Fc domain of an immunoglobulin. The present invention describes an approach based on the adaptation of target binding peptides, or modular recognition domains (MRDs), which are fused to full-length antibodies that effectively target tumor cells or soluble molecules while retaining the prodrug activation capability of the catalytic antibody. The current invention calls for the fusion of MRDs to the N- and/or C-termini of an antibody. So as not to significantly mitigate binding to the antibody's traditional binding site, the antibody's specificity remains intact after MRD addition thereby resulting in a multi-specific antibody.

As depicted in FIG. 2, MRDs, designated by triangles, circles, diamonds, and squares, can be appended on any of the termini of either heavy or light chains of a typical IgG antibody. The first schematic represents a simple peptibody with a peptide fused to the C-terminus of an Fc. This approach provides for the preparation of bi-, tri-, tetra-, and penta-specific antibodies. Display of a single MRD at each N- and C-termini of an IgG provides for octavalent display of the MRD. As an alternative to the construction of bi- and multi-functional antibodies through the combination of antibody variable domains, high-affinity peptides selected from, for example, phage display libraries or derived from natural ligands, may offer a highly versatile and modular approach to the construction of multifunctional antibodies that retain both the binding and half-life advantages of traditional antibodies. MRDs can also extend the binding capacity of non-catalytic antibodies, providing for an effective approach to extend the binding functionality of antibodies, particularly for therapeutic purposes.

Therapeutic antibodies represent the most rapidly growing sector of the pharmaceutical industry. Treatment with bispecific antibodies and defined combinations of monoclonal antibodies are expected to show therapeutic advantages over established and emerging antibody monotherapy regimens. However, the cost of developing and producing such therapies has limited their consideration as viable treatments for most indications. There is, therefore, a great need for developing multispecific and multivalent antibodies having superior drug properties with substantially reduced production costs as compared to conventional bispecific antibodies and combinations of monoclonal antibodies.

BRIEF SUMMARY OF THE INVENTION

The present invention is directed towards a full-length antibody comprising at least one modular recognition domain (MRD). In some embodiments, the full-length antibody comprises multiple MRDs. In additional non-exclusive embodiments, the full-length antibody comprises more than one type of MRD (i.e. multiple MRDs having the same or different specificities). Also embodied in the present invention are variants and derivatives of such antibodies comprising a MRD. Variants and derivatives of such antibodies comprising more than one type of MRD are also encompassed by the invention.

The MRDs of the MRD containing antibodies can be attached to the antibodies at any location on the antibody. In one aspect, the MRD is operably linked to the C-terminal end of the heavy chain of the antibody. In another aspect, the MRD is operably linked to the N-terminal end of the heavy chain of the antibody. In yet another aspect, the MRD is operably linked to the C-terminal end of the light chain of the antibody. In another aspect, the MRD is operably linked to the N-terminal end of the light chain of the antibody. In another aspect, two or more MRDs are operably linked to the same antibody location, e.g., any terminal end of the antibody. In another aspect, two or more MRDs are operably linked to at least two different antibody locations, e.g., two or more different terminal ends of the antibody.

The antibodies of the MRD containing antibodies can be any immunoglobulin molecule that binds to an antigen and can be of any type, class, or subclass. In some embodiments, the antibody is an IgG. In some embodiments, the antibody is a polyclonal, monoclonal, multispecific, human, humanized, or chimeric antibody. In a specific embodiment, the antibody is chimeric or humanized. In another specific embodiment, the antibody is human. In other non-exclusive embodiments, the antibodies also include modifications that do not interfere with their ability to bind antigen.

In preferred embodiments, the antibody of the MRD-containing antibody binds to a validated target. In one embodiment, the antibody binds to a cell surface antigen. In another embodiment, the antibody binds to an angiogenic factor. In a further embodiment, the antibody binds to an angiogenic receptor.

In some embodiments, the antibody binds to a target that is selected from the group consisting of EGFR, ErbB2, ErbB3, ErbB4, CD20, insulin-like growth factor-I receptor, VEGF, VEGF-R and prostate specific membrane antigen.

In one specific embodiment, the antibody the antibody of the MRD-containing antibody binds to EGFR. In another specific embodiment, the antibody binds to the same epitope as Erbitux® antibody or competitively inhibits binding of the Erbitux® antibody to EGFR. In a further specific embodiment, the antibody is the Erbitux® antibody.

In a specific embodiment, the antibody of the MRD-containing antibody binds to ErbB2. In another specific embodiment, the antibody binds to the same epitope as HERCEPTIN® (trastuzumab) antibody or competitively inhibits HERCEPTIN® (trastuzumab) antibody. In another specific embodiment, the antibody is an antibody that comprises the CDR sequences of SEQ ID NOs: 59-64. In a further specific embodiment, the antibody is the HERCEPTIN® (trastuzumab) antibody.

In another specific embodiment, the antibody binds to VEGF.

MRDs can be linked to an antibody or other MRDs directly or through a linker. A linker can be any chemical structure that allows for the MRD that has been linked to an antibody to bind its target. In some embodiments, the linker is a chemical linker described herein or otherwise known in the art. In other embodiments the linker is a polypeptide linker described herein or otherwise known in the art. In one aspect, the antibody and the MRD are operably linked through a linker peptide. In one aspect, the linker peptide is between 2 to 20 peptides long, or between 4 to 10 or about 4 to 15 peptides long. In one aspect, the linker peptide comprises the sequence GGGS (SEQ ID NO:1), the sequence SSGGGGSGGGGGSS (SEQ ID NO:2), or the sequence SSGGGGSGGGGGSSRSS (SEQ ID NO:19). Other linkers containing a core sequence of GGGS as shown in SEQ ID NO:1 are also included herein wherein the linker peptide is from about 4-20 amino acids.

The MRDs can be any target binding peptide. In some embodiments, the MRD target is a soluble factor. In other embodiments, the MRD target is a transmembrane protein such as a cell surface receptor. For example, in some embodiments, the MRD target is selected from the group consisting of an angiogenic cytokine and an integrin. In a specific embodiment, the MRD comprises the sequence of SEQ ID NO:8. In another specific embodiment, the MRD comprises the sequence of SEQ ID NO:14.

In one embodiment, the MRD is about 2 to 150 amino acids. In another embodiment, the MRD is about 2 to 60 amino acids.

In an additional embodiment, the MRD-containing antibody comprises an MRD containing a sequence selected from the group consisting of SEQ ID NO:8, and SEQ ID NO:14.

In other embodiments, the MRD binds to a target selected from the group consisting of: an integrin, a cytokine, an angiogenic cytokine, vascular endothelial growth factor (VEGF), insulin-like growth factor-I receptor (IGF-IR), a tumor antigen, CD20, an epidermal growth factor receptor (EGFR), the ErbB2 receptor, the ErbB3 receptor, tumor associated surface antigen epithelial cell adhesion molecule (Ep-CAM), an angiogenic factor, an angiogenic receptor, cell surface antigen, soluble ligand, vascular homing peptide, and nerve growth factor In other embodiments, the MRD binds to a target selected from the group consisting of: a cytokine, soluble ligand, VEGF receptor 1, and VEGF receptor 2.

In one embodiment, the target of the MRD is a cellular antigen. In a specific embodiment of the present invention, the target of the MRD is CD20.

In another embodiment, the target of the MRD is an integrin. In one aspect, the peptide sequence of the integrin targeting MRD is YCRGDCT (SEQ ID NO:3). In another aspect, the peptide sequence of the integrin targeting MRD is PCRGDCL (SEQ ID NO:4). In yet another aspect, the peptide sequence of the integrin targeting MRD is TCRGDCY (SEQ ID NO:5). In another aspect, the peptide sequence of the integrin targeting MRD is LCRGDCF (SEQ ID NO:6).

In an additional embodiment, the target of the MRD is an angiogenic cytokine. In one aspect, the peptide sequence of the angiogenic cytokine targeting (i.e. binding) MRD is MGAQTNFMPMDDLEQRLYEQFILQQGLE (SEQ ID NO:7). In another aspect, the peptide sequence of the angiogenic cytokine targeting MRD is MGAQTNFMPMDN- DELLLYEQFILQQGLE (SEQ ID NO:8). In yet another aspect, the peptide sequence of the angiogenic cytokine targeting MRD is MGAQTNFMPMDATE TRLYEQFILQQGLE (SEQ ID NO:9). In another aspect, the peptide sequence of the angiogenic cytokine targeting MRD is AQQEECEWDPWTCEHMGSGSATG GSGSTASSGSGSATHQEECEWDPWTCEHMLE (SEQ ID NO:10). In another aspect, the peptide sequence of the angiogenic cytokine targeting MRD is MGAQTNFM PMDNDELLNYEQFILQQGLE (SEQ ID NO:11). In another aspect, the peptide sequence of the angiogenic cytokine targeting MRD is PXDNDXLLNY (SEQ ID NO:12), where X is one of the 20 naturally-occurring amino acids. In another aspect, the targeting MRD peptide has the core sequence MGAQTNFMPMDXn (SEQ ID NO:56), wherein X is any amino acid and n is from about 0 to 15.

In a further embodiment, the targeting MRD peptide contains a core sequence selected from:

```
                                          (SEQ ID NO: 22)
XnEFAPWTXn where n is from about 0 to 50 amino
acid residues;

(SEQ ID NO: 25)
XnELAPWTXn where n is from about 0 to 50 amino
acid residues;

(SEQ ID NO: 28)
XnEFSPWTXn where n is from about 0 to 50 amino
acid residues;

(SEQ ID NO: 31)
XnELEPWTXn where n is from about 0 to 50 amino
acid residues;
and (SEQ ID NO: 57)
XnAQQEECEX₁X₂PWTCEHMXn where n is from about
0 to 50 amino acid residues and X, X₁ and X₂ are
any amino acid.
```

Exemplary peptides containing such core peptides encompassed by the invention include for example:

```
                                          (SEQ ID NO: 21)
AQQEECEFAPWTCEHM;

(SEQ ID NO: 23)
AQQEECEFAPWTCEHMGSGSATGGSGSTASSGSGSATHQEECEFAPWTC
EHMLE;

(SEQ ID NO: 24)
AQQEECELAPWTCEHM;

(SEQ ID NO: 26)
AQQEECELAPWTCEHMGSGSATGGSGSTASSGSGSATHQEECELAPWTC
EHMLE;

(SEQ ID NO: 27)
AQQEECEFSPWTCEHM;

(SEQ ID NO: 29)
AQQEECEFSPWTCEHMGSGSATGGSGSTASSGSGSATHQEECEFSPWTC
EHMLE 2xConFS;

(SEQ ID NO: 30)
AQQEECELEPWTCEHM;

(SEQ ID NO: 32)
AQQEECELEPWTCEHMGSGSATGGSGSTASSGSGSATHQEECELEPWTC
EHMLE;
```

-continued

```
                                          (SEQ ID NO: 33)
AQQEECEFAPWTCEHMGSGSATGGSGSTASSGSGSATHQEECELAPWTC
EHMLE;

(SEQ ID NO: 34)
AQQEECEFAPWTCEHMGSGSATGGSGSTASSGSGSATHQEECEFSPWTC
EHMLE;
and (SEQ ID NO: 10)
AQQEECEWDPWTCEHMGSGSATGGSGSTASSGSGSATHQEECEWDPWTC
EHMLE.
```

In one embodiment, the target of the MRD is ErbB2. In another embodiment, the target to which the MRD binds is ErbB3. In an additional embodiment, the target to which the MRD binds is tumor-associated surface antigen epithelial cell adhesion molecule (Ep-CAM).

In one embodiment, the target to which the MRD binds is VEGF. In one aspect, the peptide sequence of the VEGF targeting MRD is VEPNCDIHVMWEWECFERL (SEQ ID NO:13).

In one embodiment, the target to which the MRD binds is an insulin-like growth factor-I receptor (IGF 1R). In one aspect, the peptide sequence of the insulin-like growth factor-I receptor targeting MRD comprises SFYSCLESLVNG-PAEKSRGQWDGCRKK (SEQ ID NO:14). Other illustrative IGF1R targeting MRDs include, for example, a peptide sequence having the formula NFYQCIX$_1$X$_2$LX$_3$X$_4$X$_5$PAEKSRGQWQECRTGG (SEQ ID NO:58), wherein X$_1$ is E or D; X$_2$ is any amino acid; X$_3$ is any amino acid; X$_4$ is any amino acid; and X$_5$ is any amino acid.

Illustrative peptides that contain such formula include:

| | |
|---|---|
| NFYQCIEMLASHPAEKSRGQWQECRTGG; | (SEQ ID NO: 35) |
| NFYQCIEQLALRPAEKSRGQWQECRTGG; | (SEQ ID NO: 36) |
| NFYQCIERLVTGPAEKSRGQWQECRTGG; | (SEQ ID NO: 38) |
| NFYQCIEYLAMKPAEKSRGQWQECRTGG; | (SEQ ID NO: 39) |
| NFYQCIEALQSRPAEKSRGQWQECRTGG; | (SEQ ID NO: 40) |
| NFYQCIEALSRSPAEKSRGQWQECRTGG; | (SEQ ID NO: 41) |
| NFYQCIEHLSGSPAEKSRGQWQECRTG; | (SEQ ID NO: 42) |
| NFYQCIESLAGGPAEKSRGQWQECRTG; | (SEQ ID NO: 43) |
| NFYQCIEALVGVPAEKSRGQWQECRTG; | (SEQ ID NO: 44) |
| NFYQCIEMLSLPPAEKSRGQWQECRTG; | (SEQ ID NO: 45) |
| NFYQCIEVFWGRPAEKSRGQWQECRTG; | (SEQ ID NO: 46) |
| NFYQCIEQLSSGPAEKSRGQWQECRTG; | (SEQ ID NO: 47) |
| NFYQCIELLSARPAEKSRGQWAECRAG; | (SEQ ID NO: 48) |
| and | |
| NFYQCIEALARTPAEKSRGQWVECRAP. | (SEQ ID NO: 49) |

Other illustrative IGF1R targeting MRDs include, for example, a peptide sequence having the formula:

| | |
|---|---|
| NFYQCIDLLMAYPAEKSRGQWQECRTGG; | (SEQ ID NO: 37) |

In one embodiment, the target of the MRD is a tumor antigen.

In one embodiment, the target of the MRD is an epidermal growth factor receptor (EGFR). In another embodiment of the present invention, the target of the MRD is an angiogenic factor. In an additional embodiment, the target of the MRD is an angiogenic receptor.

In another embodiment, the MRD is a vascular homing peptide. In one aspect, the peptide sequence of the vascular homing peptide MRD comprises the sequence ACDCRGD-CFCG (SEQ ID NO:15).

In one embodiment, the target of the MRD is a nerve growth factor.

In another embodiment, the antibody and/or MRD binds to EGFR, ErbB2, ErbB3, ErbB4, CD20, insulin-like growth factor-I receptor, or prostate specific membrane antigen.

In one aspect, the peptide sequence of the EGFR targeting (binding) MRD is VDNKFNKELEKAYNEIRNLPNLNG-WQMTAFIASLVDDPSQSANLLAEAKKLNDA QAPK (SEQ ID NO:16). In one aspect, the peptide sequence of the EGFR targeting MRD is VDNKFNKEMWIAWEEIRNLP-NLNGWQMTAFIASLVDDPSQSANLLAEA KKLNDAQAPK (SEQ ID NO:17). In another aspect, the peptide sequence of the ErbB2 targeting MRD is VDNK-FNKEMRNAYWEIALLPNLN-NQQKRAFIRSLYDDPSQSA NLLAEAKKLNDAQAPK (SEQ ID NO:18).

The present invention also relates to an isolated polynucleotide comprising a nucleotide sequence encoding an MRD containing antibody. In one aspect, a vector comprises a polynucleotide sequence encoding an MRD containing antibody. In another aspect, the polynucleotide sequence encoding an MRD containing antibody is operatively linked with a regulatory sequence that controls expression on the polynucleotide. In an additional aspect, a host cell comprises the polynucleotide sequence encoding an MRD containing antibody.

Methods of making MRD-antibody fusions (i.e. MRD-containing antibodies) are also provided, as are the use of these MRD-antibody fusions in diagnostic and therapeutic applications. The present invention also relates to methods of designing and making MRD-containing antibodies having a full-length antibody comprising a MRD. In one aspect, the MRD is derived from a phage display library. In another aspect, the MRD is derived from natural ligands. In another aspect, the MRD is derived from yeast display or RNA display technology.

The present invention also relates to a method of treating or preventing a disease or disorder in a subject in need thereof, comprising administering an antibody comprising an MRD to the subject. In one aspect, the disease is cancer. In another aspect, undesired angiogenesis in inhibited. In another aspect, angiogenesis is modulated. In yet another aspect, tumor growth is inhibited.

Certain embodiments provide for methods of treating or preventing a disease, disorder, or injury comprising administering a therapeutically effective amount of an antibody comprising an MRD (i.e. MRD-containing antibodies) to a subject in need thereof. In some embodiments, the disease, disorder or injury is cancer.

In another embodiment, a method of treatment or prevention comprising administering an additional therapeutic agent along with an antibody comprising an MRD is provided. In other embodiments, the methods of treatment or prevention comprise administering an antibody comprising more than one type of MRD.

BRIEF DESCRIPTION OF THE DRAWINGS/FIGURES

DETAILED DESCRIPTION OF THE INVENTION

Figure 1:
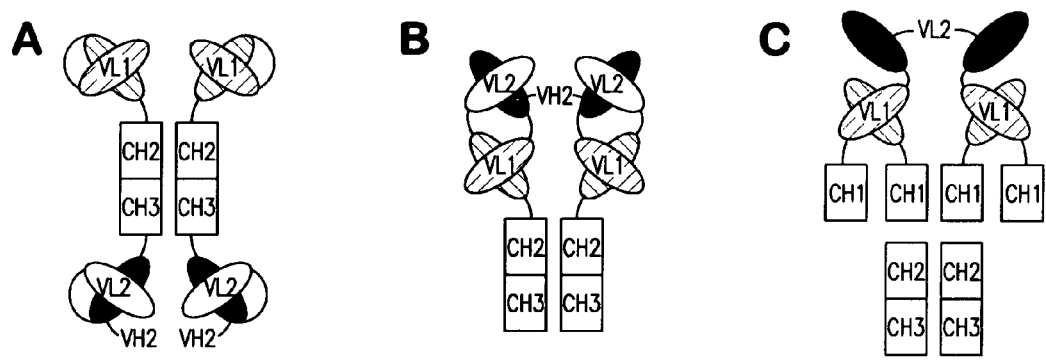
FIG. 1 shows the schematic representation of different designs of multi-specific and multi-valent molecules. MRDs are depicted as triangles, circles, diamonds, and squares.

The following provides a description of antibodies containing at least one modular recognition domain (MRD). The linkage of one or more MRDs to an antibody results in a multi-specific molecule of the invention that retains structural and functional properties of traditional antibodies or Fc optimized antibodies and can readily be synthesized using conventional antibody expression systems and techniques. The antibody can be any suitable antigen-binding immunoglobulin, and the MRDs can be any suitable target-binding peptide. The MRDs can be operably linked to any location on the antibody, and the attachment can be direct or indirect (e.g., through a chemical or polypeptide linker). Compositions of antibodies comprising an MRD, methods of manufacturing antibodies comprising an MRD, and methods of using antibodies comprising MRDs are also described in the sections below.

The section headings used herein are for organizational purposes only and are not to be construed as in any way limiting the subject matter described.

Standard techniques may be used for recombinant DNA molecule, protein, and antibody production, as well as for tissue culture and cell transformation. Enzymatic reactions and purification techniques are typically performed according to the manufacturer's specifications or as commonly accomplished in the art using conventional procedures such as those set forth in Harlow et al., Antibodies: A Laboratory Manual, (Cold Spring Harbor Laboratory Press, 2nd ed. 1988) and Sambrook et al. (Molecular Cloning: A Laboratory Manual. Cold Spring Harbor Laboratory Press, Cold Spring Harbor, N.Y. (1989)) (both herein incorporated by reference), or as described herein. Unless specific definitions are provided, the nomenclature utilized in connection with, and the laboratory procedures and techniques of analytical chemistry, synthetic organic chemistry, and medicinal and pharmaceutical chemistry described herein, are those known and used in the art. Standard techniques may be used for chemical syntheses, chemical analyses, pharmaceutical preparation, formulation, delivery, and treatment of patients.

I. DEFINITIONS

The terms "MRD-containing antibodies," "antibody-MRD molecules," "MRD-antibody molecules," "antibodies comprising an MRD" and "Zybodies" are used interchangeably herein and do not encompass a peptibody. Each of these terms may also be used herein to refer to a "complex" of the invention.

The term "antibody" is used herein to refer to immunoglobulin molecules that are able to bind antigens through an antigen binding domain (i.e., antibody combining site). The term "antibody" includes polyclonal, oligoclonal (mixtures of antibodies), and monoclonal antibodies, chimeric, single chain, and humanized antibodies. The term "antibody" also includes human antibodies. In some embodiments, an antibody comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains: CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. In other embodiments, the antibody is a homomeric heavy chain antibody (e.g., camelid antibodies) which lacks the first constant region domain (CH1) but retains an otherwise intact heavy chain and is able to bind antigens through an antigen binding domain. The variable regions of the heavy and light chains in the antibody-MRD fusions of the invention contain a functional binding domain that interacts with an antigen.

The term "monoclonal antibody" typically refers to a population of antibody molecules that contain only one species of antibody combining site capable of immunoreacting with a particular epitope. A monoclonal antibody thus typically displays a single binding affinity for any epitope with which it immunoreacts. As used herein, a "monoclonal antibody" may also contain an antibody molecule having a plurality of antibody combining sites (i.e., a plurality of variable domains), each immunospecific for a different epitope, e.g., a bispecific monoclonal antibody. Thus, as used herein, a "monoclonal antibody" refers to a homogeneous antibody population involved in the highly specific recognition and binding of one or two (in the case of a bispecific monoclonal antibody) antigenic determinants, or epitopes. This is in contrast to polyclonal antibodies that typically include different antibodies directed against different antigenic determinants. The term "monoclonal antibody" refers to such antibodies made in any number of manners including but not limited to by hybridoma, phage selection, recombinant expression, yeast, and transgenic animals.

A "dual-specific antibody" is used herein to refer to an immunoglobulin molecule that contains dual-variable-domain immunoglobulins, where the dual-variable-domain can be engineered from any two monoclonal antibodies.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity and/or affinity while the constant regions are homologous to the sequences in antibodies derived from another species (usually human) to avoid eliciting an immune response in that species.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementarity determining region (CDR) are replaced by residues from the CDR of a non-human species (e.g., mouse, rat, rabbit, hamster) that have the desired specificity and/or affinity (Jones et al., Nature, 321:522-525 (1986); Riechmann et al., Nature, 332:323-327 (1988); Verhoeyen et al., Science, 239: 1534-1536 (1988)). In some instances, the Fv framework region (FR) residues of a human immunoglobulin are replaced with the corresponding residues in an antibody from a non-human species that has the desired specificity and/or affinity. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise an immunoglobulin constant region or domain (Fe), typically that of a human immunoglobulin. Examples of methods used to generate humanized antibodies are described in U.S. Pat. No. 5,225, 539, U.S. Pat. No. 4,816,567, Morrison, Science 229:1202 (1985); Oi et al., BioTechniques 4:214 (1986); Cabilly et al., Taniguchi et al., EP 171496; Morrison et al., EP 173494; Neuberger et al., WO 86/01533; Robinson et al., WO 8702671; Boulianne et al., Nature 312:643 (1984); and Neuberger et al., Nature 314:268 (1985) which are herein incorporated by reference.

As used herein, "human" antibodies include antibodies having the amino acid sequence of a human immunoglobulin or one or more human germlines and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al. A human antibody may still be considered "human" even if amino acid substitutions are made in the antibody. Examples of methods used to generate human antibodies are described in: PCT publications WO 98/24893, WO 92/01047, WO 96/34096, and WO 96/33735; European Patent No. 0 598 877; U.S. Pat. Nos. 5,413,923, 5,625,126, 5,633,425, 5,569,825, 5,661,016, 5,545,806, 5,814,318, 5,885,793, 5,916,771, and 5,939,598; and Lonberg and Huszar, Int. Rev. Immunol. 13:65-93 (1995), which are herein incorporated by reference.

An "antibody combining site" is that structural portion of an antibody molecule comprised of heavy and light chain variable and hypervariable regions that specifically binds (immunoreacts with) an antigen. The term "immunoreact" in its various forms means specific binding between an antigenic determinant-containing molecule and a molecule containing an antibody combining site such as a whole antibody molecule or a portion thereof.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain (i.e., antibody combining site) formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196:901-917 (1987), which are herein incorporated by reference). "Humanized antibody" or "chimeric antibody" includes antibodies in which CDR sequences derived from the germline of another mammalian species, such as a mouse, have been grafted onto human framework sequences.

The term "peptibody" refers to a peptide or polypeptide which comprises less than a complete, intact antibody. A peptibody can be an antibody Fc domain attached to at least one peptide. A peptibody does not include antibody variable regions, an antibody combining site, CH1 domains, or Ig light chain constant region domains.

The term "naturally occurring" when used in connection with biological materials such as a nucleic acid molecules, polypeptides, host cells, and the like refers to those which are found in nature and not modified by a human being.

The term "domain" as used herein refers to a part of a molecule or structure that shares common physical or chemical features, for example hydrophobic, polar, globular, helical domains or properties, e.g., a protein binding domain, a DNA binding domain or an ATP binding domain. Domains can be identified by their homology to conserved structural or functional motifs.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence to the antigen(s) to which the polypeptide or antibody binds. Methods of identifying nucleotide and amino acid conservative substitutions and non-conservative substitutions which do not eliminate polypeptide or antigen binding are well-known in the art (see, e.g., Brummell et al., Biochem. 32:1180-1187 (1993); Kobayashi et al., Protein Eng. 12(10): 879-884 (1999); and Burks et al., Proc. Natl. Acad. Sci. USA 94:412-417 (1997)).

A "modular recognition domain" (MRD) or "target binding peptide" is a molecule, such as a protein, glycoprotein and the like, that can specifically (non-randomly) bind to a target molecule. The amino acid sequence of a MRD can typically tolerate some degree of variability and still retain a degree of capacity to bind the target molecule. Furthermore, changes in the sequence can result in changes in the binding specificity and in the binding constant between a preselected target molecule and the binding site. In one embodiment, the MRD is an agonist of the target it binds. An MRD agonist refers to a MRD that in some way increases or enhances the biological activity of the MRD's target protein or has biological activity comparable to a known agonist of the MRD's target protein. In another embodiment, the MRD is an antagonist of the target it binds. An MRD antagonist refers to an MRD that blocks or in some way interferes with the biological activity of the MRD's target protein or has biological activity comparable to a known antagonist or inhibitor of the MRD's target protein.

"Cell surface receptor" refers to molecules and complexes of molecules capable of receiving a signal and the transmission of such a signal across the plasma membrane of a cell. An example of a cell surface receptor of the present invention is an activated integrin receptor, for example, an activated αvβ3 integrin receptor on a metastatic cell. As used herein, "cell surface receptor" also includes a molecule expressed on a cell surface that is capable of being bound by an MRD containing antibody of the invention.

As used herein, a "target binding site" or "target site" is any known, or yet to be defined, amino acid sequence having the ability to selectively bind a preselected agent. Exemplary reference target sites are derived from the RGD-dependent integrin ligands, namely fibronectin, fibrinogen, vitronectin, von Willebrand factor and the like, from cellular receptors such as ErbB2, VEGF, vascular homing peptide or angiogenic cytokines, from protein hormones receptors such as insulin-like growth factor-I receptor, epidermal growth factor receptor and the like, and from tumor antigens.

The term "epitope" or "antigenic determinant" are used interchangeably herein and refer to that portion of any molecule capable of being recognized and specifically bound by a particular binding agent (e.g., an antibody or an MRD). When the recognized molecule is a polypeptide, epitopes can be formed from contiguous amino acids and noncontiguous amino acids and/or other chemically active surface groups of molecules (such as carbohydrates) juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

An antibody, MRD, antibody-containing MRD, or other molecule is said to "competitively inhibit" binding of a reference molecule to a given epitope if it binds to that epitope to the extent that it blocks, to some degree, binding of the reference molecule to the epitope. Competitive inhibition may be determined by any method known in the art, for example, competition ELISA assays. As used herein, an antibody, MRD, antibody-containing MRD, or other molecule may be said to competitively inhibit binding of the reference molecule to a given epitope, for example, by at least 90%, at least 80%, at least 70%, at least 60%, or at least 50%.

The term "protein" is defined as a biological polymer comprising units derived from amino acids linked via peptide bonds; a protein can be composed of two or more chains.

A "fusion polypeptide" is a polypeptide comprised of at least two polypeptides and optionally a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature. The two polypeptides may be operably attached directly by a peptide bond or may be linked indirectly through a linker described herein or otherwise known in the art.

The term "operably linked," as used herein, indicates that two molecules are attached so as to each retain functional activity. Two molecules are "operably linked" whether they are attached directly (e.g., a fusion protein) or indirectly (e.g., via a linker).

The term "linker" refers to a peptide located between the antibody and the MRD or between two MRDs. Linkers can have from about 1 to 20 amino acids, about 2 to 20 amino acids, or about 4 to 15 amino acids. One or more of these amino acids may be glycosylated, as is well understood by those in the art. In one embodiment, the 1 to 20 amino acids are selected from glycine, alanine, proline, asparagine, glutamine, and lysine. In another embodiment, a linker is made up of a majority of amino acids that are sterically unhindered, such as glycine and alanine. Thus, in some embodiments, the linker is selected from polyglycines (such as $(Gly)_5$, and $(Gly)_8$), poly(Gly-Ala), and polyalanines. The linker can also be a non-peptide linker such as an alkyl linker, or a PEG linker. For example, alkyl linkers such as —NH—$(CH_2)_s$—C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. An exemplary non-peptide linker is a PEG linker. In certain embodiments, the PEG linker has a molecular weight of about 100 to 5000 kDa, or about 100 to 500 kDa. The peptide linkers may be altered to form derivatives.

"Target cell" refers to any cell in a subject (e.g., a human or animal) that can be targeted by an antibody-containing MRD or MRD of the invention. The target cell can be a cell expressing or overexpressing the target binding site, such as an activated integrin receptor.

"Patient," "subject," "animal" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles. In some embodiments, the patient is a human.

"Treating" or "treatment" includes the administration of the antibody comprising an MRD of the present invention to prevent or delay the onset of the symptoms, complications, or biochemical indicia of a disease, condition, or disorder, alleviating the symptoms or arresting or inhibiting further development of the disease, condition, or disorder. Treatment can be prophylactic (to prevent or delay the onset of the disease, or to prevent the manifestation of clinical or subclinical symptoms thereof) or therapeutic suppression or alleviation of symptoms after the manifestation of the disease, condition, or disorder. Treatment can be with the antibody-MRD composition alone, the MRD alone, or in combination of either with an additional therapeutic agent.

As used herein, the terms "pharmaceutically acceptable," or "physiologically tolerable" and grammatical variations thereof, as they refer to compositions, carriers, diluents and reagents, are used interchangeably and represent that the materials are capable of administration to or upon a human without the production of therapeutically prohibitive undesirable physiological effects such as nausea, dizziness, gastric upset and the like.

"Modulate," means adjustment or regulation of amplitude, frequency, degree, or activity. In another related aspect, such modulation may be positively modulated (e.g., an increase in frequency, degree, or activity) or negatively modulated (e.g., a decrease in frequency, degree, or activity).

"Cancer," "tumor," or "malignancy" are used as synonymous terms and refer to any of a number of diseases that are characterized by uncontrolled, abnormal proliferation of cells, the ability of affected cells to spread locally or through the bloodstream and lymphatic system to other parts of the body (metastasize) as well as any of a number of characteristic structural and/or molecular features. A "cancerous tumor," or "malignant cell" is understood as a cell having specific structural properties, lacking differentiation and being capable of invasion and metastasis. Examples of cancers that may be treated using the antibody-MRD fusions of the invention include breast, lung, brain, bone, liver, kidney, colon, head and neck, ovarian, hematopoietic (e.g., leukemia), and prostate cancer. Other types of cancer and tumors that may be treated using MRD-containing antibodies are described herein or otherwise known in the art.

An "effective amount" of an antibody, MRD, or MRD-containing antibody as disclosed herein is an amount sufficient to carry out a specifically stated purpose such as to bring about an observable change in the level of one or more biological activities related to the target to which the antibody, MRD, or MRD-containing antibody binds. In certain embodiments, the change increases the level of target activity. In other embodiments, the change decreases the level of target activity. An "effective amount" can be determined empirically and in a routine manner, in relation to the stated purpose.

The term "therapeutically effective amount" refers to an amount of an antibody, MRD, MRD-containing antibody, or other drug effective to "treat" a disease or disorder in a subject or mammal. In the case of cancer, the therapeutically effective amount of the drug can reduce angiogenesis and neovascularization; reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth or tumor incidence; stimulate immune responses against cancer cells and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

II. MODULAR RECOGNITION DOMAINS (MRDS)

The present invention describes an approach based on the adaptation of target binding peptides or modular recognition domains (MRDs) as fusions to catalytic or non-catalytic antibodies.

In certain embodiments, where the antibody component of the MRD-antibody fusion is a catalytic antibody, the MRD-antibody fusions provide for effective targeting to tumor cells or soluble molecules while leaving the prodrug activation capability of the catalytic antibody intact. MRDs can also extend the binding capacity of non-catalytic antibodies providing for an effective approach to extend the binding functionality of antibodies, particularly for therapeutic purposes.

One aspect of the present invention relates to development of a full-length antibody comprising at least one modular recognition domain (MRD). In another non-exclusive embodiment, the full-length antibody comprises more than one MRD, wherein the MRDs have the same or different specificities. In addition, a single MRD may be comprised of a tandem repeat of the same or different amino acid sequence that can allow for the binding of a single MRD to multiple targets.

The interaction between a protein ligand and its target receptor site often takes place at a relatively large interface. However, only a few key residues at the interface contribute to most of the binding. The MRDs can mimic ligand binding. In certain embodiments, the MRD can mimic the biological activity of a ligand (an agonist MRD) or through competitive binding inhibit the bioactivity of the ligand (an antagonist MRD). MRDs in MRD-containing antibodies can also affect targets in other ways, e.g., by neutralizing, blocking, stabilizing, aggregating, or crosslinking the MRD target.

It is contemplated that MRDs of the present invention will generally contain a peptide sequence that binds to target sites of interests and have a length of about 2 to 150 amino acids, about 2 to 125 amino acids, about 2 to 100 amino acids, about 2 to 90 amino acids, about 2 to 80 amino acids, about 2 to 70 amino acids, about 2 to 60 amino acids, about 2 to 50 amino acids, about 2 to 40 amino acids, about 2 to 30 amino acids, or about 2 to 20 amino acids. It is also contemplated that MRDs have a length of about 10 to 150 amino acids, about 10 to 125 amino acids, about 10 to 100 amino acids, about 10 to 90 amino acids, about 10 to 80 amino acids, about 10 to 70 amino acids, about 10 to 60 amino acids, about 10 to 50 amino acids, about 10 to 40 amino acids, about 10 to 30 amino acids, or about 10 to 20 amino acids. It is further contemplated that MRDs have a length of about 20 to 150 amino acids, about 20 to 125 ammo acids, about 20 to 100 amino acids, about 20 to 90 amino acids, about 20 to 80 amino acids, about 20 to 70 amino acids, about 20 to 60 amino acids, about 20 to 50 amino acids, about 20 to 40 amino acids, or about 20 to 30 amino acids. In certain embodiments, the MRDs have a length of about 2 to 60 amino acids. In other embodiments, the MRDs have a length of about 10 to 60 amino acids. In other embodiments, the MRDs have a length of about 10 to 50 amino acids. In additional embodiments, the MRDs have a length of about 10 to 40 amino acids. In additional embodiments, the MRDs have a length of about 10 to 30 amino acids.

In nonexclusive embodiments, the MRD does not contain an antigen binding domain, or another antibody domain such as a constant region, a variable region, a complementarity determining region (CDR), a framework region, an Fc domain, or a hinge region. In one non-exclusive embodiment, the MRD does not contain an antigen binding domain. In another non-exclusive embodiment, the MRD does not contain three CDRs. In another non-exclusive embodiment, the MRD does not contain CDR1 and CDR2. In yet another non-exclusive embodiment, the MRD does not contain CDR1. In one nonexclusive embodiment, the MRD is not derived from a natural cellular ligand. In another nonexclusive embodiment, the MRD is not a radioisotope. In another nonexclusive embodiment, the MRD is not a protein expression marker such as glutathione S-transferase (GST), His-tag, Flag, hemagglutinin (HA), MYC or a fluorescent protein (e.g., GFP or RFP). In another nonexclusive embodiment, the MRD does not bind serum albumin. In an additional nonexclusive embodiment, the MRD is not a small molecule that is a cytotoxin. It yet another nonexclusive embodiment, the MRD does not have enzymatic activity. In another non-exclusive embodiment, the MRD has a therapeutic effect when administered alone and/or when fused to an Fc in a patient or animal model. In another non-exclusive embodiment, the MRD has a therapeutic effect when repeatedly administered alone and/or when fused to an Fc in a patient or animal model (e.g., 3 or more times over the course of at least six months).

In some embodiments, the MRD is conformationally constrained. In other embodiments, the MRD is not conformationally constrained.

In some particular embodiments, the MRD has a particular hydrophobicity. For example, the hydrophobicity of MRDs can be compared on the basis of retention times determined using hydrophobic interaction chromatography or reverse phase liquid chromatography.

The MRD target can be any molecule that it is desirable for an MRD-containing antibody to interact with. For example, the MRD target can be a soluble factor or a transmembrane protein, such as a cell surface receptor. In certain non-exclusive embodiments, the MRD target is a factor that regulates cell proliferation, differentiation, or survival. In other nonexclusive embodiments, the MRD target is a cytokine. In another nonexclusive embodiment, the MRD target is a factor that regulates angiogenesis.

The MRDs are able to bind their respective target when the MRDs are attached to an antibody. In some embodiments, the MRD is able to bind its target when not attached to an antibody.

The sequence of the MRD can be determined several ways. For example, MRD sequences can be derived from natural ligands or known sequences that bind to a specific target binding site. Additionally, phage display technologies have emerged as a powerful method in identifying peptides which bind to target receptors and ligands. In peptide phage display libraries, naturally occurring and non-naturally occurring (e.g., random peptide) sequences can be displayed by fusion with coat proteins of filamentous phage. The methods for elucidating binding sites on polypeptides using phage display vectors has been previously described, in particular in WO 94/18221, which is herein incorporated by reference. The methods generally involve the use of a filamentous phage (phagemid) surface expression vector system for cloning and expressing polypeptides that bind to the pre-selected target site of interest.

The methods of the present invention for preparing MRDs include the use of phage display vectors for their particular advantage of providing a means to screen a very large population of expressed display proteins and thereby locate one or more specific clones that code for a desired target binding reactivity.

Variants and derivatives of the MRDs that retain the ability to bind the target antigen are included within the scope of the present invention. Included within variants are insertional, deletional, and substitutional variants, as well as variants that include MRDs presented herein with additional amino acids at the N- and/or C-terminus, including from about 0 to 50, 0 to 40, 0 to 30, 0 to 20 amino acids and the like. It is understood that a particular MRD of the present invention may be modified to contain one, two, or all three types of variants. Insertional and substitutional variants may contain natural amino acids, unconventional amino acids, or both. In some embodiments, the MRD contains a sequence with no more than 1, 2, 3, 4, 5, 6, 7, 8, 9, 10, 15, or 20 amino acid differences when compared to an MRD sequence described herein. In some embodiments, the amino acid differences are substitutions. These substitutions can be conservative or non-conservative in nature and can include unconventional or non-natural amino acids.

The ability of an MRD to bind its target can be assessed using any technique that assesses molecular interaction. For example, MRD-target interaction can be assayed as described in the Examples below or alternatively, using in vitro or in vivo binding assays such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC). Assays evaluating the ability of an MRD to functionally affect it's target (e.g., assays to measure signaling, proliferation, migration etc.) can also be used to indirectly assess MRD-target interaction.

Once the sequence of the MRD has been elucidated, the peptides may be prepared by any of the methods known in the art. For example, the MRD peptides can be chemically synthesized and operably attached to the antibody or can be synthesized using recombinant technology. For example, MRDs can be synthesized in solution or on a solid support using known techniques. Various automatic synthesizers are commercially available and can be used in accordance with known protocols. See, for example, Tam et al., J. Am. Chem. Soc., 105:6442 (1983); Merrifield, Science 232:341-347 (1986); Barany and Merrifield, The Peptides, Gross and Meienhofer, eds, Academic Press, New York, 1-284; Barany et al., Int. J. Pep. Protein Res., 30:705 739 (1987); and U.S. Pat. No. 5,424,398, which are herein incorporated by reference.

The following MRD targets are described in more detail by way of example only.

In some embodiments described herein, the MRD targets an integrin. The role of integrins such as $\alpha v\beta 3$ and $\alpha v\beta 5$ as tumor-associated markers has been well documented. A recent study of 25 permanent human cell lines established from advanced ovarian cancer demonstrated that all lines were positive for $\alpha v\beta 5$ expression and many were positive for $\alpha v\beta 3$ expression. Studies have also shown that $\alpha v\beta 3$ and $\alpha v\beta 5$ is highly expressed on malignant human cervical tumor tissues. Integrins have also demonstrated therapeutic effects in animal models of Kaposi's sarcoma, melanoma, and breast cancer.

A number of integrin $\alpha v\beta 3$ and $\alpha v\beta 5$ antagonists are in clinical development. These include cyclic RGD peptides and synthetic small molecule RGD mimetics. Two antibody-based integrin antagonists are currently in clinical trials for the treatment of cancer. The first is VITAXIN® (MEDI-522, Abegrein), the humanized form of the murine anti-human $\alpha v\beta 3$ antibody LM609. A dose-escalating phase I study in cancer patients demonstrated that VITAXIN® is safe for use in humans. Another antibody in clinical trials is. CNT095, a fully human Ab that recognizes $\alpha v$ integrins. A Phase I study of CNT095 in patients with a variety of solid tumors has shown that it is well tolerated. Cilengitide (EMD 121974), a peptide antagonist of $\alpha v\beta 3$ and $\alpha v\beta 5$, has also proven safe in phase I trials. Furthermore, there have been numerous drug targeting and imaging studies based on the use of ligands for these receptors. These preclinical and clinical observations demonstrate the importance of targeting $\alpha v\beta 3$ and $\alpha v\beta 5$ and studies involving the use of antibodies in this strategy have consistently reported that targeting through these integrins is safe.

Integrin-binding MRDs containing one more RGD tripeptide sequence motifs represent an example of MRDs of the invention. Ligands having the RGD motif as a minimum recognition domain and from which MRDs of the invention can be derived are well known, a partial list of which includes, with the corresponding integrin target in parenthesis, fibronectin (α3β1, α5β1, αvβ1, α11bβ3, αvβ3, and α3β1) fibrinogen (αMβ2 and α11bβ1) von Willebrand factor (α11bβ3 and αvβ3), and vitronectin (α11bβ3, αvβ3 and αvβ5).

In one embodiment, the RGD containing targeting MRD is a member selected from the group consisting of: YCRGDCT (SEQ ID NO:3); PCRGDCL (SEQ ID NO:4); TCRGDCY (SEQ ID NO:5); and LCRGDCF (SEQ ID NO:6).

A MRD that mimics a non-RGD-dependent binding site on an integrin receptor and having the target binding specificity of a high affinity ligand that recognizes the selected integrin is also contemplated in the present invention. MRDs that bind to an integrin receptor and disrupt binding and/or signaling activity of the integrin are also contemplated.

In some embodiments, the MRD targets an angiogenic molecule. Angiogenesis is essential to many physiological and pathological processes. Ang2 has been shown to act as a proangiogenic molecule. Administration of Ang2-selective inhibitors is sufficient to suppress both tumor angiogenesis and corneal angiogenesis. Therefore, Ang2 inhibition alone or in combination with inhibition of other angiogenic factors, such as VEGF, can represent an effective antiangiogenic strategy for treating patients with solid tumors.

It is contemplated that MRDs useful in the present invention include those that bind to angiogenic receptors, angiogenic factors, and/or Ang2. In a specific embodiment, an MRD of the invention binds Ang2. In one embodiment, the angiogenic cytokine targeting MRD sequences or MRD-containing sequences contain a sequence selected from the group: MGAQTNFMPMDDLEQRLY EQFILQQGLE (SEQ ID NO:7); MGAQTNFMPMD NDELLLYEQ-FILQQGLE (SEQ ID NO:8); MGAQTNFMPMDAT ETR-LYEQFILQQGLE (SEQ ID NO:9); AQQEECEWDPWT-CEHMGSGSATGGSGSTASSGSGSATHQEECEWDPW TCEHMLE (SEQ ID NO:10) (2xCon4); MGAQTNFMPM-DNDELLNYEQFI LQQGLE (SEQ ID NO:11); and PXDNDXLLNY (SEQ ID NO:12) where X is one of the 20 naturally-occurring amino acids.

In another embodiment, the angiogenic cytokine targeting MRD sequences or MRD-containing sequences contain a sequence selected from the group: MGAQTNFMPMDN-DELLLYEQFILQQGLEGGSG-
STASSGSGSSLGAQTNFM PMDNDELLLY (SEQ ID NO:20); AQQEECEWDPWTCEH MGSGSATGGSG-STASSGSGSATHQEECEWDPWTCEHMLE (SEQ ID NO:10); AQQEECEFAPWTCEHM (SEQ ID NO:21) (ConFA); core nEFAPWTn (SEQ ID NO:22) where n is from about 0 to 50 amino acid residues; AQQEECEFAPWTCEH-MGSGSATGGSGSTASSGSGSATHQ EECEFAPWTCEH-MLE (SEQ ID NO:23) (2xConFA); and AQQEECELAPWT-CEHM (SEQ ID NO:24) (ConLA).

In another embodiment, the angiogenic cytokine targeting MRD sequences or MRD-containing sequences contain a sequence selected from the group:
XnELAPWTXn where n is from about 0 to 50 amino acid residues and X is any amino acid (SEQ ID NO:25); AQQEECELAPWTCEHMGSGSATGGS GSTASSGSG-SATHQEECELAPWTCEHMLE (SEQ ID NO:26) (2xConLA); AQQEECEFSPWTC EHM (SEQ ID NO:27) (ConFS); XnEFSPWTXn where n is from about 0 to 50 amino acid residues and X is any amino acid (SEQ ID NO:28); AQQEECEFSPWTCEHMGSGSATGGSG-STASSGSGSATHQEECEFSPWT CEHMLE (SEQ ID NO:29) (2xConFS); AQQEECELEPWTCEHM (SEQ ID NO:30) (ConLE); XnELEPWTXn where n is from about 0 to 50 amino acid residues (SEQ ID NO:31) and wherein X is any amino acid; and AQQEECELEPWTCEHMGSGSATGGSG-STASSGSGSATHQEECELEPWTCE HMLE (SEQ ID NO:32) (2xConLE).

It should be understood that such the MRDs of the invention can be present in tandem dimers, trimers or other multimers either homologous or heterologous in nature. For example, one can dimerize identical Con-based sequences such as in 2xConFA to provide a homologous dimer, or the Con peptides can be mixed such that ConFA is combined with ConLA to create ConFA-LA heterodimer with the sequence:

```
                                        (SEQ ID NO: 33)
AQQEECEFAPWTCEHMGSGSATGGSGSTASSGSGSATHQEECE

LAPWTCEHMLE.
```

Another heterodimer of the invention is ConFA combined with ConFS to create ConFA-FS with the sequence: AQQEECEFAPW TCEHMGSGSATGGSGSTASSGSG-SATHQEECEFSPWTCEHMLE (SEQ ID NO:34).

One of skill in the art, given the teachings herein, will appreciate that other such combinations will create functional Ang2 binding MRDs as described herein.

The invention also includes human Ang2 MRDs having a core sequence selected from: XnEFAPWTXn where n is from about 0 to 50 amino acid residues (SEQ ID NO:22); XnE-LAPWTXn where n is from about 0 to 50 amino acid residues (SEQ ID NO:25); XnEFSPWTXn where n is from about 0 to 50 amino acid residues (SEQ ID NO:28); XnELEPWTXn where n is from about 0 to 50 amino acid residues (SEQ ID NO:31); and Xn AQQEECEX$_1$X$_2$PWTCEHMXn where n is from about 0 to 50 amino acid residues and X represents any natural amino acid (SEQ ID NO:57).

In some embodiments, the MRD targets vascular endothelial growth factor (VEGF). Phage display selections and structural studies of VEGF neutralizing peptides in complex with VEGF have been reported. These studies have revealed that peptide vl 14 (VEPNCDIHVMWEWECFERL) (SEQ ID NO:13) is VEGF specific, binds VEGF with 0.2 μM affinity, and neutralizes VEGF-induced proliferation of Human Umbilical Vein Endothelial Cells (HUVEC). Since VEGF is a homodimer, the peptide occupies two identical sites at either end of the VEGF homodimer. In a specific embodiment, the antibody-MRD fusion of the invention comprises vl14. In other embodiments, the antibody-MRD fusion comprises variants/derivatives that competitively inhibit the ability of the antiboby-vl14 fusion to bind to VEGF. In additional embodiments, an anti-VEGF antibody containing an MRD that targets VEGF is contemplated in the present invention. Anti-VEGF antibodies can be found for example in Presta et al., Cancer Research 57:4593-4599, (1997); and Fuh et al., J Biol Chem 281:10 6625, (2006), which are herein incorporated by reference.

Insulin-like growth factor-I receptor-specific MRDs can also be used in the present invention. In one embodiment, the MRD sequence that targets the insulin-like growth factor-I receptor is SFYSCLESLVNGPAEKSRGQWDGCRKK (SEQ ID NO:14).

In one aspect, the invention includes an IGF1R binding MRD having the sequence: NFYQCIXIX2LX3X4X5PAEKSRGQWQECRTGG (SEQ ID NO:58), wherein X1 is E or D; X2 is any amino acid; X3 is any amino acid; X4 is any amino acid and X5 is any amino acid.

In another embodiment, the IGF1R binding MRD contains a sequence selected from the group: NFYQCIEMLASHPAEKSRGQWQECRTGG (SEQ ID NO:35); NFYQCIEQLALRPAEKSRGQWQECRTGG (SEQ ID NO:36); NFYQCIDLLMAYPAEKS RGQWQECRTGG (SEQ ID NO:37); NFYQCIERLVTGPAEKSRGQWQECRTGG (SEQ ID NO:38); NFYQCIEYLAMKPAEKSRGQWQECRTGG (SEQ ID NO:39); and NFYQCIEALQSRPAEKSRGQWQECRTGG (SEQ ID NO:40).

In another embodiment, the IGF1R binding MRD contains a sequence selected from the group: NFYQCIEALSRSPAEKSRGQWQECRTGG (SEQ ID NO:41); NFYQCIEHLSGSPAEKSRGQWQECRTG (SEQ ID NO:42); NFYQCIESLAGGPAEKSRGQ WQECRTG (SEQ ID NO:43); NFYQCIEALVGVPAEKSRGQWQECRTG (SEQ ID NO:44); and NFYQCIEMLSLPPAEKSRGQWQECRTG (SEQ ID NO:45).

In another embodiment, the IGF1R binding MRD contains a sequence selected from the group: NFYQCIEVFWGRPAEKSRGQWQECRTG (SEQ ID NO:46); NFYQCIEQLSSGPAEKSRGQWQECRTG (SEQ ID NO:47); NFYQCIELLSARPAEKSRGQ WAECRAG (SEQ ID NO:48); and NFYQCIEALARTPAEKSRGQWVECRAP (SEQ ID NO:49).

Vascular homing-specific MRDs are also contemplated for use in the present invention. A number of studies have characterized the efficacy of linking the vascular homing peptide to other proteins like IL-12 or drugs to direct their delivery in live animals. One example of an MRD sequence that is a vascular homing peptide that is envisioned to be included within an antibody-MRD fusion of the invention is ACDCRGDCFCG (SEQ ID NO:15).

Numerous other target binding sites are contemplated as being the target of the antibody-MRD fusions of the present invention, including for example, epidermal growth factor receptor (EGFR), CD20, tumor antigens, ErbB2, ErbB3, ErbB4, insulin-like growth factor-I receptor, nerve growth factor (NGR), hepatocyte growth factor receptor, and tumor-associated surface antigen epithelial cell adhesion molecule (Ep-CAM). MRDs can be directed towards these target binding sites.

In one embodiment, the MRD sequence that binds to EGFR and that is envisioned to be included within an antibody-MRD fusion is selected from the group:

```
                                      (SEQ ID NO: 16)
VDNKFNKELEKAYNEIRNLPNLNGWQMTAFIASLVDDPSQSA

NLLAEAKKLNDAQAPK;
and
                                      (SEQ ID NO: 17)
VDNKFNKEMWIAWEEIRNLPNLNGWQMTAFIASLVDDPSQSA

NLLAEAKKLNDAQAPK
```

In another embodiment, the MRD binds ErbB2 and has the sequence:

```
                                      (SEQ ID NO: 18)
VDNKFNKEMRNAYWEIALLPNLNNQQKRAFIRSLYDDPSQSAN

LLAEAKKLNDAQAPK.
```

In some embodiments, the MRD binds to a human protein.

III. ANTIBODIES

The antibody in the MRD-containing antibodies described herein can be any suitable antigen-binding immunoglobulin. In certain embodiments, the MRD-containing antibody molecules described herein retain the structural and functional properties of traditional monoclonal antibodies. Thus, the antibodies retain their epitope binding properties, but advantageously also incorporate one or more additional target-binding specificities.

Antibodies that can be used in the MRD-containing antibodies include, but are not limited to, monoclonal, multispecific, human, humanized, and chimeric antibodies. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. In specific embodiments, the antibodies are IgG1. In other specific embodiments, the antibodies are IgG3.

Antibodies that can be used as part of the MRD-containing antibodies can be naturally derived or the result of recombinant engineering (e.g., phage display, xenomouse, and synthetic). In specific embodiments, the antibodies are human.

In certain embodiments, the heavy chain portions of one polypeptide chain of a multimer are identical to those on a second polypeptide chain of the multimer. In alternative embodiments, the heavy chain portion-containing monomers of the invention are not identical. For example, each monomer may comprise a different target binding site, forming, for example, a bispecific antibody.

Bispecific, bivalent antibodies, and methods of making them, are described, for instance in U.S. Pat. Nos. 5,731,168; 5,807,706; 5,821,333; and U.S. Appl. Publ. Nos. 2003/020734 and 2002/0155537, which are herein incorporated by reference. Bispecific tetravalent antibodies, and methods of making them are described, for instance, in WO 02/096948 and WO 00/44788, the disclosures of both of which are herein incorporated by reference. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992).

Affinity maturation strategies and chain shuffling strategies (see, e.g., Marks et al., Bio/Technology 10:779-783 (1992), which is herein incorporated by reference) are known in the art and can be employed to generate high affinity antibodies that can be used in the MRD-containing antibodies described herein.

In certain embodiments, the MRD-containing antibodies have been modified so as to not elicit a deleterious immune response in the animal to be treated, e.g., in a human. In one embodiment, the antibody is modified to reduce immunogenicity using art-recognized techniques. For example, antibody components of the MRD-containing antibodies can be humanized, deimmunized, or chimerized. These types of antibodies are derived from a non-human antibody, typically a murine antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into human frameworks and constant regions with or without retention of critical framework residues; or (c) transplanting the entire non-human variable domains, but "cloaking" them with human-like sections by replacement of surface residues. Such methods are disclosed in Morrison et al., Proc. Natl. Acad. Sci. 81:6851-6855 (1984); Morrison et al., Adv. Immunol. 44:65-92 (1988); Verhoeyen et al., Science 239:1534-1536 (1988); Padlan, Molec. Immun. 28:489-498 (1991); Padlan, Molec. Immun. 31:169-217 (1994), and U.S. Pat. Nos. 5,585,089, 5,693,761, 5,693,762, and 6,190,370, all of which are herein incorporated by reference.

Many different antibody components of the MRD-containing antibodies can be used in the methods described herein. It is contemplated that catalytic and non-catalytic antibodies can be used in the present invention. For example, Antibody 38C2 is an antibody-secreting hybridoma and has been previously described in WO 97/21803. 38C2 contains an antibody combining site that catalyzes the aldol addition reaction between an aliphatic donor and an aldehyde acceptor. In a syngeneic mouse model of neuroblastoma, systemic administration of an etoposide prodrug and intra-tumor injection of Ab 38C2 inhibited tumor growth.

The antibody target of the MRD-containing antibody (i.e., the target of the antigenic binding domain) can be any molecule that it is desirable for a MRD-antibody fusion to interact with. For example, the antibody target can be a soluble factor or the antibody target can be a transmembrane protein, such as a cell surface receptor. The antibody target can also be an extracellular component. In certain nonexclusive embodiments, the antibody target is a factor that regulates cell proliferation, differentiation, or survival. In another nonexclusive embodiment, the antibody target is a cytokine. In another nonexclusive embodiment, the antibody target is a factor that regulates angiogenesis. In another nonexclusive embodiment, the antibody target is a factor that regulates cellular adhesion and/or cell-cell interaction. In certain nonexclusive embodiments, the antibody target is a cell signaling molecule. The ability of an antibody to bind to a target and to block, increase, or interfere with the biological activity of the antibody target can be determined using or routinely modifying assays, bioassays, and/or animal models known in the art for evaluating such activity.

In some embodiments, the antibody target of the MRD-containing antibody is a target that has been validated in an animal model or clinical setting.

In other embodiments, the antibody target of the MRD-containing antibody is a cancer antigen.

In certain embodiments, the antibody target of the MRD-containing antibody is EGFR, ErbB2, ErbB3, ErbB4, CD20, insulin-like growth factor-I receptor, prostate specific membrane antigen, an integrin, or cMet.

In one embodiment, the antibody in the MRD-containing antibody specifically binds EGFR. In a specific embodiment, the antibody is ERBITUX® (IMC-C225). In one embodiment, the antibody binds to the same epitope as ERBITUX®. In another embodiment, the antibody competitively inhibits binding of ERBITUX® to EGFR. In another embodiment, the antibody in the MRD-containing antibody inhibits EGFR dimerization. In another specific embodiment, the antibody is panitumumab (e.g., VECTIBIX®, Amgen). In another embodiment, the antibody binds to the same epitope panitumumab. In another embodiment, the antibody competitively inhibits binding of panitumumab to EGFR.

In one embodiment the MRD-containing antibody specifically binds ErbB2 (Her2). In a specific embodiment, the antibody is trastuzumab (e.g., HERCEPTIN®, Genentech/Roche). In one embodiment, the antibody binds to the same epitope as trastuzumab. In another embodiment, the antibody competitively inhibits binding of trastuzumab to ErbB2.

In other embodiments, the antibody in the MRD-containing antibody specifically binds to ErbB2. In one embodiment, the antibody in the MRD-containing antibody is an antibody that specifically binds to the same epitope as the anti-ErbB2 antibody trastuzumab (e.g., HERCEPTIN®, Genentech). In another embodiment, the antibody in the MRD-containing antibody is an antibody that competitively inhibits ErbB2 binding by the anti-ErbB2 antibody trastuzumab. In yet another embodiment, the antibody in the MRD-containing antibody is the anti-ErbB2 antibody trastuzumab In some embodiments, the antibody in the MRD-containing antibody comprises the CDRs of the anti-ErbB2 antibody trastuzumab. The CDR, VH, and VL sequences of trastuzumab are provided in Table 1.

TABLE 1

| CDR | Sequence |
| --- | --- |
| VL-CDR1 | RASQDVNTAVAW (SEQ ID NO: 59) |
| VL-CDR2 | SASFLYS (SEQ ID NO: 60) |
| VL-CDR3 | QQHYTTPPT (SEQ ID NO: 61) |
| VH-CDR1 | GRNIKDTYIH (SEQ ID NO: 62) |
| VH-CDR2 | RIYPTNGYTRYADSVKG (SEQ ID NO: 63) |
| VH-CDR3 | WGGDGFYAMDY (SEQ ID NO: 64) |
| VL | DIQMTQSPSSLSASVGDRVTITCRASQDVNTAVAWY QQKPGKAPKLLIYSASFLYSGVPSRFSGSRSGTDFT LTISSLQPEDFATYYCQQHYTTPPTFGQGTKVEIKRT (SEQ ID NO: 65) |
| VH | EVQLVESGGGLVQPGGSLRLSCAASGFNIKDTYIHW VRQAPGKGLEWVARIYPTNGYTRYADSVKGRFTISA DTSKNTAYLQMNSLRAEDTAVYYCSRWGGDGFYAMD YWGQGTLVTVSS (SEQ ID NO: 66) |

In one embodiment the MRD-containing antibody specifically binds ErbB3 (Her3).

In one embodiment the MRD-containing antibody specifically binds VEGFA.

In one embodiment the MRD-containing antibody specifically binds IGF1R.

In one embodiment, the antibody in the MRD-containing antibody specifically binds integrin.

In other specific embodiments, the antibody in the MRD-containing antibody specifically binds VEGF.

In another specific embodiment, the antibody in the MRD-containing antibody is the catalytic antibody 38C2. In another embodiment, the antibody binds to the same epitope as 38C2. In another embodiment, the antibody competitively inhibits 38C2.

Other antibodies of interest include A33 binding antibodies. Human A33 antigen is a transmembrane glycoprotein of the Ig superfamily. The function of the human A33 antigen in normal and malignant colon tissue is not yet known. However, several properties of the A33 antigen suggest that it is a promising target for immunotherapy of colon cancer. These properties include (i) the highly restricted expression pattern of the A33 antigen, (ii) the expression of large amounts of the A33 antigen on colon cancer cells, (iii) the absence of secreted or shed A33 antigen, (iv) the fact that upon binding of antibody A33 to the A33 antigen, antibody A33 is internalized and sequestered in vesicles, and (v) the targeting of antibody A33 to A33 antigen expressing colon cancer in preliminary clinical studies. Fusion of a MRD directed toward A33 to a catalytic or non-catalytic antibody would increase the therapeutic efficacy of A33 targeting antibodies.

In some embodiments, the antibody in the MRD-containing antibody binds to a human target protein.

The antibodies in the MRD-containing antibodies are able to bind their respective targets when the MRDs are attached to the antibody. In certain embodiments, the antibody binds its target independently. In some embodiments, the antibody is a target agonist. In other embodiments, the antibody is a target antagonist.

It is contemplated that the antibodies used in the present invention may be prepared by any method known in the art. For example, antibody molecules and MRD-containing antibodies can be "recombinantly produced," i.e., produced using recombinant DNA technology.

Monoclonal antibodies that can be used as the antibody component of the MRD-containing antibodies can be prepared using hybridoma methods, such as those described by Kohler and Milstein, Nature 256:495 (1975). Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (MA); enzyme-linked immunosorbent assay (ELISA)) can then be propagated either in vitro, for example, using standard methods (Goding, Monoclonal Antibodies: Principles and Practice, Academic Press, 1986) or in vivo, for example, as ascites tumors in an animal. The monoclonal antibodies can then be purified from the culture medium or ascites fluid as described for polyclonal antibodies above.

Alternatively monoclonal antibodies can also be made using recombinant DNA methods, for example, as described in U.S. Pat. No. 4,816,567. For example, in one approach polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. In other approaches, recombinant monoclonal antibodies or antibody fragments having the desired immunoreactivity can be isolated from phage display libraries expressing CDRs of the desired species using techniques known in the art (McCafferty et al., Nature, 348:552-554 (1990); Clackson et al., Nature, 352:624-628 (1991); and Marks et al., J. Mol. Biol., 222:581-597 (1991)).

The polynucleotide(s) encoding a monoclonal antibody can further be modified in a number of different manners, using recombinant DNA technology to generate alternative antibodies. For example, polynucleotide sequences that encode one or more MRDs and optionally linkers, can be operably fused, for example, to the 5' or 3' end of sequence encoding monoclonal antibody sequences. In some embodiments, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. Techniques for site-directed and high-density mutagenesis of the variable region are known in the art and can be used to optimize specificity, affinity, etc. of a monoclonal antibody.

In certain embodiments, the antibody of the MRD-containing antibody is a human antibody. For example, human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., J. Immunol., 147 (1):86-95 (1991); and U.S. Pat. Nos. 5,750, 373 and 6,787,637). In one embodiment, the human antibody can be derived from the "minilocus approach" in which an exogenous Ig locus is mimicked through inclusion of individual genes from the Ig locus (see e.g., U.S. Pat. No. 5,545, 807). Methods of preparing a human antibody from a phage library, and optionally optimizing binding affinity are known in the art and described, for example, in Vaughan et al., Nat. Biotech., 14:309-314 (1996); Sheets et al., Proc. Nat'l. Acad. Sci., 95:6157-6162 (1998); Hoogenboom Nat. Biotechnology 23:1105-1116 (2005); Hoogenboom and Winter, J. Mol. Biol., 227:381 (1991); Persic et al., Gene 187:9-18 (1997); Jostock et al., J. Immunol. Methods 289:65-80 (2004); Marks et al., J. Mol. Biol., 222:581 (1991)); Barbas III, C. F., Kang, A. S., Lerner, R. A. and Benkovic, S. J., Proc. Natl. Acad. Sci. USA, 88:7978-7982 (1991); Barbas III, C. F., Hu, D., Dunlop, N., Sawyer, L., Cababa, D., Hendry, R. M., Nara, P. L. and Burton, D. R., Proc. Natl. Acad. Sci. USA, 91:3809-3813 (1994); Yang, W.-P., Green, K., Pinz-Sweeney, S., Briones, A. T., Burton, D. R., and Barbas III, C. F., J. Mol. Biol., 254:392-403 (1995); and Barbas III, C. F., Bath, J. D., Hoekstra, D. M. and Lerner, R. A. Proc. Natl. Acad. Sci. USA, 89:4457-4461 (1992). Techniques for the generation and use of antibody phage libraries are also described in; U.S. Pat. Nos. 5,545, 807, 5,969,108, 6,172,197, 5,885,793, 6,521,404, 6,544,731, 6,555,313, 6,582,915, 6,593,081, 6,300,064, 6,653,068, 6,706,484, and 7,264,963; and Rothe et al., J. Mol. Bio. 130: 448-54 (2007) (each of which is herein incorporated by reference). Affinity maturation strategies and chain shuffling strategies (Marks et al., Bio/Technology 10:779-783 (1992) (which is herein incorporated by reference) are known in the art and can be employed to generate high affinity human antibodies.

Antibodies can also be made in mice that are transgenic for human immunoglobuin genes or fragments of these genes and that are capable, upon immunization, of producing a broad repertoire of human antibodies in the absence of endogenous immunoglobulin production. This approach is described in: Lonberg, Nat. Biotechnol 23:1117-1125 (2005), Green, Nature Genet. 7:13-21 (1994), and Lonberg, Nature 368:856-859 (1994); U.S. Pat. Nos. 5,545,807, 5,545, 806, 5,569,825, 5,625,126, 5,633,425, 5,661,016, 6,596,541, 7,105,348, and 7,368,334 (each of which is herein incorporated by reference).

IV. LINKERS

MRD-containing antibodies can contain a single linker, multiple linkers, or no linker. Thus, a MRD may be operably attached (linked) to the antibody directly, or operably attached through an optional linker peptide. Similarly, a MRD may be operably attached to one or more MRD(s) directly, or operably attached to one or more MRD(s) through one or more optional linker peptide(s). Linkers can be of any size or composition so long as they are able to operably attach an MRD and an antibody such that the MRD enables the MRD containing antibody to bind the MRD target. In some embodiments, linkers have about 1 to 20 amino acids, about 1 to 15 amino acids, about 1 to 10 amino acids, about 1 to 5 amino acids, about 2 to 20 amino acids, about 2 to 15 amino acids, about 2 to 10 amino acids, or about 2 to 5 amino acids. The linker can also have about 4 to 15 amino acids.

In certain embodiments, the linker peptide contains a short linker peptide with the sequence GGGS (SEQ ID NO:1), a medium linker peptide with the sequence SSGGGGSGGGGGSS (SEQ ID NO:2), or a long linker peptide with the sequence SSGGGGSGGGGGGSSRSS (SEQ ID NO:19). In another embodiment, the MRD is inserted into the fourth loop in the light chain constant region.

Linker optimization can be evaluated using the techniques described in Examples 1-17 and techniques otherwise known in the art. Linkers preferably should not disrupt the ability of an MRD and/or an antibody to bind target molecules.

V. ANTIBODIES CONTAINING MRDS

Using the methods described herein, multi-specificity and greater multi-valency can be achieved through the fusion of MRDs to antibodies.

The MRDs of the MRD-containing antibodies prepared according to the present invention, may be operably linked to an antibody through the peptide's N-terminus or C-terminus. The MRD may be operably linked to the antibody at the C-terminal end of the heavy chain of the antibody, the N-terminal end of the heavy chain of the antibody, the C-terminal end of the light chain of the antibody, or the N-terminal end of the light chain of the antibody. Optimization of the MRD composition, MRD-antibody attachment location and linker composition can be performed using the binding assays described in Examples 1-18 and bioassays and other assays known in the art for the appropriate target related biological activity.

In one embodiment, MRD-containing antibodies contain an MRD operably linked to either the antibody heavy chain, the antibody light chain, or both the heavy and the light chain. In one embodiment an MRD-containing antibody contains at least one MRD linked to one of the antibody chain terminals. In another embodiment, an MRD-containing antibody of the invention contains at least one MRD operably linked to two of the antibody chain terminals. In another embodiment, an MRD-containing antibody contains at least one MRD operably linked to three of the antibody chain terminals. In another embodiment, an MRD-containing antibody contains at least one MRD operably attached to each of the four antibody chain terminals (i.e., the N and C terminals of the light chain and the N and C terminals of the heavy chain).

In certain specific embodiments, the MRD-containing antibody has at least one MRD operably attached to the N-terminus of the light chain. In another specific embodiment, the MRD-containing antibody has at least one MRD operably attached to the N-terminus of the heavy chain. In another specific embodiment, the MRD-containing antibody has at least one MRD operably attached to the C-terminus of the light chain. In another specific embodiment, the MRD-containing antibody has at least one MRD operably attached to the C-terminus of the heavy chain.

An MRD-containing antibody can be "multispecific" (e.g., bispecific, trispecific tetraspecific, pentaspecific or of greater multispecificity). Thus, whether an MRD-containing antibody is "monospecific" or "multispecific," (e.g., bispecific, trispecific, and tetraspecific) refers to the number of different epitopes that the MRD-containing antibody binds. The present invention contemplates the preparation of mono-, bi-, tri-, tetra-, and penta-specific antibodies as well as antibodies of greater multispecificity. In one embodiment, the MRD-containing antibody binds two different epitopes. In an additional embodiment the MRD-containing antibody binds two different epitopes simultaneously. In another embodiment, the MRD-containing antibody binds three different epitopes. In an additional embodiment the MRD-containing antibody binds three different epitopes simultaneously. In another embodiment, the MRD-containing antibody binds four different epitopes. In an additional embodiment the MRD-containing antibody binds four different epitopes simultaneously. In another embodiment, the MRD-containing antibody binds five different epitopes (see, e.g., FIG. 2D). In an additional embodiment the MRD-containing antibody binds five different epitopes simultaneously.

In other embodiments two MRDs of the MRD-containing antibody bind the same antigen. In other embodiments three, four, five, six, seven, eight, nine or ten MRDs of the MRD-containing antibody bind the same antigen. In other embodiments at least two MRDs of the MRD-containing antibody bind the same antigen. In other embodiments at least three, four, five, six, seven, eight, nine or ten MRDs of the MRD-containing antibody bind the same antigen.

In other embodiments, the antibody and one MRD of the MRD-containing antibody bind the same antigen. In other embodiments the antibody and two, three, four, five, six, seven, eight, nine or ten MRDs of the MRD-containing antibody bind the same antigen. In other embodiments, the antibody and at least one MRD of the MRD-containing antibody bind the same antigen. In other embodiments the antibody and at least two, three, four, five, six, seven, eight, nine or ten MRDs of the MRD-containing antibody bind the same antigen.

The present invention also provides for two or more MRDs which are linked to any terminal end of the antibody. Thus, in one non-exclusive embodiment, two, three, four, or more MRDs are operably linked to the N-terminal of the heavy chain. In another non-exclusive embodiment, two, three, four, or more MRDs are operably linked to the N-terminal of the light chain. In another non-exclusive embodiment, two, three, four, or more MRDs are operably linked to the C-terminal of the heavy chain. In another non-exclusive embodiment, two, three, four, or more MRDs are operably linked to the C-terminal of the light chain. It is envisioned that these MRDs can be the same or different. In addition, any combination of MRD number and linkages can be used. For example, two MRDs can be operably linked to the N-terminal of the heavy chain of an antibody which contains one MRD linked to the C-terminal of the light chain. Similarly, three MRDs can be operably linked to the C-terminal of the light chain and two MRDs can be operably linked to the N-terminal of the light chain.

MRD-containing antibodies can contain one, two, three, four, five, six, seven, eight, nine, ten or more than ten MRDs.

Figure 2:
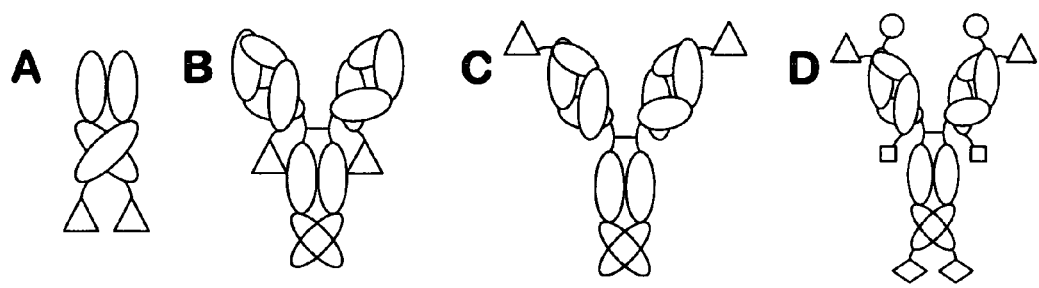
FIG. 2A shows a typical peptibody as a C-terminal fusion with the heavy chain of Fc.
FIG. 2B shows an MRD containing antibody with a C-terminal MRD fusion with the light chain of the antibody.
FIG. 2C shows an MRD containing antibody with an N-terminal MRD fusion with the light chain of the antibody.
FIG. 2D shows an MRD containing antibody with unique MRD peptides fused to each terminus of the antibody.

In one embodiment, the MRD-containing antibody contains one MRD (see, e.g., FIGS. 2B and 2C). In another embodiment, the MRD-containing antibody contains two MRDs. In another embodiment, the MRD-containing antibody contains three MRDs. In another embodiment, the MRD-containing antibody contains four MRDs (see, e.g., FIGS. 2B and 2C). In another embodiment, the MRD-containing antibody contains five MRDs. In another embodiment, the MRD-containing antibody contains six MRDs. In an additional embodiment, the MRD-containing antibody contains between two and ten MRDs.

In one embodiment, the MRD-containing antibody contains at least one MRD. In another embodiment, the MRD-containing antibody contains at least two MRDs. In another embodiment, the MRD-containing antibody contains at least three MRDs. In another embodiment, the MRD-containing antibody contains at least four MRDs. In another embodiment, the MRD-containing antibody contains at least five MRDs. In another embodiment, the MRD-containing antibody contains at least six MRDs.

In another embodiment, the MRD-containing antibody contains two different MRDs. In another embodiment, the MRD-containing antibody contains three different MRDs. In another embodiment, the MRD-containing antibody contains four different MRDs. In another embodiment, the MRD-containing antibody contains five different MRDs. In another embodiment, the MRD-containing antibody contains six different MRDs. In an additional embodiment, the MRD-containing antibody contains between two and ten different MRDs.

In another embodiment, the MRD-containing antibody contains at least two different MRDs. In another embodiment, the MRD-containing antibody contains at least three different MRDs. In another embodiment, the MRD-containing antibody contains at least four different MRDs. In another embodiment, the MRD-containing antibody contains at least five different MRDs. In another embodiment, the MRD-containing antibody contains at least six different MRDs.

Thus, the MRD-containing antibodies can be MRD monomeric (i.e., containing one MRD at the terminus of a peptide chain optionally connected by a linker) or MRD multimeric (i.e., containing more than one MRD in tandem optionally connected by a linker). The multimeric MRD-containing antibodies can be homo-multimeric (i.e., containing more than one of the same MRD in tandem optionally connected by linker(s) (e.g., homodimers, homotrimers, homotetramers etc.)) or hetero-multimeric (i.e., containing two or more MRDs in which there are at least two different MRDs optionally connected by linker(s) where all or some of the MRDs linked to a particular terminus are different (e.g., heterodimer, heterotrimer, heterotetramer etc.)). In one embodiment, the MRD-containing antibody contains two different monomeric MRDs located at different immunoglobulin termini. In another embodiment, the MRD-containing antibody contains three different monomeric MRDs located at different immunoglobulin termini. In another embodiment, the MRD-containing antibody contains four different monomeric MRDs located at different immunoglobulin termini. In another embodiment, the MRD-containing antibody contains five different monomeric MRDs located at different immunoglobulin termini. In another embodiment, the MRD-containing antibody contains six different monomeric MRDs located at different immunoglobulin termini.

In an alternative embodiment, the MRD-containing antibody contains at least one dimeric and one monomeric MRD located at different immunoglobulin termini. In another alternative embodiment, the MRD-containing antibody contains at least one homodimeric and one monomeric MRD located at different immunoglobulin termini. In another alternative embodiment, the MRD-containing antibody contains at least one heterodimeric and one monomeric MRD located at different immunoglobulin termini.

In an alternative embodiment, the MRD-containing antibody contains at least one multimeric and one monomeric MRD located at different immunoglobulin termini. In another alternative embodiment, the MRD-containing antibody contains at least one homomultimeric and one monomeric MRD located at different immunoglobulin termini. In another alternative embodiment, the MRD-containing antibody contains at least one heteromultimeric and one monomeric MRD located at different immunoglobulin termini.

In an alternative embodiment, the MRD-containing antibody contains MRDs operably linked to at least two different immunoglobulin termini. In a specific embodiment, the MRDs fused to at least one of the immunoglobulins is a multimer. In one embodiment, the MRDs fused to a least one of the immunoglobulins is a homomultimer (i.e., more than one of the same MRD operably linked in tandem, optionally linked via a linker), In another embodiment, the MRDs fused to at least one of the immunoglobulins is a heteromultimer (i.e., two or more different MRDs operably linked in tandem, optionally linked via a linker). In an additional embodiment, the MRDs fused to at least one of the immunoglobulins is a dimer. In another embodiment, the MRDs fused to a least one of the immunoglobulins is a homodimer. In another embodiment, the MRDs fused to at least one of the immunoglobulins is a heterodimer.

The multiple MRDs can target the same target binding site, or two or more different target binding sites.

Similarly, the antibody and the MRD in a MRD-containing antibody may bind to the same target molecule or to different target molecules.

In some embodiments, at least one MRD and the antibody in the MRD-containing antibody can bind to their targets simultaneously. In one embodiment, each MRD in the MRD-containing antibody and the antibody can bind to its target simultaneously. Therefore, in some embodiments, the MRD-containing antibody binds two, three, four, five, six, seven, eight, nine, ten or more target molecules simultaneously.

The ability of a MRD-containing antibody to bind to multiple targets simultaneously can be assayed using methods known in the art, including, for example, those methods described in the examples below.

In some embodiments, the MRD(s) and the antibody in the MRD-containing antibody are antagonists of their respective target molecules. In other embodiments, the MRD(s) and the antibody in the MRD-containing antibody are agonists of their respective target molecules. In yet other embodiments, at least one of the MRDs in the MRD-containing antibody is an antagonist of its target molecule and the antibody is an agonist of its target molecule. In yet another embodiment, at least one of the MRDs in the MRD-containing antibody is an agonist of its target molecule, and the antibody is an antagonist of its target molecule.

In some embodiments, both the MRD(s) and the antibody in the MRD-containing antibody bind to soluble factors. In some embodiments, both the MRD(s) and the antibody in the MRD-containing antibody bind to cell surface molecules. In some embodiments, at least one MRD in the MRD-containing antibody binds to a cell surface molecule and the antibody in the MRD-containing antibody binds to a soluble factor. In some embodiments, at least one MRD in the MRD-containing antibody binds to a soluble factor and the antibody in the MRD-containing antibody binds to a cell surface molecule.

Additional peptide sequences may be added, for example, to enhance the in vivo stability of the MRD or affinity of the MRD for its target.

In preferred embodiments, the MRD-containing antibody retains particular activities of the parent antibody. In certain embodiments, the MRD-containing antibody is capable of inducing antibody dependent cell mediated cytotoxicity (ADCC). In additional embodiments, the MRD-containing antibody is capable of reducing tumor volume. In additional embodiments, the MRD-containing antibodies are capable of inhibiting tumor growth.

In certain embodiments, the MRD-containing antibody is at least as stable as the corresponding antibody without the attached MRD. In additional, embodiments, the MRD-containing antibody has at least the same affinity for Fc receptors as the corresponding parent antibody. In other nonexclusive embodiments, the MRD-containing antibody has at least the same affinity for complement receptors as the corresponding parent antibody. In other nonexclusive embodiments, the MRD-containing antibody has at least the same half-life as the corresponding parent antibody. In other embodiments, the MRD-containing antibody can be expressed at levels commensurate with the corresponding parent antibody.

In specific embodiments, the MRD-containing antibody targets ErbB2 and an angiogenic factor. In specific embodiments, the MRD-containing antibody targets ErbB2 and IGF1R. In another embodiment, the antibody targets ErbB2, and at least one MRD targets an angiogenic factor and/or IGF1R. In one embodiment, an antibody that binds to the same ErbB2 epitope as trastuzumab is operably linked to at least one MRD that targets an angiogenic factor and/or IGF1R. In an additional embodiment, an antibody that competitively inhibits trastuzumab binding is operably linked to at least one MRD that targets an angiogenic factor and/or IGF1R. In additional embodiments, the trastuzumab antibody is operably linked to at least one MRD that targets an angiogenic factor and/or IGF1R.

In some embodiments, an antibody that binds to ErbB2 is operably linked to an MRD that targets Ang2. In some embodiments, the antibody that binds to ErbB2 is linked to an Ang2 binding MRD that binds to the same Ang2 epitope as an MRD comprising the sequence of SEQ ID NO:8. In some embodiments, the antibody that binds to ErbB2 is linked to an Ang2 binding MRD that competitively inhibits an MRD comprising the sequence of SEQ ID NO:8. In some embodiments, the antibody that binds to ErbB2 is linked to an MRD comprising the sequence of SEQ ID NO:8.

In some embodiments, at least one Ang2 binding MRD is operably linked to the C-terminus of the heavy chain of an antibody that binds to ErbB2. In some embodiments, at least one Ang2 binding MRD is operably linked to the N-terminus of the heavy chain of an antibody that binds to ErbB2. In some embodiments, at least one Ang2 binding MRD is operably linked to the C-terminus of the light chain of an antibody that binds to ErbB2. In some embodiments, at least one Ang2 binding MRD is operably linked to the N-terminus of the light chain of an antibody that binds to ErbB2.

In some embodiments, at least one Ang2 binding MRD is operably linked directly to an antibody that binds to ErbB2. In additional embodiments, at least one Ang2 binding MRD is operably linked to an antibody that binds to ErbB2 via a linker.

In some embodiments, an antibody that binds to ErbB2 is operably linked to an MRD that targets IGF1R. In some embodiments, the antibody that binds to ErbB2 is linked to an IGF1R binding MRD that binds to the same IGF1R epitope as an MRD comprising the sequence of SEQ ID NO:14. In some embodiments, the antibody that binds to ErbB2 is linked to an IGF1R binding MRD that competitively inhibits an MRD comprising the sequence of SEQ ID NO:14. In some embodiments, the antibody that binds to ErbB2 is linked to an MRD comprising the sequence of SEQ ID NO:14.

In some embodiments, at least one IGF1R binding MRD is operably linked to the C-terminus of the heavy chain of an antibody that binds to ErbB2. In some embodiments, at least one IGF1R binding MRD is operably linked to the N-terminus of the heavy chain of an antibody that binds to ErbB2. In some embodiments, at least one IGF1R binding MRD is operably linked to the C-terminus of the light chain of an antibody that binds to ErbB2. In some embodiments, at least one IGF1R binding MRD is operably linked to the N-terminus of the light chain of an antibody that binds to ErbB2.

In some embodiments, at least one IGF1R binding MRD is operably linked directly to an antibody that binds to ErbB2. In additional embodiments, at least one IGF1R binding MRD is operably linked to an antibody that binds to ErbB2 via a linker.

In some embodiments, the MRD-containing antibody targets ErbB2, Ang2, and IGF1R. In some embodiments, the MRD-containing antibody comprises an antibody that targets ErbB2, an MRD that targets Ang2, and an MRD that targets IGF1R. In some embodiments, the Ang2 and IGF1R MRDs are attached to the same location on the anti-ErbB2 antibody. In some embodiments, the Ang2 and IGF1R MRDs are attached to different locations on the anti-ErbB2 antibody. In some embodiments, the Ang2 and IGF1R MRDs are on the light chain of the anti-ErbB2 antibody. In some embodiments, the Ang2 and IGF1R MRDs are on the heavy chain of the anti-ErbB2 antibody. In some embodiments, the Ang2 MRD is on the light chain of the ErbB2 antibody, and the IGF1R MRD is on the heavy chain of the anti-ErbB2 antibody. In some embodiments, the Ang2 MRD is on the heavy chain of the ErbB2 antibody, and the IGF1R MRD is on the light chain of the anti-ErbB2 antibody. In some embodiments, the Ang2 MRD is on the N-terminus of the heavy chain of the ErbB2 antibody, and the IGF1R MRD is on the C-terminus of the light chain of the anti-ErbB2 antibody. In some embodiments, the IGF1R MRD is on the N-terminus of the heavy chain of the ErbB2 antibody, and the Ang2 MRD is on the C-terminus of the light chain of the anti-ErbB2 antibody.

In some embodiments, the anti-ErbB2 antibody operably linked to an Ang2 binding MRD binds to both ErbB2 and Ang2 simultaneously. In some embodiments, the anti-ErbB2 antibody operably linked to an IGF1R binding MRD binds to both ErbB2 and IGF1R simultaneously. In some embodiments, the anti-ErbB2 antibody operably linked to an Ang2 MRD and an IGF MRD binds to ErbB2, Ang2, and IGF simultaneously. In some embodiments, the anti-ErbB2 antibody operably linked to an Ang2 and/or IGF1R binding MRD(s) exhibits ADCC activity. In additional embodiments, the anti-ErbB2 antibody operably linked to an Ang2 and/or IGF1R binding MRD(s) down-regulates Akt signaling. In additional embodiments, the anti-ErbB2 antibody operably linked to an Ang2 binding MRD inhibits Ang2 binding to Tie2. In additional embodiments, the anti-ErbB2 antibody operably linked to an Ang2 and/or IGF binding MRD(s) down-regulates IGF1R signaling. In additional embodiments, the anti-ErbB2 antibody operably linked to an Ang2 and/or IGF1R binding MRD(s) inhibits cell proliferation. In additional embodiments, the anti-ErbB2 antibody operably linked to an Ang2 and/or IGF1R binding MRD(s) inhibits tumor growth.

In specific embodiments, the MRD-containing antibody targets VEGF and an angiogenic factor. In specific embodiments, the MRD-containing antibody targets VEGF and IGF1R. In another embodiment, the antibody targets VEGF, and at least one MRD targets an angiogenic factor and/or IGF1R.

In some embodiments, an antibody that binds to VEGF is operably linked to an MRD that targets Ang2. In some embodiments, the antibody that binds to VEGF is linked to an Ang2 binding MRD that binds to the same Ang2 epitope as an MRD comprising the sequence of SEQ ID NO:8. In some embodiments, the antibody that binds to VEGF is linked to an Ang2 binding MRD that competitively inhibits an MRD comprising the sequence of SEQ ID NO:8. In some embodiments, the antibody that binds to VEGF is linked to an MRD comprising the sequence of SEQ ID NO:8.

In some embodiments, at least one Ang2 binding MRD is operably linked to the C-terminus of the heavy chain of an antibody that binds to VEGF. In some embodiments, at least one Ang2 binding MRD is operably linked to the N-terminus of the heavy chain of an antibody that binds to VEGF. In some embodiments, at least one Ang2 binding MRD is operably linked to the C-terminus of the light chain of an antibody that binds to VEGF. In some embodiments, at least one Ang2 binding MRD is operably linked to the N-terminus of the light chain of an antibody that binds to VEGF.

In some embodiments, at least one Ang2 binding MRD is operably linked directly to an antibody that binds to VEGF. In additional embodiments, at least one Ang2 binding MRD is operably linked to an antibody that binds to VEGF via a linker.

In some embodiments, an antibody that binds to VEGF is operably linked to an MRD that targets IGF1R. In some embodiments, the antibody that binds to VEGF is linked to an IGF binding MRD that binds to the same IGF epitope as an MRD comprising the sequence of SEQ ID NO:14. In some embodiments, the antibody that binds to VEGF is linked to an IGF1R binding MRD that competitively inhibits an MRD comprising the sequence of SEQ ID NO:14. In some embodiments, the antibody that binds to VEGF is linked to an MRD comprising the sequence of SEQ ID NO:14.

In some embodiments, at least one IGF binding MRD is operably linked to the C-terminus of the heavy chain of an antibody that binds to VEGF. In some embodiments, at least one IGF1R binding MRD is operably linked to the N-terminus of the heavy chain of an antibody that binds to VEGF. In some embodiments, at least one IGF1R binding MRD is operably linked to the C-terminus of the light chain of an antibody that binds to VEGF. In some embodiments, at least one IGF binding MRD is operably linked to the N-terminus of the light chain of an antibody that binds to VEGF.

In some embodiments, at least one IGF1R binding MRD is operably linked directly to an antibody that binds to VEGF. In additional embodiments, at least one IGF1R binding MRD is operably linked to an antibody that binds to VEGF via a linker.

In some embodiments, the MRD-containing antibody targets VEGF, Ang2, and IGF1R. In some embodiments, the MRD-containing antibody comprises an antibody that targets VEGF, an MRD that targets Ang2, and an MRD that targets IGF1R. In some embodiments, the Ang2 and IGF MRDs are attached to the same location on the anti-VEGF antibody. In some embodiments, the Ang2 and IGF1R MRDs are attached to different locations on the anti-VEGF antibody. In some embodiments, the Ang2 and IGF1R MRDs are on the light chain of the anti-VEGF antibody. In some embodiments, the Ang2 and IGF MRDs are on the heavy chain of the anti-VEGF antibody. In some embodiments, the Ang2 MRD is on the light chain of the anti-VEGF antibody, and the IGF1R MRD is on the heavy chain of the anti-VEGF antibody. In some embodiments, the Ang2 MRD is on the heavy chain of the anti-VEGF antibody, and the IGF1R MRD is on the light chain of the anti-VEGF antibody. In some embodiments, the Ang2 MRD is on the N-terminus of the heavy chain of the anti-VEGF antibody, and the IGF1R MRD is on the C-terminus of the light chain of the anti-VEGF antibody. In some embodiments, the IGF1R MRD is on the N-terminus of the heavy chain of the anti-VEGF antibody, and the Ang2 MRD is on the C-terminus of the light chain of the anti-VEGF antibody.

In some embodiments, the anti-VEGF antibody operably linked to an Ang2 binding MRD binds to both anti-VEGF and Ang2 simultaneously. In some embodiments, the anti-VEGF antibody operably linked to an IGF1R binding MRD binds to both anti-VEGF and IGFR1 simultaneously. In some embodiments, the anti-VEGF antibody operably linked to an Ang2 binding MRD and an IGF1R binding MRD binds to VEGF, Ang2, and IGF1R simultaneously. In some embodiments, the anti-VEGF antibody operably linked to an Ang2 and/or IGF1R binding MRD(s) exhibits ADCC activity. In additional embodiments, the anti-VEGF antibody operably linked to an Ang2 and/or IGF1R binding MRD(s) down-regulates VEGF signaling. In additional embodiments, the anti-VEGF antibody operably linked to an Ang2 binding MRD inhibits Ang2 binding to Tie2. In additional embodiments, the anti-VEGF antibody operably linked to an IGF1R binding MRD inhibits IGF1R signaling. In additional embodiments, the anti-VEGF antibody operably linked to an Ang2 and/or IGF1R binding MRD(s) inhibits cell proliferation. In additional embodiments, the anti-VEGF antibody operably linked to an Ang2 and/or IGF1R binding MRD(s) inhibits tumor growth.

An additional advantage of MRD-containing antibodies is that they can be produced using protocols that are known in the art for producing antibodies. The antibody-MRD fusion molecules can be encoded by a polynucleotide comprising a nucleotide sequence. Thus, the polynucleotides described herein can encode an MRD, an antibody heavy chain, an antibody light chain, a fusion protein comprising an antibody heavy chain and at least one MRD, and/or a fusion protein comprising an antibody light chain and at least one MRD.

The antibody-MRD fusion molecules can be encoded by a polynucleotice comprising a nucleotide sequence. A vector can contain the polynucleotide sequence. The polynucleotide sequence can also be linked with a regulatory sequence that controls expression of the polynucleotide in a host cell. A host cell, or its progeny, can contain the polynucleotide encoding the antibody-MRD fusion molecule.

VI. USES OF ANTIBODY-MRD FUSIONS

The MRD-containing antibodies described herein are useful in a variety of applications including, but not limited to, therapeutic treatment methods, such as the treatment of cancer. In certain embodiments, the MRD-containing antibodies are useful for inhibiting tumor growth, reducing neovascularization, reducing angiogenesis, inducing differentiation, reducing tumor volume, and/or reducing the tumorigenicity of a tumor. The methods of use may be in vitro, ex vivo, or in vivo methods.

In one embodiment, the MRD-containing antibodies are useful for detecting the presence of a factor or multiple factors (e.g., antigens or organisms) in a biological sample. The term "detecting" as used herein encompasses quantitative or qualitative detection. In certain embodiments, a biological sample comprises a cell or tissue. In certain embodiments, such tissues include normal and/or cancerous tissues.

The present invention contemplates therapeutic compositions useful for practicing the therapeutic methods described herein. In one embodiment, therapeutic compositions of the present invention contain a physiologically tolerable carrier together with at least one species of antibody comprising an MRD as described herein, dissolved or dispersed therein as an active ingredient. In another embodiment, therapeutic compositions of the present invention contain a physiologically tolerable carrier together with at least one species of an MRD as described herein, dissolved or dispersed therein as an active ingredient. In a preferred embodiment, the therapeutic composition is not immunogenic when administered to a human patient for therapeutic purposes.

The preparation of a pharmacological composition that contains active ingredients dissolved or dispersed therein is well understood in the art. Typically such compositions are prepared as sterile injectables either as liquid solutions or suspensions, aqueous or nonaqueous. However, solid forms suitable for solution, or suspensions, in liquid prior to use can also be prepared. The preparation can also be emulsified. Thus, an antibody—MRD containing composition can take the form of solutions, suspensions, tablets, capsules, sustained release formulations or powders, or other compositional forms.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to and to the exclusion of water.

Exemplary of such additional liquid phases are glycerin, vegetable oils such as cottonseed oil, organic esters such as ethyl oleate, and water-oil emulsions.

In one embodiment, a therapeutic composition contains an antibody comprising a MRD of the present invention, typically in an amount of at least 0.1 weight percent of antibody per weight of total therapeutic composition. A weight percent is a ratio by weight of antibody total composition. Thus, for example, 0.1 weight percent is 0.1 grams of antibody-MRD per 100 grams of total composition.

An antibody-containing therapeutic composition typically contains about 10 micrograms (μg) per milliliter (ml) to about 100 milligrams (mg) per ml of antibody as active ingredient per volume of composition, and more preferably contains about 1 mg/ml to about 10 mg/ml (i.e., about 0.1 to 1 weight percent).

A therapeutic composition in another embodiment contains a polypeptide of the present invention, typically in an amount of at least 0.1 weight percent of polypeptide per weight of total therapeutic composition. A weight percent is a ratio by weight of polypeptide total composition. Thus, for example, 0.1 weight percent is 0.1 grams of polypeptide per 100 grams of total composition.

Preferably, a polypeptide-containing therapeutic composition typically contains about 10 micrograms (ug) per milliliter (ml) to about 100 milligrams (mg) per ml of polypeptide as active ingredient per volume of composition, and more preferably contains about 1 mg/ml to about 10 mg/ml (i.e., about 0.1 to 1 weight percent).

In view of the benefit of using human, humanized or chimeric antibodies in vivo in human patients, the presently described antibody-MRD molecules are particularly well suited for in vivo use as a therapeutic reagent. The method comprises administering to the patient a therapeutically effective amount of a physiologically tolerable composition containing an antibody-MRD molecule of the invention.

The dosage ranges for the administration of the antibody-MRD molecule of the invention are those large enough to produce the desired effect in which the disease symptoms mediated by the target molecule are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

A therapeutically effective amount of an antibody-MRD molecule of the invention is typically an amount of antibody such that when administered in a physiologically tolerable composition is sufficient to achieve a plasma concentration of from about 0.1 microgram (μg) per milliliter (ml) to about 100 μg/ml, preferably from about 1 μg/ml to about 5 μg/ml, and usually about 5 μg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The antibody-MRD molecule of the invention can be administered parenterally by injection or by gradual infusion over time. Although the target molecule can typically be accessed in the body by systemic administration and therefore most often treated by intravenous administration of therapeutic compositions, other tissues and delivery means are contemplated where there is a likelihood that the tissue targeted contains the target molecule. Thus, antibody-MRD molecules of the invention can be administered intravenously, intraperitoneally, intramuscularly, subcutaneously, intracavity, transdermally, and can be delivered by peristaltic means. MRD-containing antibodies can also be delivered by aerosol to airways and lungs.

The therapeutic compositions containing an antibody-MRD molecule of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle. In a specific embodiment, the therapeutic compositions containing a human monoclonal antibody or a polypeptide are administered subcutaneously.

The compositions of the invention are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In other embodiments, the invention provides a method for treating or preventing a disease, disorder, or injury comprising administering a therapeutically effective amount or prophylactically effective amount of antibody-MRD molecule to a subject in need thereof. In some embodiments, the disease, disorder or injury is cancer.

MRD-containing antibodies are expected to have at least the same therapeutic efficacy as the antibody contained in the MRD antibody containing antibody when administered alone. Accordingly, it is envisioned that the MRD-containing antibodies can be administered to treat or prevent a disease, disorder, or injury for which the antibody contained in the MRD antibody, or an antibody that functions in the same way as the antibody contained in the MRD antibody, demonstrates a reasonably correlated beneficial activity in treating or preventing such disease, disorder or injury. This beneficial activity can be demonstrated in vitro, in an in vivo animal model, or in human clinical trials. In one embodiment, an MRD-containing antibody is administered to treat or prevent a disease, disorder or injury for which the antibody component of the MRD-containing antibody, or an antibody that functions in the same way as the antibody contained in the MRD antibody, demonstrates therapeutic or prophylactic efficacy in vitro or in an animal model. In another embodiment, an MRD-containing antibody is administered to treat or prevent a disease, disorder or injury for which the antibody component of the MRD-containing antibody, or an antibody that functions in the same way as the antibody contained in the MRD antibody, demonstrates therapeutic or prophylactic efficacy in humans. In another embodiment, an MRD-containing antibody is administered to treat or prevent a disease, disorder or injury for which the antibody component of the MRD-containing antibody, or an antibody that functions in the same way as the antibody contained in the MRD antibody, has been approved by a regulatory authority for use in such treatment or prevention.

In another embodiment, an MRD-containing antibody is administered in combination with another therapeutic to treat or prevent a disease, disorder or injury for which the antibody component of the MRD-containing antibody, or an antibody that functions in the same way as the antibody contained in the MRD antibody, in combination with the therapeutic, or a different therapeutic that functions in the same way as the therapeutic in the combination, demonstrates therapeutic or prophylactic efficacy in vitro or in an animal model. In another embodiment, an MRD-containing antibody is administered in combination with another therapeutic to treat or prevent a disease, disorder or injury for which the antibody component of the MRD-containing antibody, or an antibody that functions in the same way as the antibody contained in the MRD antibody, in combination with the therapeutic, or a different therapeutic that functions in the same way as the therapeutic in the combination, demonstrates therapeutic or prophylactic efficacy in humans. In another embodiment, an MRD-containing antibody, is administered in combination with another therapeutic to treat or prevent a disease, disorder or injury for which the antibody component of the MRD-containing antibody, or an antibody that functions in the same way as the antibody contained in the MRD antibody, in combination with the therapeutic, or a different therapeutic that functions in the same way as the therapeutic in the combination, has been approved by a regulatory authority for use in such treatment or prevention.

In one embodiment, the invention provides a method of treating cancer comprising administering a therapeutically effective amount of a VEGFA or VEGFR binding MRD-containing antibody to a patient in need thereof. Combination therapy and compositions including MRD-containing antibodies of the invention and another therapeutic are also encompassed by the invention, as are methods of treatment using these compositions. In other embodiments, compositions of the invention are administered alone or in combination with one or more additional therapeutic agents. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the therapeutic compounds or agents given first, followed by the second.

In one embodiment, MRD-containing antibodies are administered to a patient in combination with a chemotherapy agent. In one embodiment, MRD-containing antibodies and a platinum-based therapeutic agent are administered in combination to a patient. In additional embodiments, MRD-containing antibodies are administered to a patient in combination with irinotecan, fluoropyrimidine-, oxaliplatin-, and/or irinotecan. In further embodiments, MRD-containing antibodies are administered to a patient in combination with radiation therapy.

In another embodiment, the invention provides a method of treating macular degeneration comprising administering a therapeutically effective amount of a VEGFA or VEGFR binding MRD-containing antibody to a patient in need thereof.

In another embodiment, the invention provides a method of treating cancer comprising administering a therapeutically effective amount of a ErbB2(HER2) binding MRD-containing antibody to a patient in need thereof. In a specific embodiment, the invention provides a method of treating cancer comprising administering a therapeutically effective amount of trastuzumab comprising at least one MRD to a patient in need thereof. In one embodiment, the invention provides a method of treating breast cancer by administering a therapeutically effective amount of trastuzumab comprising at least one MRD to a patient having breast cancer. In other embodiments, therapeutic effective amounts of trastuzumab comprising at least one MRD are administered to treat a patient having metastatic breast cancer.

In another embodiment, the invention provides a method of treating cancer comprising administering a therapeutically effective amount of a CD20-binding MRD-containing antibody to a patient in need thereof.

In another embodiment, the invention provides a method of treating cancer comprising administering a therapeutically effective amount of a EGFR-binding MRD-containing antibody to a patient in need thereof. In a specific embodiment, the invention provides a method of treating cancer comprising administering a therapeutically effective amount of cetuximab comprising at least one MRD to a patient in need thereof. In one embodiment, the invention provides a method of treating cancer by administering a therapeutically effective amount of cetuximab comprising at least one MRD to a patient having colorectal cancer. In another embodiment, therapeutic effective amounts of cetuximab comprising at least one MRD are administered to treat a patient having metastatic colorectal cancer, metastatic breast cancer, metastatic pancreatic cancer, or metastatic non-small cell lung carcinoma. In one embodiment, the invention provides a method of treating cancer by administering a therapeutically effective amount of cetuximab comprising at least one MRD to a patient having squamous cell carcinoma of the head and neck.

In another embodiment, a therapeutically effective amount of an MRD-containing antibody is administered in combination with irinotecan, FOLFIRI, platinum-based chemotherapy, or radiation therapy.

In another embodiment, a therapeutically effective amount of an EGFR-binding MRD-containing antibody is administered in combination with irinotecan, FOLFIR1, platinum-based chemotherapy, or radiation therapy. In a specific embodiment, a therapeutically effective amount of cetuximab comprising at least one MRD is administered in combination with irinotecan, FOLFIRI, platinum-based chemotherapy, or radiation therapy In some embodiments, the MRD-containing antibodies described herein are useful for treating cancer. Thus, in some embodiments, the invention provides methods of treating cancer comprise administering a therapeutically effective amount of a MRD-containing antibody to a subject (e.g., a subject in need of treatment). In certain embodiments, the cancer is a cancer selected from the group consisting of colorectal cancer, lung cancer, ovarian cancer, liver cancer, breast cancer, brain cancer, kidney cancer, prostate cancer, melanoma, cervical cancer, and head and neck cancer. In certain embodiments, the cancer is breast cancer. In certain embodiments, the subject is a human.

In further embodiments, the MRD-containing antibodies described herein are useful for treating a cancer selected from the group consisting of carcinoma, lymphoma, blastoma, medulloblastoma, retinoblastoma, sarcoma, liposarcoma, synovial cell sarcoma, neuroendocrine tumor, carcinoid tumor, gastrinoma, islet cell cancer, mesothelioma, schwannoma, acoustic neuroma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, a tumor of the biliary tract, and head and neck cancer.

In some embodiments, MRD-containing antibodies are useful for inhibiting tumor growth. In certain embodiments, the method of inhibiting the tumor growth comprises contacting the cell with a MRD-containing antibody in vitro. For example, an immortalized cell line or a cancer cell line that expresses an MRD target and/or an antibody target is cultured in medium to which is added the MRD-containing antibody to inhibit tumor growth. In some embodiments, tumor cells are isolated from a patient sample such as, for example, a tissue biopsy, pleural effusion, or blood sample and cultured in medium to which is added a MRD-containing antibody to inhibit tumor growth.

In some embodiments, the method of inhibiting tumor growth comprises contacting the tumor or tumor cells with a therapeutically effective amount of the MRD-containing antibody in vivo. In certain embodiments, contacting a tumor or tumor cell is undertaken in an animal model. For example, MRD-containing antibodies can be administered to xenografts in immunocompromised mice (e.g., NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a MRD-containing antibody to inhibit tumor cell growth. In some embodiments, the MRD-containing antibody is administered at the same time or shortly after introduction of tumorigenic cells into the animal to prevent tumor growth. In some embodiments, the MRD-containing antibody is administered as a therapeutic after the tumorigenic cells have grown to a specified size.

In certain embodiments, the method of inhibiting tumor growth comprises administering to a subject a therapeutically effective amount of a MRD-containing antibody. In certain embodiments, the subject is a human. In certain embodiments, the subject has a tumor or has had a tumor removed. In certain embodiments, the tumor expresses an antibody target. In certain embodiments, the tumor overexpresses the MRD target and/or the antibody target.

In certain embodiments, the inhibited tumor growth is selected from the group consisting of brain tumor, colorectal tumor, lung tumor, ovarian tumor, liver tumor, breast tumor, kidney tumor, prostate tumor, melanoma, cervical tumor, and head and neck tumor. In certain embodiments, the tumor is a breast tumor.

In additional embodiments, MRD-containing antibodies are useful for reducing tumorigenicity. Thus, in some embodiments, the method of reducing the tumorigenicity of a tumor in a subject, comprises administering a therapeutically effective amount of a MRD-containing antibody to the subject. In certain embodiments, the tumor comprises cancer stem cells. In certain embodiments, the frequency of cancer stem cells in the tumor is reduced by administration of the agent.

The following examples are intended to illustrate but not limit the invention.

EXAMPLES

Example 1

Integrin Targeting Antibody-MRD Molecules

Novel antibody-MRD fusion molecules were prepared by fusion of an integrin αvβ3-targeting peptides to catalytic antibody 38C2. Fusions at the N-termini and C-termini of the light chain and the C-termini of the heavy chain were most effective. Using flow cytometry, the antibody conjugates were shown to bind efficiently to integrin αvβ3-expressing human breast cancer cells. The antibody conjugates also retained the retro-aldol activity of their parental catalytic antibody 38C2, as measured by methodol and doxorubicin prodrug activation. This demonstrates that cell targeting and catalytic antibody capability can be efficiently combined for selective chemotherapy.

Example 2

Angiogenic Cytokine Targeting Antibody-MRD Molecules

Angiogenic cytokine targeting antibody-MRD fusion molecules were constructed. The antibody used was 38C2, which was fused with a MRD containing the 2xCon4 peptide (AQQEECEWDPWTCEHMGSGSATGGSG-STASSGSGSATHQEECEWDP WTCEHMLE (SEQ ID NO:10)). The MRD-containing peptide was fused to either the N- or C-terminus of the light chain and the C-terminus of the heavy chain. Similar results were found with the other Ang2 MRD peptides. Additional Ang2 MRD peptides include: MGAQTNFMPMDNDELLLYEQFILQQ-GLEGGSGSTASSGSGSSLGAQTNF MPMDNDELLLY (SEQ ID NO:20) (LM-2x-32); AQQEECEWDPWTCEHMG SGSATGGSGSTASSGSGSATHQEECEWD-PWTCEHMLE (SEQ ID NO:10) (2xCon4); AQQEECE-FAPWTCEHM (SEQ ID NO:21) ConFA; core XnEFAP-WTXn where n is from about 0 to 50 amino acid residues (SEQ ID NO:22); AQQEECEFAPWTCEHMGSG-SATGGSGSTASSGSGSATHQEECE FAPWTCEHMLE (SEQ ID NO:23) (2xConFA); AQQEECELAPWTCEHM (SEQ ID NO:24) (ConLA); XnELAPWTXn where n is from about 0 to 50 amino acid residues (SEQ ID NO:25); AQQEECELAPWTCEHMGSGSATGGSGSTASS GSG-SATHQEECELAPWTCEHMLE (SEQ ID NO:26) (2xConLA); AQQEE CEFSPWTCEHM ConFS (SEQ ID NO:27); XnEFSPWTXn where n is from about 0 to 50 amino acid residues (SEQ ID NO:28); AQQEECEFSPWTCEH-MGSGS ATGGSGSTASSGSGSATHQEECEFSPWT-CEHMLE (SEQ ID NO:29) (2xConFS); AQQEECELEP-WTCEHM ConLE (SEQ ID NO:30); XnELEPWTXn where n is from about 0 to 50 amino acid residues (SEQ ID NO:31); and AQQEECELEPWTCEHMGSGSATGGSG-STASSGSGSATHQEECELEP WTCEHMLE (SEQ ID NO:32) (2xConLE).

It should be understood that such peptides can be present in dimmers, trimers or other multimers either homologous or heterologous in nature. For example, one can dimerize identical Con-based sequences such as in 2xConFA to provide a homologous dimer, or the Con peptides can be mixed such that ConFA is combined with ConLA to create ConFA-LA heterodimer with the sequence:

(SEQ ID NO: 33)
AQQEECEFAPWTCEHMGSGSATGGSGSTASSGSGSATHQEECE

LAPWTCEHMLE.

Another illustrative heterodimer is ConFA combined with ConFS to create ConFA-FS with the sequence: AQQEECE-FAPWTCEHMGSGSATGGSGST ASSGSG-SATHQEECEFSPWTCEHMLE (SEQ ID NO:34).

One of skill in the art, given the teachings herein, will appreciate that other such combinations will create functional Ang2 binding MRDs as described herein.

Example 3

Antibody-MRD Fusions with Non-Catalytic Antibodies

A humanized mouse monoclonal antibody, LM609, directed towards human integrin αvβ3 has been previously described (Rader, C. et. al., *PNAS* 95:8910-5 (1998)).

Figure 3:
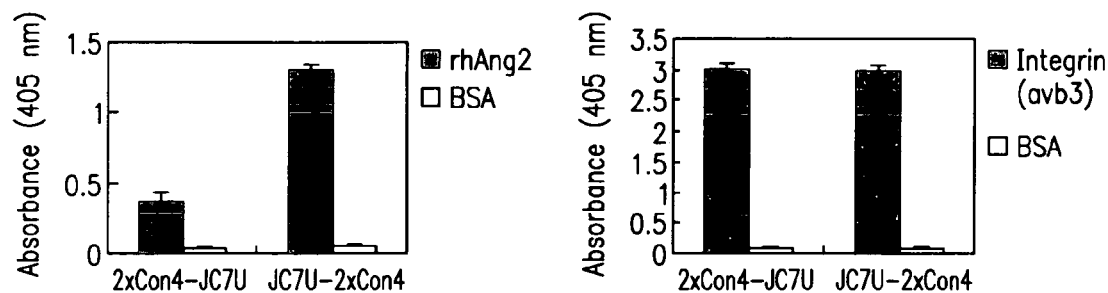
FIG. 3 depicts the results of an enzyme linked immunosorbent assay (ELISA) in which integrin and Ang2 were bound by an anti-integrin antibody (JC7U) fused to a Ang2 targeting MRD (2xCon4).
Figure 4:
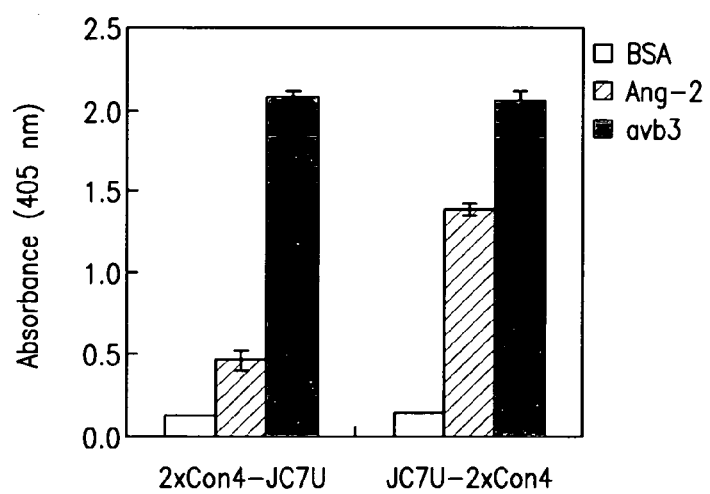
FIG. 4 depicts the results of an ELISA in which integrin and Ang2 were bound by an anti-integrin antibody (JC7U) fused to a Ang2 targeting MRD (2xCon4).

A human non-catalytic monoclonal Ab, JC7U was fused to an anti-Ang2 MRD containing 2xCon4 (AQQEECEWDP-WTCEHMGSGSATGGSGSTASSGS GSATHQEECEWD-PWTCEHMLE (SEQ ID NO:10)) at either the N- or C-terminus of the light chain. 2xCon4 (AQQEECEWDPWTCEHMGSGSAT GGSGSTASSGSG-SATHQEECEWDPWTCEHMLE (SEQ ID NO:10)) was studied as an N-terminal fusion to the Kappa chain of the antibody (2xCon4-JC7U) and as a C-terminal fusion (JC7U-2xCon4). Both fusions maintained integrin and Ang2 binding. As shown in the left panel of FIG. 3, both antibody constructs (2xCon4-JC7U and JC7U-2xCon4) specifically bound to recombinant Ang2 as demonstrated by ELISA studies. Binding to Ang2, however, is significantly higher with JC7U-2xCon4, which has the 2xCon4 (SEQ ID NO:10) fusion at the C-terminus of the light chain of the antibody. The right panel of FIG. 3 depicts the binding of Ang2-JC7U and JC7U-Ang2 to integrin αvβ3. The results show that fusion of 2xCon4 (SEQ ID NO:10) to either the N- or the C-light chain terminus does not affect mAb JC7U binding to integrin αvβ3. FIG. 4 depicts another ELISA study using the same antibody-MRD fusion constructs.

Example 4

HERCEPTIN®-MRD Fusion Molecules

Another example of MRD fusions to a non-catalytic antibody are HERCEPTIN®-MRD fusion constructs. The HERCEPTIN®-MRD fusions are multifunctional, both small-molecule αv integrin antagonists and the chemically programmed integrin-targeting antibody show remarkable efficacy in preventing the breast cancer metastasis by interfering with αv-mediated cell adhesion and proliferation. MRD fusions containing HERCEPTIN®-2xCon4 (which targets ErbB2 and Ang2) and HERCEPTIN®-V114 (which targets ErbB2 and VEGF targeting) and HERCEPTIN®-RGD-4C-2xCon4 (which targets ErbB2, ang2, and integrin targeting) are effective.

Example 5

VEGF Targeting Antibody-MRD Molecules

An antibody containing an MRD that targets VEGF was constructed. A MRD which targets vl 14 (SEQ ID NO:13) was fused at the N-terminus of the kappa chain of 38C2 and HERCEPTIN® using a linker. Expression and testing of the resulting antibody-MRD fusion constructs demonstrated strong VEGF binding.

Example 6

IGF1R Targeting Antibody-MRD Molecules

Fusion of an MRD which targets IGF1R(SFYSCLE-SLVNGPAEKSRG QWDGCRKK (SEQ ID NO:14)) to the N-terminus of the kappa chain of 38C2 and HERCEPTIN® using the long linker sequence as a connector was studied. Expression and testing of the resulting antibody-MRD fusion constructs demonstrated strong IGF1R binding. Additional clones showing high binding to IGR1R were identified after several rounds of mutagenesis and screening of the regions described in Table 4. The preferred sequences listed in Table 5 bind IGF1R and show no significant or no binding affinity to the insulin receptor, thereby suggesting specificity for IGF1R.

TABLE 4

Template for further mutagenesis.

| Name | DNA | AA |
|---|---|---|
| Rm2-2-218 | GTGGAGTGCAGGGCGCCG (SEQ ID NO: 50) | VECRAP (SEQ ID NO: 51) |
| Rm2-2-316 | GCTGAGTGCAGGGCTGGG (SEQ ID NO: 52) | AECRAG (SEQ ID NO: 53) |
| Rm2-2-319 | CAGGAGTGCAGGACGGGG (SEQ ID NO: 54) | QECRTG (SEQ ID NO: 55) |

TABLE 5

| Mutant | Amino acid sequence | Template | SEQ ID NO |
|---|---|---|---|
| Rm4-31 | NFYQCIEMLASHPAEKSRGQWQECRTGG | Rm2-2-319 | 35 |
| Rm4-33 | NFYQCIEQLALRPAEKSRGQWQECRTGG | Rm2-2-319 | 36 |
| Rm4-39 | NFYQCIDLLMAYPAEKSRGQWQECRTGG | Rm2-2-319 | 37 |
| Rm4-310 | NFYQCIERLVTGPAEKSRGQWQECRTGG | Rm2-2-319 | 38 |
| Rm4-314 | NFYQCIEYLAMKPAEKSRGQWQECRTGG | Rm2-2-319 | 39 |
| Rm4-316 | NFYQCIEALQSRPAEKSRGQWQECRTGG | Rm2-2-319 | 40 |
| Rm4-319 | NFYQCIEALSRSPAEKSRGQWQECRTGG | Rm2-2-319 | 41 |
| Rm4-44 | NFYQCIEHLSGSPAEKSRGQWQECRTG | Rm2-2-319 | 42 |
| Rm4-45 | NFYQCIESLAGGPAEKSRGQWQECRTG | Rm2-2-319 | 43 |
| Rm4-46 | NFYQCIEALVGVPAEKSRGQWQECRTG | Rm2-2-319 | 44 |
| Rm4-49 | NFYQCIEMLSLPPAEKSRGQWQECRTG | Rm2-2-319 | 45 |
| Rm4-410 | NFYQCIEVFWGRPAEKSRGQWQECRTG | Rm2-2-319 | 46 |
| Rm4-411 | NFYQCIEQLSSGPAEKSRGQWQECRTG | Rm2-2-319 | 47 |
| Rm4-415 | NFYQCIELLSARPAEKSRGQWAECRAG | Rm2-2-316 | 48 |
| Rm4-417 | NFYQCIEALARTPAEKSRGQWVECRAP | Rm2-2-218 | 49 |

Example 7

ErbB2 Binding, Ang2-Targeting Antibody-MRD Molecules

Figure 5:
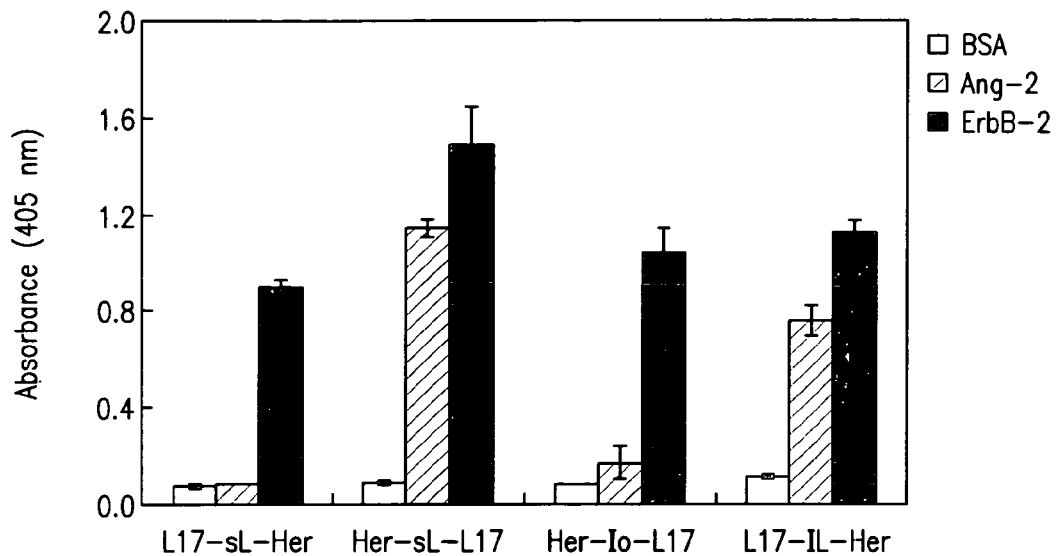
FIG. 5 depicts the results of an ELISA in which an anti-ErbB2 antibody was fused to an MRD which targets Ang2.

An antibody was constructed which contains an MRD that targets Ang2 (L17) (SEQ ID NO:7) fused to the light chain of an antibody which binds to ErbB2. Either the short linker sequence, the long linker sequence, or the 4th loop in the light chain constant region was used as a linker. FIG. 5 depicts the results of an ELISA using constructs containing an N-terminal fusion of an Ang2 targeting MRD with the ErbB2 antibody with the short linker peptide (GGGS (SEQ ID NO:1)) (L17-sL-Her), a C-terminal fusion of Ang2 targeting MRD with the ErbB2 antibody with the short linker peptide (Her-sL-L17), a C-terminal fusion of Ang2 targeting MRD with the ErbB2 antibody with the 4th loop in the light chain constant region (Her-lo-L17), or an N-terminal fusion of Ang2 targeting MRD with the ErbB2 antibody with the long linker peptide (SSGGGGSGGGGGGSSRSS (SEQ ID NO:19)) (L17-1L-Her). ErbB2 was bound with varying degrees by all of the constructs. However, Ang2 was bound only by Her-sL-L17 and L17-1L-Her.

Example 8

Figure 6:
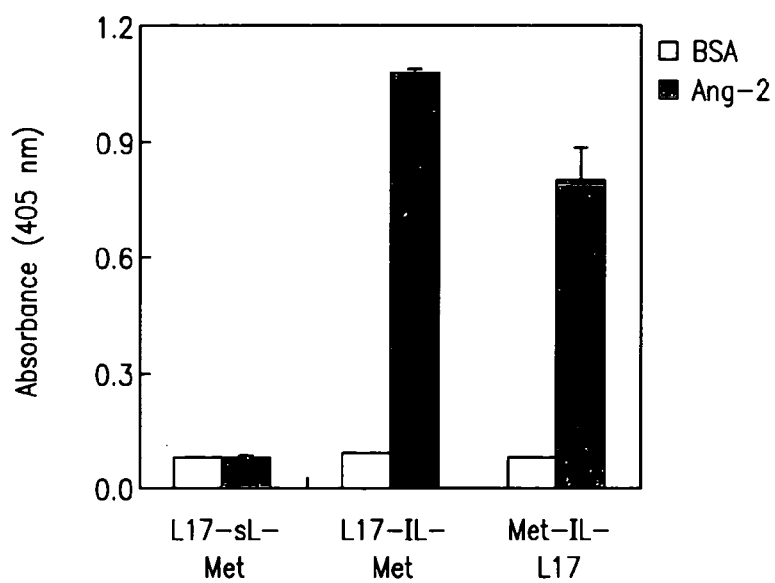
FIG. 6 depicts the results of an ELISA in which an Ang2 targeting MRD was fused to a hepatocyte growth factor receptor (cMET) binding antibody.

Hepatocyte Growth Factor Receptor Binding, Ang2-Targeting Antibody-MRD Molecules Fusion of an MRD which targets Ang2 (L17) (SEQ ID NO:7) was made to either the N-terminus or C-terminus of the light chain of the Met antibody, which binds to hepatocyte growth factor receptor. Either the short linker sequence or the long linker sequence were used as a connector. FIG. 6 depicts the results of an ELISA using constructs containing N-terminal fusion of Ang2 targeting MRD with the Met antibody with the short linker peptide (GGGS (SEQ ID NO:1)) (L17-sL-Met), N-terminal fusion of Ang2 targeting MRD with the Met antibody with the long linker peptide (SSGGGGSGGGGGGSSRSS (SEQ ID NO:19)) (L17-1L-Met), and C-terminal fusion of Ang2 targeting MRD with the Met antibody with the long linker peptide (Met-iL-L17). Expression and testing of the resulting antibody-MRD fusion constructs demonstrated strong Ang2 binding when the long linker peptide was used. Fusion of the Ang2 targeting MRD to the C-light chain terminus of the antibody resulted in slightly higher binding to Ang2 then fusion of the Ang2 targeting to the N-light chain terminus of the antibody.

Example 9

ErbB2 Binding, Integrin-Targeting Antibody-MRD Molecules

Figure 7:
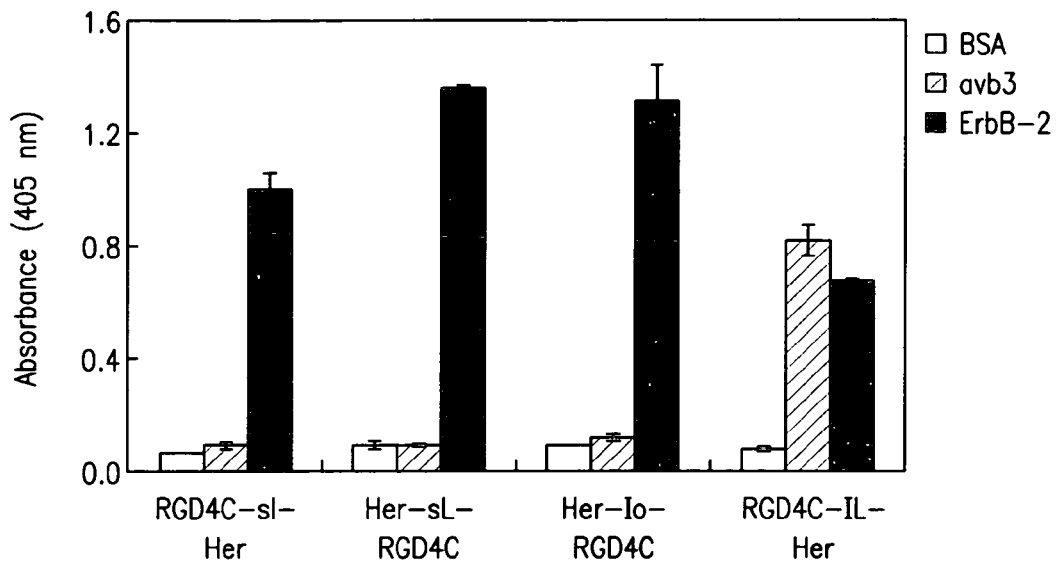
FIG. 7 depicts the results of an ELISA in which an integrin targeting MRD was fused to an ErbB2 binding antibody.

An antibody was constructed which contains an MRD that targets integrin αvβ3 (RGD4C fused to the light chain of an antibody HERCEPTIN® which binds to ErbB2 (Her). Either the short linker sequence, the long linker sequence, or the 4th loop in the light chain constant region was used as a linker. FIG. 7 depicts the results of an ELISA using constructs containing an N-terminal fusion of integrin αvβ3 targeting MRD with the ErbB2 antibody with the short linker peptide (GGGS (SEQ ID NO:1)) (RGD4C-sL-Her), a C-terminal fusion of integrin αvβ3 targeting MRD with the ErbB2 antibody with the short linker peptide (Her-sL-RGD4C), a C-terminal fusion of integrin αvβ3 targeting MRD with the ErbB2 antibody with the 4th loop in the light chain constant region (Her-lo-RGD4C), or an N-terminal fusion of integrin αvβ3 targeting MRD with the ErbB2 antibody with the long linker peptide (SSGGGGSGGGGGGSSRSS (SEQ ID NO:19)) (RGD4C-1L-Her). ErbB2 was bound with varying degrees by all of the constructs. However, integrin αvβ3 was bound only by RGD4C-1L-Her.

Example 10

Figure 8:
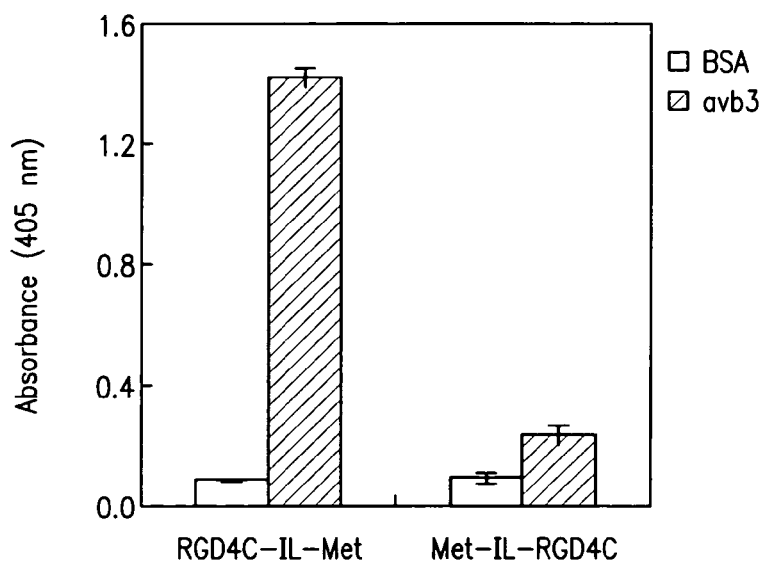
FIG. 8 depicts the results of an ELISA in which an integrin targeting MRD was fused to an hepatocyte growth factor receptor binding antibody.

Hepatocyte Growth Factor Receptor Binding, Integrin-Targeting Antibody MRD Molecules An antibody was constructed which contains an MRD that targets integrin αvβ3 (RGD4C) fused to the light chain of an antibody which binds to the hepatocyte growth factor receptor (Met). Antibody-MRD constructs containing the long linker sequence were used. FIG. 8 depicts the results of an ELISA using constructs containing an N-terminal fusion of integrin αvβ3 targeting MRD with the hepatocyte growth factor receptor antibody (RGD4C-1 L-Met), or a C-terminal fusion of integrin αvβ3 targeting MRD with the hepatocyte growth factor receptor antibody (Met-1L-RGD4C). The RGD4C-1L-Met demonstrated strong integrin αvβ3 binding.

Example 11

Figure 9:
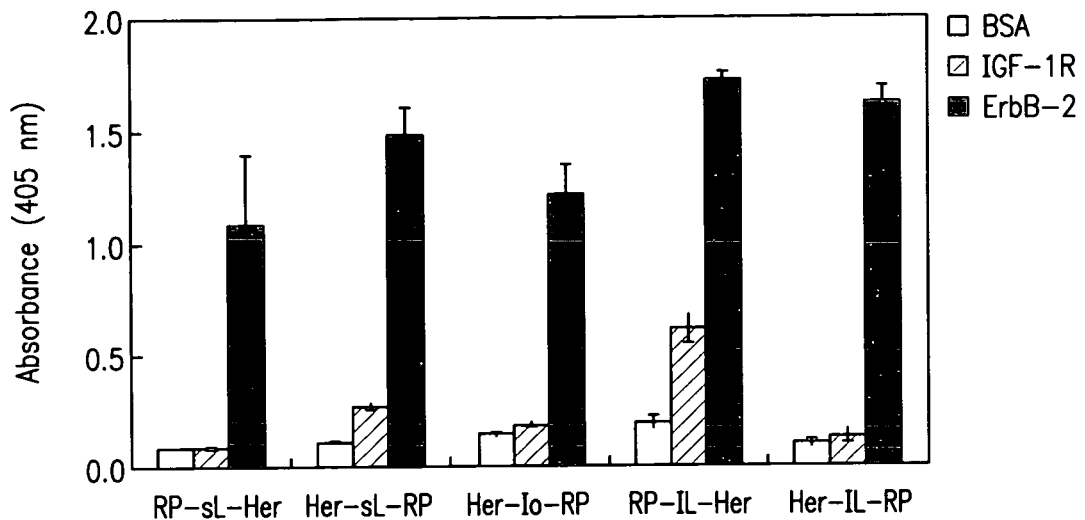
FIG. 9 depicts the results of an ELISA in which an insulin-like growth factor-I receptor targeting MRD was fused to an ErbB2 binding antibody.

ErbB2 Binding, Insulin-like Growth Factor-I Receptor-Targeting Antibody-MRD Molecules Antibodies were constructed which contains an MRD that targets insulin-like growth factor-I receptor (RP) (SEQ ID NO:14) fused to the light chain of an antibody which binds to ErbB2 (Her). Either the short linker peptide, the long linker peptide, or the 4th loop in the light chain constant region was used as a linker (Carter et al., Proc Natl Acad Sci 89:4285-9 (1992); U.S. Pat. No. 5,677,171; and ATCC Deposit 10463, each of which is herein incorporated by reference). FIG. 9 depicts the results of an ELISA using constructs containing an N-terminal fusion of insulin-like growth factor-I receptor targeting MRD with the ErbB2 antibody with the short linker peptide (RP-sL-Her), a C-terminal fusion of insulin-like growth factor-I receptor targeting MRD with the ErbB2 antibody and the short linker peptide (Her-sL-RP), a C-terminal fusion of insulin-like growth factor-I receptor targeting MRD with the ErbB2 antibody with the 4th loop in the light chain constant region (Her-lo-RP), an N-terminal fusion of insulin-like growth factor-I receptor targeting MRD with the ErbB2 antibody with the long linker peptide (RP-1L-Her), or a C-terminal fusion of insulin-like growth factor-I receptor targeting MRD with the ErbB2 antibody with the long linker peptide (Her-1L-RP). ErbB2 was bound with varying degrees by all of the constructs. Insulin-like growth factor-I receptor was bound by RP-1L-Her.

Example 12

ErbB2 Binding. VEGF-Targeting Antibody-MRD Molecules

Figure 10:
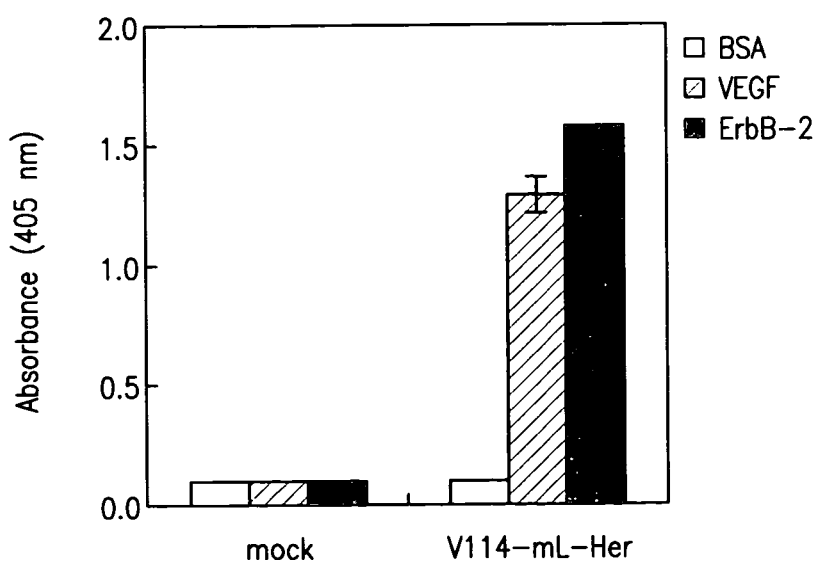
FIG. 10 depicts the results of an ELISA in which a VEGF-targeting MRD was fused to an ErbB2 binding antibody.

Fusion of an MRD which targets VEGF (V1 14) (SEQ ID NO:13) (Fairbrother W. J., et al, Biochemistry. 37:177754-64 (1998)) was made to the N-terminus of the light chain of a ErbB2-binding antibody (Her). A medium linker peptide (SSGGGGSGGGGGSS (SEQ ID NO:2)) was used as a connector. FIG. 10 depicts the results of an ELISA using a construct containing an N-terminal fusion of VEGF targeting MRD with the ErbB2-binding antibody with the medium linker peptide (V1 14-mL-Her). Expression and testing of the resulting antibody-MRD fusion construct demonstrated strong VEGF and ErbB2 binding.

Example 13

Integrin Targeting Antibody-MRD Molecules

Figure 11:
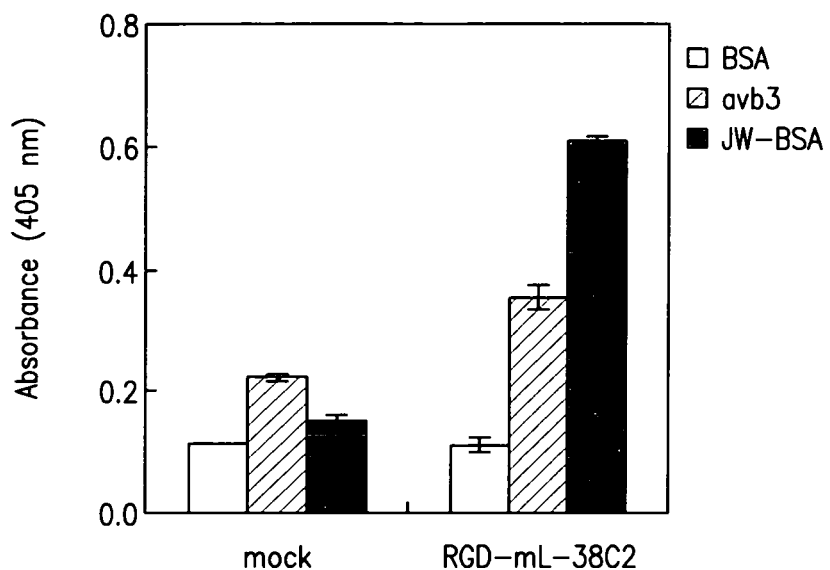
FIG. 11 depicts the results of an ELISA in which an integrin targeting MRD was fused to a catalytic antibody.

Fusion of an MRD which targets integrin αvβ3 (RGD) to the N-terminus of the light chain of 38C2 using the medium linker peptide as a connector was studied. FIG. 11 demonstrates that expression and testing of the resulting antibody-MRD fusion construct had strong integrin αvβ3 binding.

Example 14

Ang2 Targeting Antibody-MRD Molecules

Figure 12:
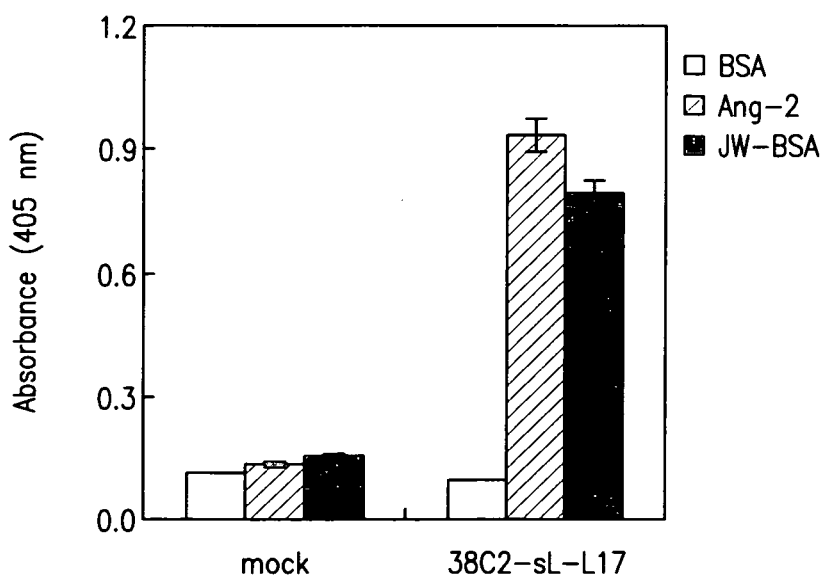
FIG. 12 depicts the results of an ELISA in which an Ang2-targeting MRD was fused to a catalytic antibody.

Fusion of an MRD which targets Ang2 (L 17) (SEQ ID NO:7) to the C-terminus of the light chain of 38C2 using the short linker sequence as a connector was studied. FIG. 12 demonstrates that expression and testing of the resulting antibody-MRD fusion construct had strong Ang2 binding.

Example 15

ErbB2 Binding, Integrin and Ang2 Targeting Antibody-MRD Molecules

Figure 13:
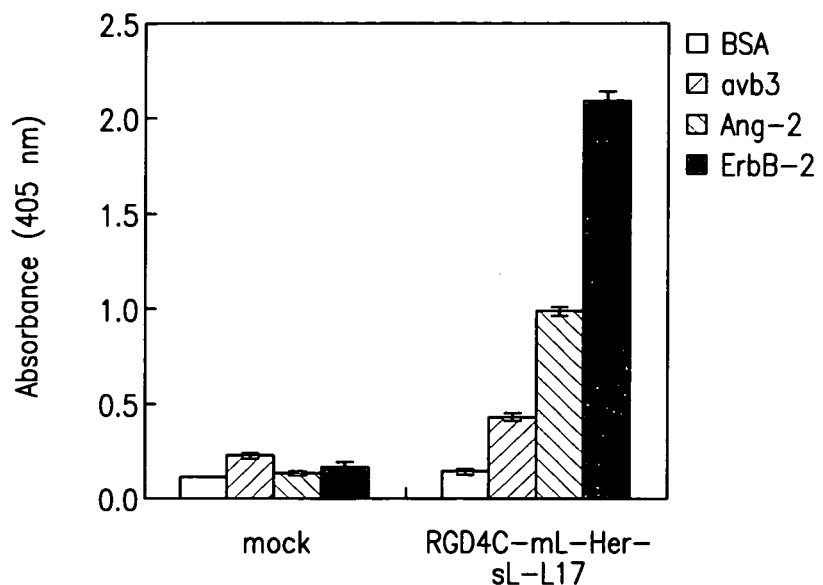
FIG. 13 depicts the results of an ELISA in which an integrin targeting MRD and an Ang2 targeting MRD were fused to an ErbB2 binding antibody.

An MRD which targets integrin αvβ3 (RGD4C) was connected to the N-terminus of the light chain of an ErbB2 targeting antibody (Her) with a medium linker, and an Ang2 (L17) targeting MRD was connected by a short linker to the C-terminus of the same ErbB2 targeting antibody (RGD4C-mL-Her-sL-L17). FIG. 13 demonstrates that the resulting antibody-MRD fusion construct bound to integrin, Ang2, and ErbB2.

Example 16

ErbB2 Binding, Integrin-Targeting Antibody-MRD Molecules

Figure 14:
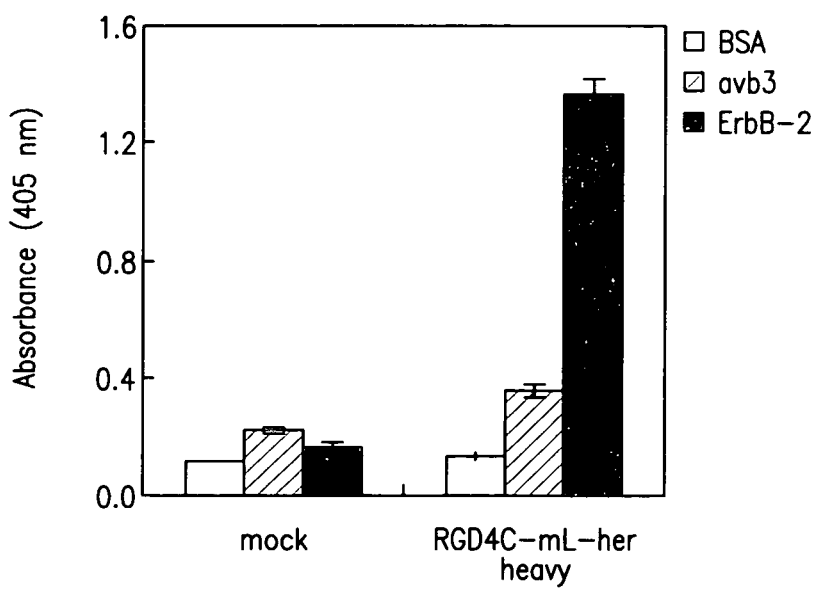
FIG. 14 depicts the results of an ELISA in which an integrin targeting MRD was fused to an ErbB2 binding antibody.

An antibody was constructed which contains an MRD that targets integrin αvβ3 (RGD4C) fused to the N-terminus of the heavy chain of an antibody which binds to ErbB2 (Her) using the medium linker as a connector (RGD4C-mL-her-heavy). FIG. 14 depicts the results of an ELISA using the construct. Both integrin and ErbB2 were bound by the construct.

Example 17

Figure 15:
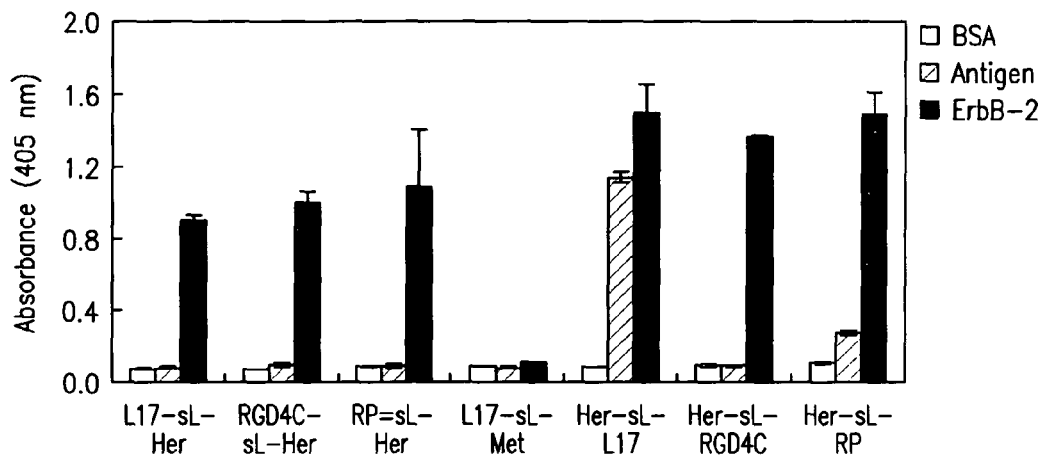
FIG. 15 depicts the results of an ELISA in which an integrin, Ang2, or insulin-like growth factor-I receptor-targeting MRD was fused to an ErbB2 or hepatocyte growth factor receptor-binding antibody with a short linker peptide.

ErbB2 or Hepatocyte Growth Factor Receptor Binding, and Integrin, Ang2 or Insulin-Like Growth Factor-I Receptor-Targeting Antibody-MRD Molecules with the Short Linker Peptide Antibody-MRD molecules were constructed which contain ErbB2 or hepatocyte growth factor receptor binding antibodies, and integrin αvβ3, Ang2 or insulin-like growth factor-I receptor-targeting MRD regions were linked with the short linker peptide to the light chain of the antibody. FIG. 15 depicts the results of an ELISA using constructs containing an N-terminal fusion of Ang2 targeting MRD fused to the ErbB2 antibody (L17-sL-Her), an N-terminal fusion of integrin-targeting MRD with the ErbB2 antibody (RGD4C-sL-Her), an N-terminal fusion of insulin-like growth factor-I receptor targeting MRD with the ErbB2 binding antibody (RP-sL-Her), a C-terminal fusion of Ang2 targeting MRD with the hepatocyte growth factor receptor binding antibody (L17-sL-Met), a C-terminal fusion of Ang2 targeting MRD with the ErbB2 binding antibody (Her-sL-L17), a C-terminal fusion of integrin targeting MRD with the ErbB2 binding antibody (Her-sL-RGD4C), or a C-terminal fusion of insulin-like growth factor-I receptor targeting MRD with the ErbB2 binding antibody (Her-sL-RP). ErbB2 was bound with varying degrees by the antibody-MRD constructs, with the exception of the construct containing the hepatocyte growth factor receptor-binding antibody. Antigen was bound only by the Her-sL-L17 construct.

Example 18

Figure 16:
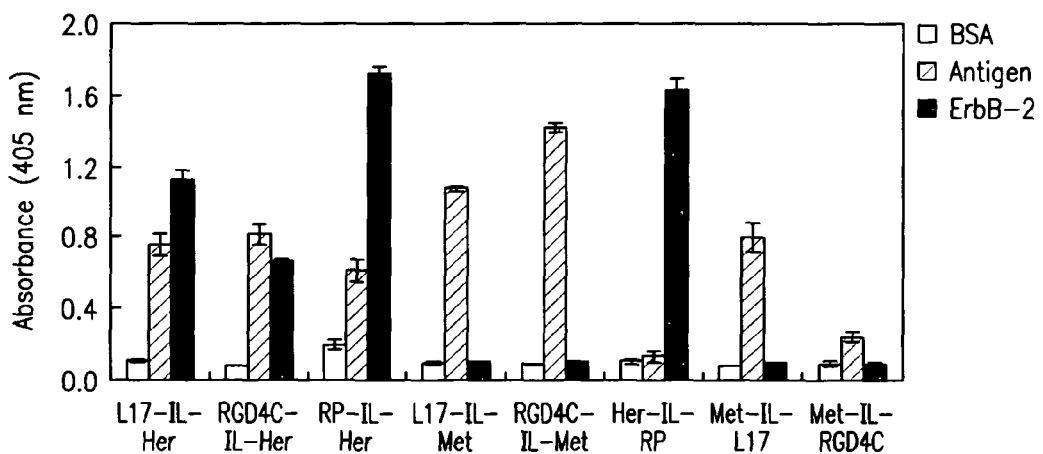
FIG. 16 depicts the results of an ELISA in which an integrin, Ang2, or insulin-like growth factor-I receptor-targeting MRD was fused to an ErbB2 or hepatocyte growth factor receptor-binding antibody with a long linker peptide.
Figure 17A:
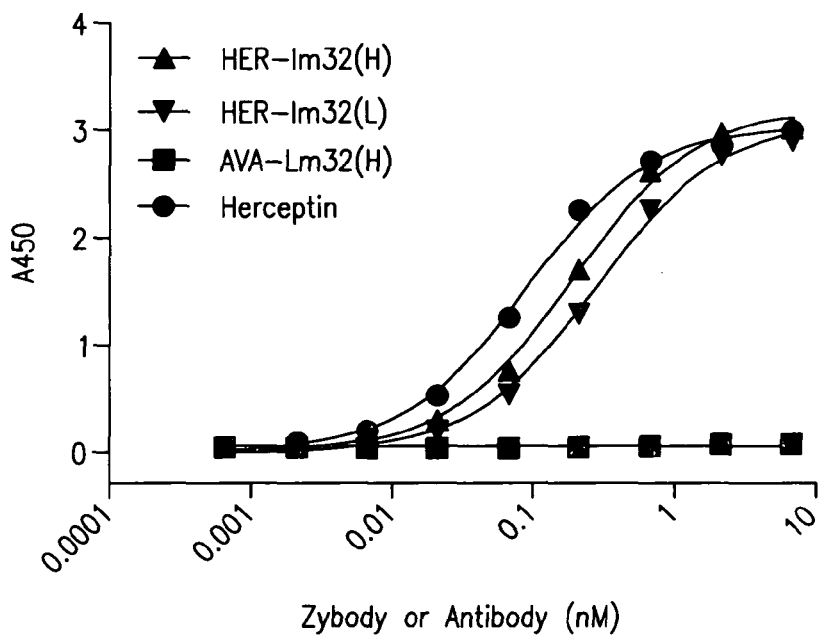
FIG. 17A depicts the results of an assay for direct binding of a HERCEPTIN® based zybody (i.e. an MRD containing HERCEPTIN® antibody sequences) antibody-MRDs and a HERCEPTIN® antibody to Her2 (ErbB2) Fc in the presence of biotinylated Ang2. Binding was detected with HRP-conjugated anti-human kappa chain mAb.
Figure 17B:
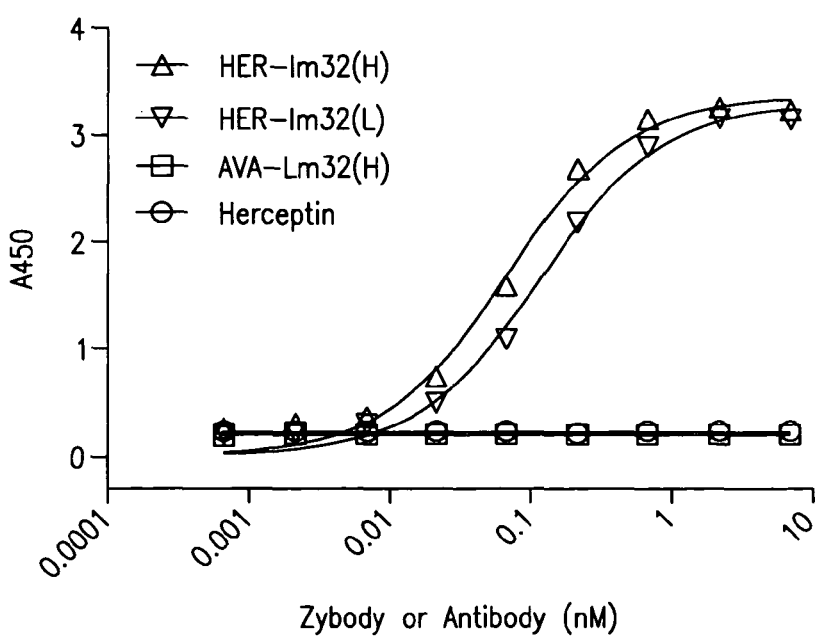
FIG. 17B depicts the results of an assay for direct binding of a HERCEPTIN® based zybody (i.e., an MRD containing HERCEPTIN® antibody sequences) and a HERCEPTIN® antibody to Her2 Fc in the presence of biotinylated Ang2. Binding was detected with horseradish peroxidase (HRP)-conjugated streptavidin.

ErbB2 or Hepatocyte Growth Factor Receptor Binding, and Integrin, Ang2 or Insulin-Like Growth Factor-I Receptor-Targeting Antibody-MRD Molecules with the Long Linker Peptide Antibody-MRD molecules were constructed which contain ErbB2 or hepatocyte growth factor receptor binding antibodies, and integrin αvβ3, Ang2 or insulin-like growth factor-I receptor-targeting MRD regions linked with the long linker peptide to the light chain of the antibody. FIG. 16 depicts the results of an ELISA using constructs containing an N-terminal fusion of Ang2 targeting MRD fused to the ErbB2 antibody (L17-1L-Her), an N-terminal fusion of integrin-targeting MRD with the ErbB2 antibody (RGD4C-1L-Her), an N-terminal fusion of insulin-like growth factor-I receptor-targeting MRD with the ErbB2 binding antibody (RP-1L-Her), a C-terminal fusion of Ang2 targeting MRD with the hepatocyte growth factor receptor binding antibody (L17-1L-Met), a C-terminal fusion of integrin targeting MRD with the hepatocyte growth factor receptor binding antibody (RGD4C-1L-Met), a C-terminal fusion of Ang2 targeting MRD with the insulin-like growth factor-I receptor binding antibody (Her-1L-RP), a C-terminal fusion of Ang2 targeting MRD with the hepatocyte growth factor receptor binding antibody (Met-1L-L17), or a C-terminal fusion of integrin targeting MRD with the hepatocyte growth factor receptor binding antibody (Met-1L-RGD4C). As shown in FIG. 16, antibody-MRD fusions are effective to bind antigen and ErbB2. Lu et al. *J Biol. Chem.* 2005 May 20; 280(20): 19665-72. Epub 2005 Mar. 9; Lu et al. *J Biol. Chem.* 2004 Jan. 23; 279(4):2856-65. Epub 2003 Oct. 23.

Example 19

Expression and Purification of Antibodies Containing MRDs

Molecular recognition domains were constructed and expressed in a pcDNA 3.3 vector as fusion proteins with either the heavy or light chains of antibodies. For protein production, plasmid DNAs encoding the heavy and light chains of the antibodies containing MRDs were first transformed into chemically competent bacteria in order to produce large amounts of DNA for transient transfection. Single transformants were propagated in LB media and purified using Qiagen's Endotoxin Free Plasmid Kits. Briefly, cells from an overnight culture were lysed; lysates were clarified and applied to an anion-exchange column, and then subjected to a wash step and eluted with high salt. Plasmids were precipitated, washed, and resuspended in sterile water.

HEK293T cells were expanded to the desired final batch size (about 5 L) prior to transfection. The purified plasmid (1 mg per liter of production) was complexed with the polyethylenimine (PEI) transfection reagent, added to the shake flask culture, and incubated at 37° C. The culture was monitored daily for cell count, cell diameter, and viability. The conditioned medium was harvested and stored at −80° C. until purification.

Antibodies containing MRDs were purified from the conditioned medium using affinity chromatography. Culture supernatant was filter clarified and applied directly to a chromatography column containing recombinant Protein A Sepharose (GE Healthcare). The column was washed, and bound antibodies containing MRDs were eluted by lowering buffer pH. Following elution, eluate fractions were immediately adjusted to physiologic pH. Following Protein A affinity purification, an additional optional polishing chromatographic step can be performed as needed.

Purified proteins were dialyzed into PBS, concentrated to ~1-4 mg/ml, sterile filtered, aliquoted aseptically, and stored frozen at −80° C. All steps of the purification were monitored by SDS-PAGE-Coomassie, and precautions were taken during the purification to keep endotoxin levels as minimal as possible.

The final product was analyzed for endotoxin levels (EndoSafe), purity (SDS-PAGE-coomassie, analytical SEC-HPLC), protein identity (Western blot), and yield (Bradford assay). An additional size exclusion HPLC analysis was performed to assess the level of aggregates.

The data presented in Table 6 indicate that the antibodies containing MRDs can be expressed and purified using conventional techniques.

TABLE 6

| Zybody | Yield (mg) | Purity | Aggregates (%) | Endotoxin (EU/ml) |
|---|---|---|---|---|
| HER2xCon4(H) | 36 | >90% | 4.6 | <1 |
| HER-lm32(H) | 57 | >90% | 1 | 2.02 |
| HER-lm32(L) | 98 | >90% | 2 | 3.26 |
| AVA-lm32(H) | 12 | >90% | 0 | <1 |

Example 20

Simultaneous binding of HER Lm32(H) and HER Lm32 (L) to Her2 and Ang2

A. Methods

Ninety-six-well plates were coated overnight with rHER2-Fc (R&D cat#1129-ER-050) at 20 ng/ml (100 µl/well). Wells are blocked for 3.25 hours with 250 µl Blocking buffer (Thermo Cat# N502), followed by 4 washes with 300 µl wash buffer (PBS, 0.1% tween). Antibodies containing MRDs (HER-lm32(H), HER-lm32(L), and AVA-lm32(H)) and antibodies (HERCEPTIN®) were serially diluted in Blocking buffer, containing 1.94 µg/ml biotinylated Ang2 (R&D cat#BT633) and added to wells for 2 hours at RT. After washing (8×300 µl wash buffer), parallel samples received either HRP-conjugated anti-human kappa chain mAb—(Abcam, cat #ab79115-1) diluted 1:1000 in Blocking buffer or HRP-conjugated streptavidin (Thermo Scientific cat#N100) diluted 1:4000 diluted in Blocking buffer. After incubation for 1 hour at RT, wells were washed (8×300 µA wash buffer) prior to receiving 100 µl of TMB substrate (KPL Laboratories). Color development was stopped with 100 µl of $H_2SO_4$, and absorbance was read at 450 nm.

B. Results

Figure 18A:
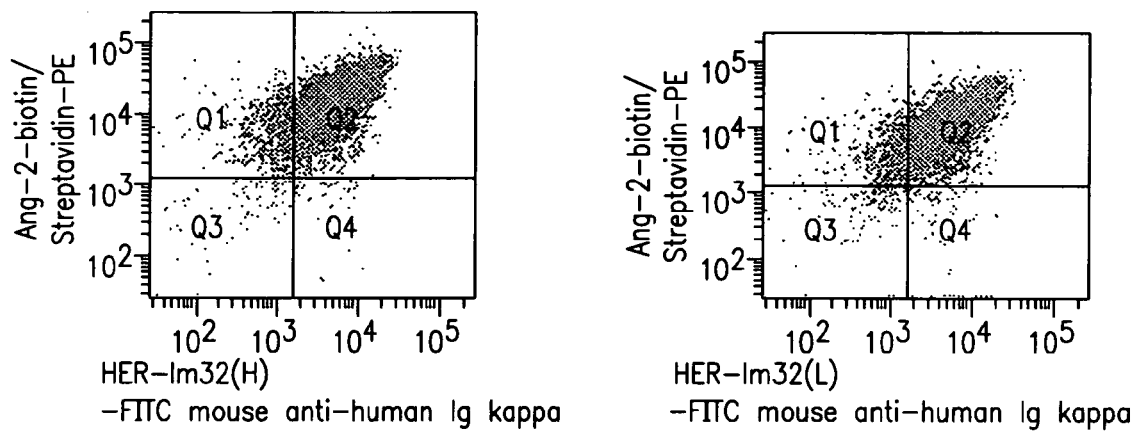
FIG. 18A depicts the results of a flow cytometry assay which demonstrates that antibody-MRDs simultaneously bind Her2 and Ang2 on BT-474 breast cancer cells.
Figure 18B:
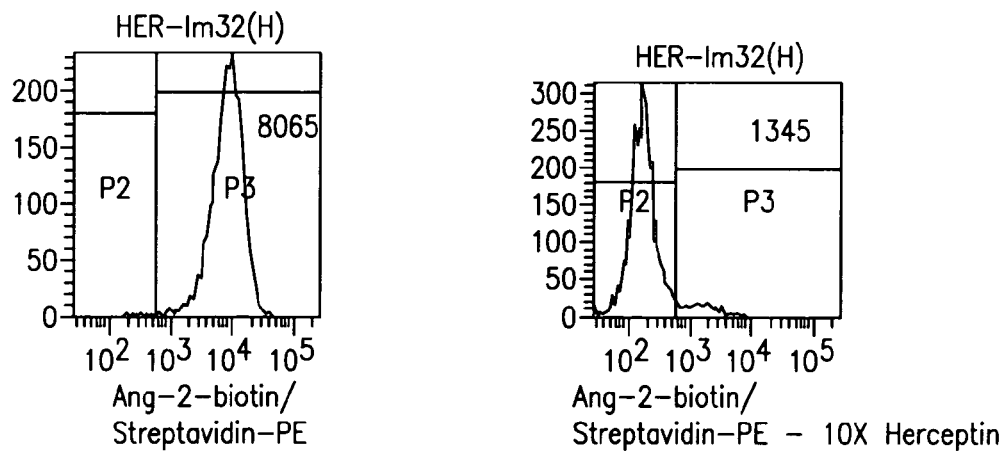
FIG. 18B depicts binding of antibody-MRDs to HER2 on BT-474 breast cancer cells.

As detected with anti-human kappa chain mAb, both a HERCEPTIN®-based antibody or HERCEPTIN®-based antibodies containing MRDs bind to Her2 Fc in the presence of Ang2 in a dose dependent manner (FIG. 18A). Only the HERCEPTIN®-based antibodies containing MRDs (HER-lm32(H) and HER-lm32(L)) exhibit simultaneous binding to Her2 Fc and Ang2, as detected by HRP-conjugated streptavidin (FIG. 18B).

Example 21

Simultaneous Binding of HER-lm32 (H) and HER-lm32 (L) to HER2 and Angiopoietin-2

The ability of HER-lm32 (H) and HER-lm32 (L) simultaneously bind to Her2 expressed on the surface of breast carcinoma cells BT-474, and to Ang2 in solution, was determined by flow cytometry. Mouse anti-human Ig-FITC was used for detection of the heavy chain of the antibodies containing MRDs, and Ang2-biotin/streptavidin-PE was used for detection of the lm32 MRD. Cells that bind Her2 and Ang2 simultaneously are expected to be detected as double positive for FITC and PE fluorescence.

One million HER2 positive breast carcinoma cells BT-474 were incubated with 1 µg HER-lm32(H) or HER-lm32(L) for 25 minutes at RT. After washing, cells were incubated with 200 ng/mL Ang2 biotin (R&D systems) for 25 minutes at RT and then with 20 µL of mouse anti-human Ig-FITC and Streptavidin-PE for 15 minutes. After washing with 2 mL buffer, cells were analyzed by flow cytometry (FACS Canto II, BD).

In order to confirm the specificity of binding of HER-lm32 (H) and HER-lm32(L) to HER2 on BT-474 cells, binding was determined in the presence of 10-fold excess of HERCEPTIN®. In these experiments, antibodies containing MRDs (1 µg) were incubated with one million BT-474 cells in the absence or presence of 10 µg HERCEPTIN® for 25 minutes at RT. Binding of antibodies containing MRDs to HER2 was determined by incubating with 200 ng/mL Ang2 biotin followed by detection with streptavidin-PE.

The data presented in FIG. 18A demonstrate that both HER-lm32(H) and HER-lm32(L), bind simultaneously to HER2 and Ang2. In both cases, the cells exhibited bright dual fluorescence in the FITC and PE fluorescence channels. The fact that HER-lm32(H) and HER-lm32(L) binding to HER2 is completely inhibited by HERCEPTIN® (FIG. 18B) indicates that the binding is specific.

Example 22

Antibody-MRDs Containing Heavy Chain Fusions Bind to Targets

To assess the ability of lm32-containing antiboides to block the interaction of Ang2 with its receptor Tie2, their effect on the binding of soluble Tie2 to plate-bound Ang2 was determined by ELISA.

Ang2 (R&D Systems, catalog#623-AN) was coated on a 96-well plate (Thermo Electron, cat#3855) at 200 ng/mL in PBS overnight at 4° C. The plate was then incubated with 100 µL of blocking solution (Thermo Scientific, cat#N502) for 1 hour at RT. After washing the plate 4 times with 0.1% Tween-20 in PBS, the plate bound Ang2 was incubated with 0.5 µg/mL soluble Tie2 (R&D Systems, cat#313-TI,) in the absence or presence of various concentrations of serially diluted antibodies containing MRDs for 1 hour at RT. After washing 4 times, 100 µL of 0.5 µg/mL anti Tie2 antibody (cat#BAM3313, R&D Systems) was added and incubated at RT for 1 hour. Tie2 binding to Ang2 was detected by incubation with 1:1000 diluted goat anti-mouse-HRP (BD Pharmingen, cat#554002) for 1 hour at RT. The plate was washed 4 times and incubated with 100 µL TMB reagent for 10 minutes at RT. After stopping the reaction with 100 µL of 0.36N $H_2SO_4$, the plate was read at 450 nm using a spectrophotometer.

Figure 19:
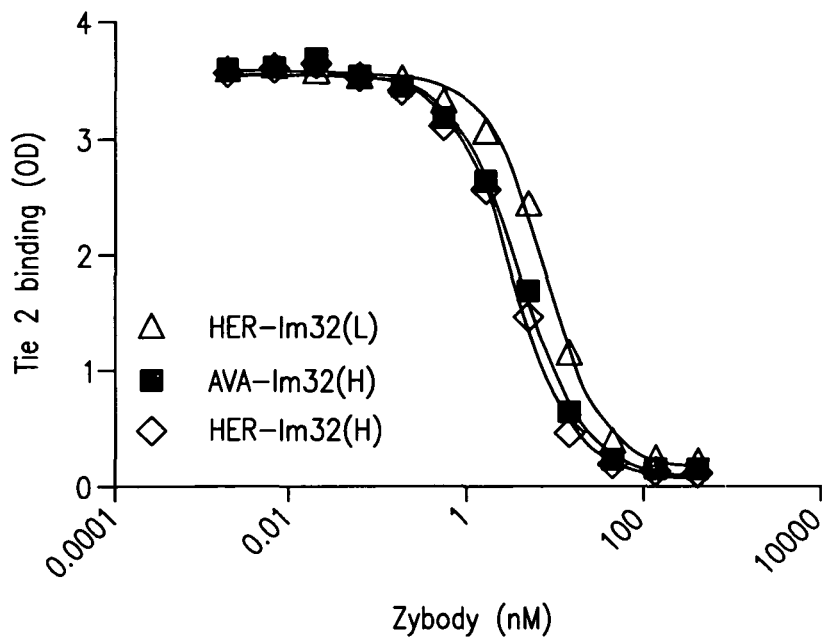
FIG. 19 depicts the results of an ELISA assay that demonstrates the inhibitory effect of antibody-MRDs on TIE-2 binding to plate immobilized Ang2.
Figure 20:
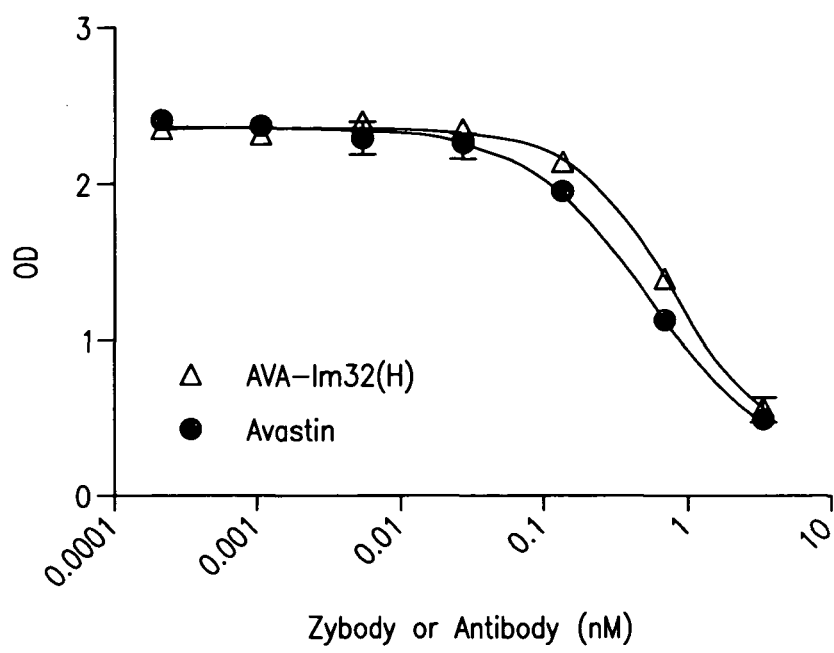
FIG. 20 depicts the results of a competitive binding assay that demonstrates the inhibition of binding of biotinylated antibody by antibody-MRD and unlabeled antibody.

As presented in FIG. 19A, HER-lm32(H), and HER-lm32 (L) inhibited Tie2 binding to plate-bound Ang2 in a dose-dependent fashion. All tested 1 m32-containing antibodies demonstrated comparable inhibitory effects with IC-50 values of 4 nM for HER-lm32 (H), and 8 nM for HER-lm32(L).

Example 23

Binding of HER-lm32(H) and HER-lm32(L) to HER2 Expressed on Breast Cancer Cells

To determine the relative binding affinity of HERCEPTIN®-based antibodies containing MRDs to cell surface HER2 compared to HERCEPTIN®, a competitive binding assay was performed with Eu-labeled HERCEPTIN®.

HERCEPTIN® was labeled with Eu3+ using a dissociation-enhanced lanthanide fluorescence immunoassay (DELFIA) Europium-labeling kit (Perkin Elmer Life Sciences, cat#1244-302) following the manufacturer's instructions. The labeling agent is the Eu-chelate of N1-(p-isothiocynateobenzyl) diethylenetriamine N1, N2, N3, N3-tetraacetic acid (DTTA). The DTTA group forms a stable complex with Eu3+, and the isothiocynate group reacts with amino groups on the protein at alkaline pH to form a stable, covalent thio-urea bond. HERCEPTIN® (0.2 mg in 200 mL sodium bicarbonate buffer pH 9.3) was labeled with 0.2 mg of labeling agent at 4° C. overnight. Eu-labeled HERCEPTIN® was purified by spin column using 50 mmol/L tris-HCl pH 7.5 and 0.9% NaCl elution buffer.

The Eu-HERCEPTIN® binding assay was performed by incubating 0.5-1 million BT-474 or SK-BR3 breast cancer cells per well in a 96-well plate with 2-5 nM Eu-HERCEPTIN® in the presence of various concentrations of unlabeled HERCEPTIN®-based antibodies containing MRDs or HERCEPTIN® for 1 hour at RT. Unbound Eu-HERCEPTIN® was removed by washing using 200 µL complete medium. Cells were then resuspended in 100 µL complete medium and 80 µL of cell suspension transferred to a 96-well isoplate. Cells were incubated with 100 µL Delfia enhancer solution at RT for 10 minutes and cell bound Eu-HERCEPTIN® was detected by Envison (Perkin Elmer).

Figure 21:
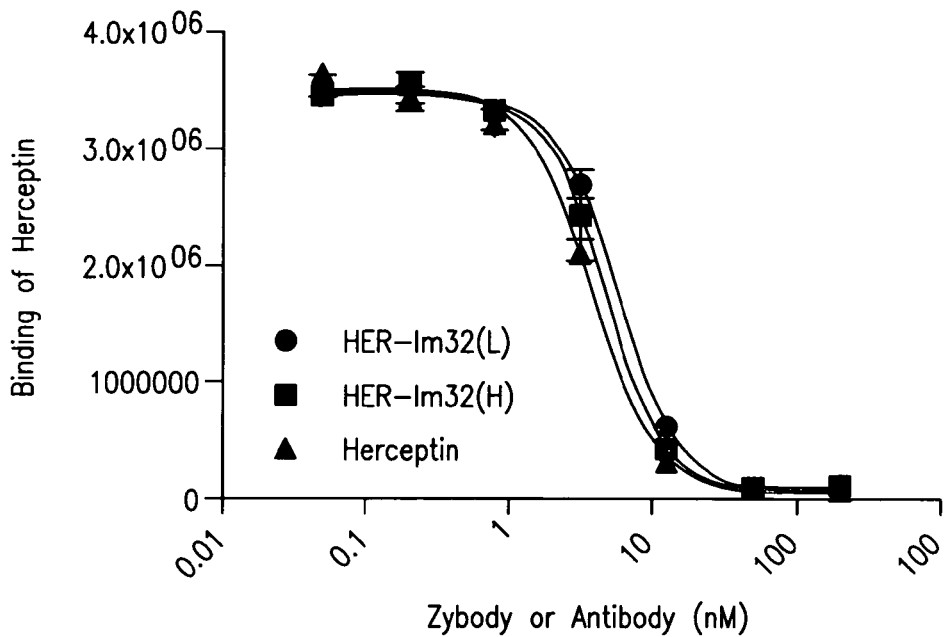
FIG. 21 depicts the results of a competitive binding assay that illustrates the inhibition of labeled antibody binding to BT-474 cells by antibody-MRDs and unlabeled antibody.

The inhibition of binding curves obtained using BT-474 cells are presented in FIG. 21. Eu-HERCEPTIN® binding to BT-474 was inhibited by HERCEPTIN® and HERCEPTIN®-based antibodies containing MRDs in a dose-dependent fashion. Comparable IC-50 values were observed: 4.7 nM for HER-lm32(H), 5.7 nM for HER-lm32(L), and 3.7 nM for unlabeled HERCEPTIN®.

Example 24

Inhibition of Breast Cancer Cells Proliferation by HERCEPTIN®-Based Antibodies Containing MRDs HERCEPTIN sensitive breast cancer cells SK-BR-3 expressing HER2neo receptor were also tested in a bioassay. SK-BR-3 cells (2000 cell/well) were plated in 96 well plates (Costar) in complete McCoy's growth medium containing 2 mM glutamine, pen/strep (Invitrogen) and 10% FBS (HyClone). The cells were cultured for 24 hours at 37° C., 5% $CO_2$, 85% humidity. On the following day, the growth medium was replaced with starvation medium (McCoy's medium containing 2 mM glutamine, pen/strep, 0.5% FBS). Nine serial dilutions (concentration range 5000-7.8 ng/ml) of HERCEPTIN® and HERCEPTIN®-based antibodies containing MRDs were prepared in complete growth medium. After 24 hours of incubation, the starvation medium was removed, and the serial dilutions of HERCEPTIN® and HERCEPTIN®-based antibodies containing MRDs were transferred to the plates in triplicates. The cells were cultured for 6 days. The proliferation was quantified using the CellTiter Glo luminescence method.

Figure 22A:
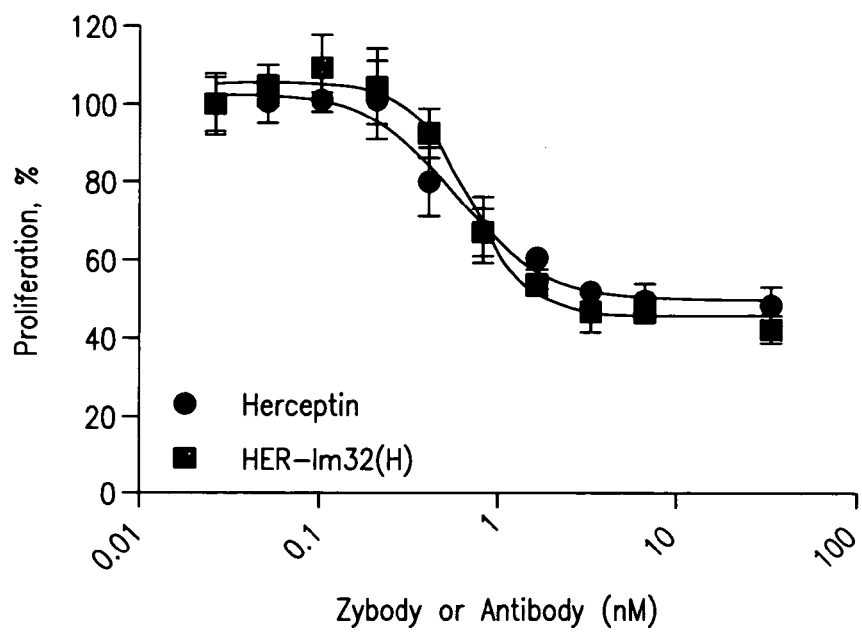
FIG. 22A depicts the fitted dose curves illustrating the inhibition of BT-474 cell proliferation by HERCEPTIN® with the lm32 MRD (SEQ ID NO:8) fused to the heavy chain and HERCEPTIN®.
Figure 22B:
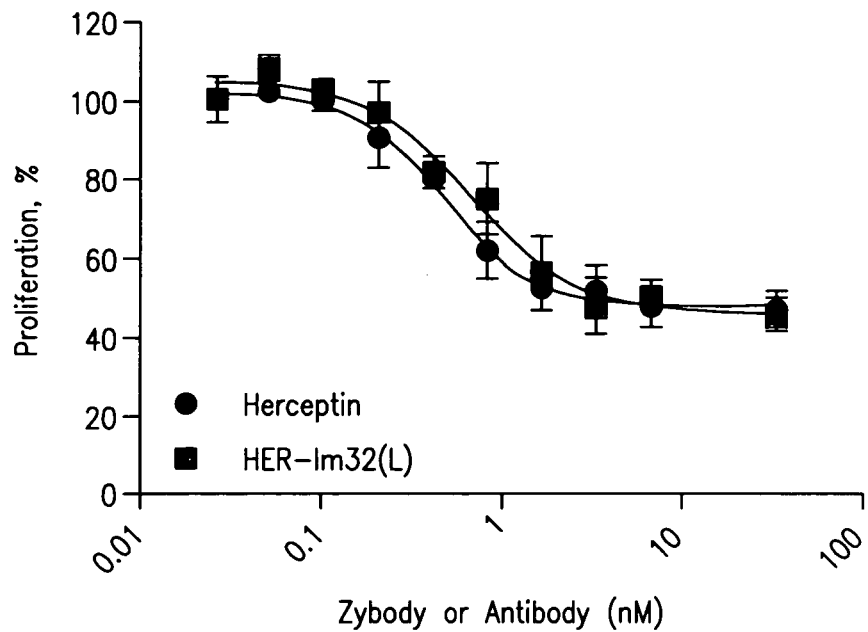
FIG. 22B depicts the fitted dose curves illustrating the inhibition of BT-474 cell proliferation by HERCEPTIN® with the lm32 MRD fused to the light chain and HERCEPTIN®.
Figure 22C:
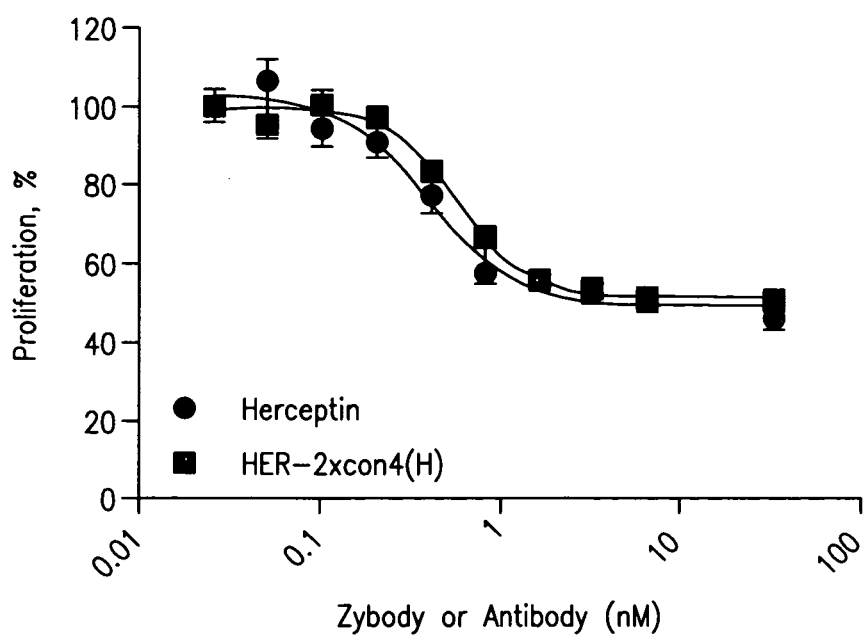
FIG. 22C depicts the fitted dose curves illustrating the inhibition of BT-474 cell proliferation by HERCEPTIN® with the 2xcon4 MRD fused to the heavy chain and HERCEPTIN®.

The IC50 values determined using a four-parameter logistic model were as follows: 0.49+/−0.17 nm for HER-lm32 (H), 0.81+/−0.19 nm for HER-lm32(L), and 0.67+/−0.15 nm for HER-con4(H). All tested HERCEPTIN®-based antibodies containing MRDs were able to inhibit the proliferation of the SK-BR-3 breast carcinoma cells with subnanomolar IC-50 values. The representative fitted dose response curves shown in FIGS. 22A-C demonstrate that HERCEPTIN®-based antibodies containing MRDs inhibit cell proliferation with similar potency to HERCEPTIN®.

Example 25

Antibody Dependent Cytotoxicity of HERCEPTIN®-Based Antibodies Containing MRDs

To assess the ability of antibodies containing MRDs to mediate ADCC in vitro, a cytotoxicity assay based on the "DELFIA EUTDA Cytotoxicity reagents AD0116" kit (PerkinElmer) was used. In this assay, the target cells were labeled with a hydrophobic fluorescence enhancing ligand (BADTA, bis(acetoxymethyl) 2,2':6',2"-terpyridine-6,6"-dicarboxylate). Upon entering the cells, BADTA is converted to a hydrophilic compound (TDA, 2,2':6',2"-terpyridine-6,6"-dicarboxylic acid) by cytoplasmic esterases mediated cleavage and no longer can cross the membrane. After cell lysis, TDA is released into a medium containing Eu3+ solution to form a fluorescent chelate (EuTDA). The fluorescence intensity is directly proportional to the number of lysed cells.

HERCEPTIN® and HERCEPTIN®-based antibodies containing MRDs can mediate ADCC on Her2 positive breast cancer cells by binding to the HER2 receptor on the surface of the target cells and activating the effector cells present in human PBMCs by interacting with their FcγRIII receptors. A HER2 positive human breast cancer cell line SK-BR-3 was used as a target cell line in the ADCC assay to demonstrate this.

SK-BR-3 cells were detached with 0.05% trypsin-versene and resuspended at $1 \times 10^6$ cells/mL in RPMI1640 medium containing 2 mM glutamine, pen/strep and 10% FBS (complete growth medium). $2 \times 10^6$ cells in 2 mL of media were transferred into 15 mL tube and 10 µl of BADTA reagent was added. The cell suspension was mixed gently and placed in the incubator at 37° C., 5% $CO_2$ and 85% humidity for 15 minutes. Seven 10× serial dilutions starting with 5 µg/mL of HERCEPTIN® or HERCEPTIN®-based antibodies containing MRDs were prepared during cell labeling.

After incubation with BADTA, cells were washed 4 times in complete growth medium containing 2.5 mM Probenecid. Between washes, cells were spun down by centrifugation at 1000 rpm for 3 minutes. After the last wash, labeled SK-BR-3 cells were resuspended in 10 mL complete growth medium and 50 µl of cells were added to each well of 96 well plate, except background wells. 50 µl of serial dilutions of HERCEPTIN® or HERCEPTIN®-based antibodies containing MRDs were added to the designated wells. The plates were transferred to the incubator at 37° C., 5% $CO_2$ and 85% humidity for 30 minutes.

PBMCs that were purified from human peripheral blood one day prior the ADCC assay, were washed once in RPMI1640 with 2 mM glutamine, pen/strep, 10% FBS. 10 mL of the PBMCs suspension with $2.5 \times 10^6$ cells/mL was prepared. 100 µl of PBMC suspension was transferred into wells containing target cells and HERCEPTIN® or HERCEPTIN®-based antibodies containing MRDs in triplicate. The following controls were placed in designated wells: Spontaneous release (target cells without effector cells), Maximum release (lysed target cells) and Background (media without cells). The plates were incubated for 2.5 hours an incubator with 37° C., 5% $CO_2$ and 85% humidity.

After incubation 20 µl of the supernatant was transferred to another plate and 200 µl of Europium solution was added. The plates were incubated on a plate shaker at RT for 15 minutes. The time resolved fluorescence was measured using PerkinElmer EnVision 2104 Multilabel Reader.

The following formula was used to calculate percentage of Specific release:

$$\frac{\text{Experimental release(counts)} - \text{Spontaneous release (counts)} \times 100}{\text{Maximum release(counts)} - \text{Spontaneous release(counts)}}$$

Figure 23A:
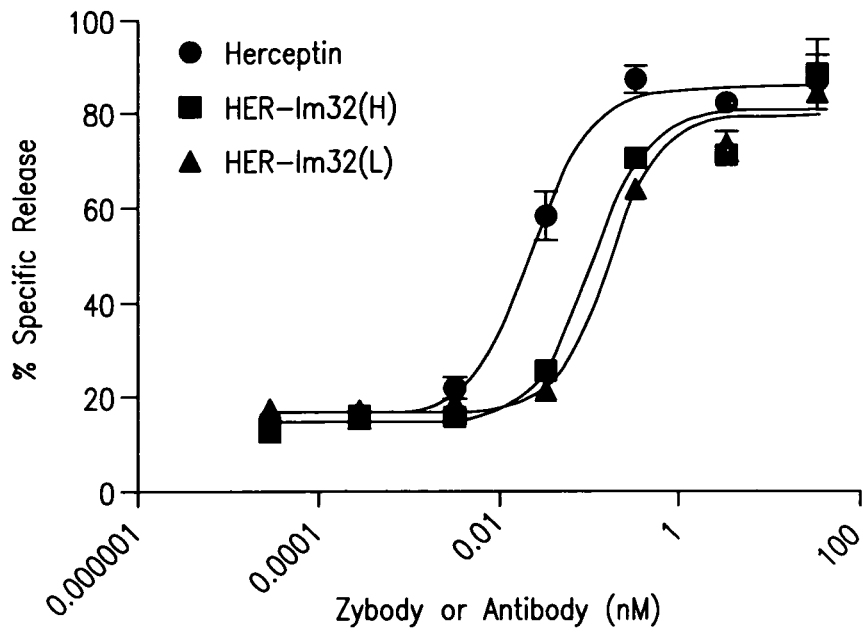
FIG. 23A depicts the results of a cytotoxicity assay illustrating ADCC-mediated killing of BT-474 cells by HERCEPTIN® with the lm32 MRD fused to the heavy chain, HERCEPTIN® with the lm32 MRD fused to the light chain, and HERCEPTIN®
Figure 23B:
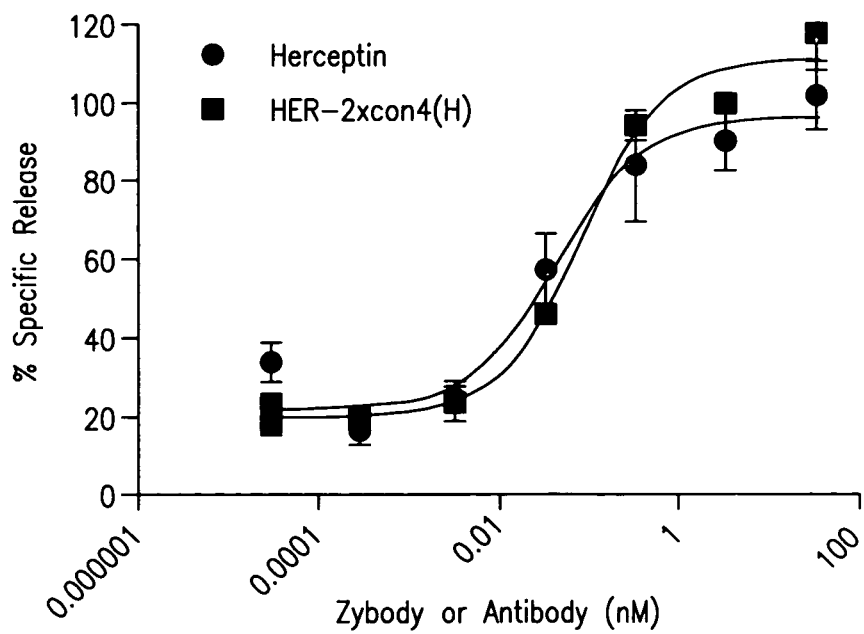
FIG. 23B depicts the results of a cytotoxicity assay illustrating ADCC-mediated killing of BT-474 cells by HERCEPTIN® with the 2xcon4 MRD fused to the heavy chain, and HERCEPTIN®.

The IC50 values calculated by a four-parameter logistic model were as follows: 0.213+/−0.077 nM for HER-lm32 (H), 0.204+/−0.036 nM for HER-lm32(L), and 0.067+/−0.015 nM for HER-con4(H). All tested antibodies containing MRDs demonstrated robust ADCC activity with subnanomolar IC-50 values. The representative fitted dose response curves shown in FIGS. 23A and 23B demonstrate that antibodies containing MRDs are able to mediate cell dependent cytotoxicity with comparable potency to HERCEPTIN®.

Example 26

MRD-Containing Antibodies Inhibit Tumor Proliferation In Vivo

Figure 24:
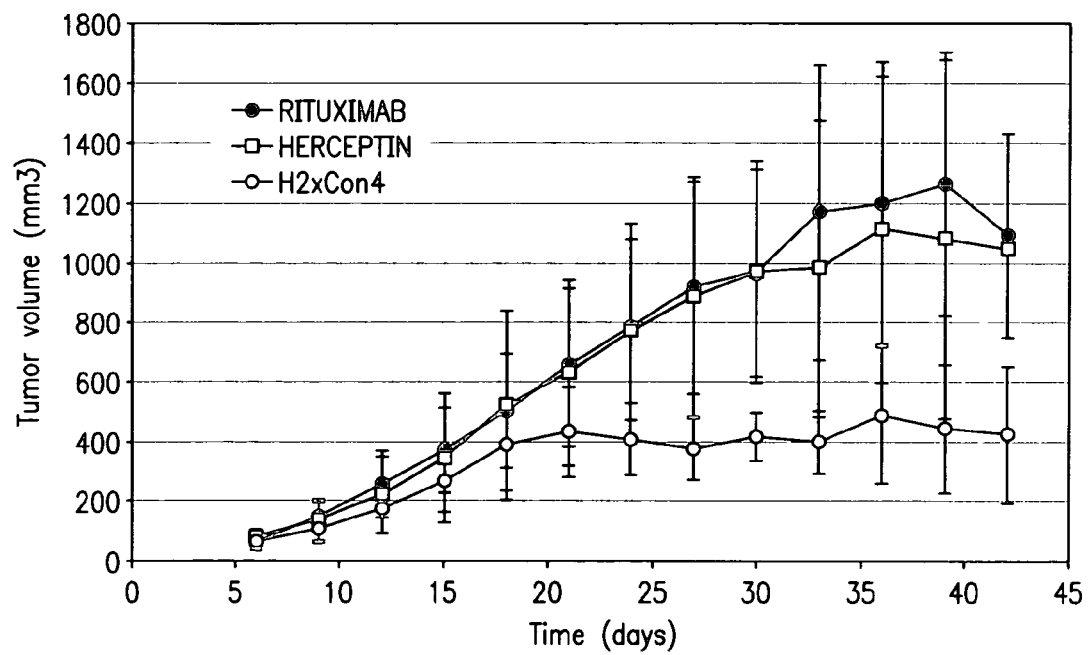
FIG. 24 depicts the effect of RITUXIMAB®, HERCEPTIN®, and an MRD-containing antibody on tumor volume in vivo.

In order to determine the effectiveness of MRD-containing antibodies in vivo, their efficacy in a mouse Colo5 tumor model was assessed. In these experiments, tumors were implanted into the right flank of six-week old femal athymic nude mice by injecting $5 \times 10^6$ Colo205 cells suspended in 100 µL PBS. Three groups of eight animals each received intraperitoneal injections of 5 mg/kg of antibody (Herceptin) or an MRD-containing antibody (HER-2xCon4; "H2xCon4") in 100 µL PBS every third day starting at day 6 after tumor implantation. The results, shown in FIG. 24, demonstrate that the MRD-containing antibody was more efficient at inhibiting tumor growth than Herceptin®.

Example 27

In Vivo Assays to Evaluate MRD-Containing Antibodies

In order to determine the efficacy of MRD-containing antibodies in vivo, animal models are treated with an antibody and an MRD-containing antibody and the results are compared.

MRD-containing anti-HER2 antibodies are tested in the following in vivo model. NIH 3T3 cells transfected with a HER2 expression plasmid are injected into nu/nu athymic mice subcutaneously at a dose of $10^6$ cells in 0.1 ml of phophate-buffered saline as described in U.S. Pat. No. 6,399,063, which is herein incorporated by reference in its entirety. On days, 0, 1, 5, and every 4 days thereafter 100 µg of a HER2 antibody, an ang2-containing HER2 antibody, an igf1r-containing HER2 antibody and an ang2-igf1r-containing HER2 antibody are injected intraperitoneally. Tumor occurrence and size are monitored for one month. Increases in efficacy of MRD-containing antibodies compared to antibodies are observed.

MRD-containing anti-VEGF antibodies are tested in the following in vivo model. RIP-TβAg mice are provided with high-sugar chow and 5% sugar water as described in U.S. Published Application No. 2008/0248033, which is herein incorporated by reference in its entirety. At 9-9.5 or 11-12 weeks of age, the mice are treated twice-weekly with intraperitoneal injections of 5 mg/kg of an anti-VEGF antibody, ang2-containing VEGF antibody, ifg1r-containing VEGF antibody or ang2- and igf1r-containing antibody. The 9-9.5 week mice are treating for 14 days and then examined. The 11-12 week mice are examined after 7, 14, and 21 days of treatment. The pancrease and spleen of the mice are removed and analyzed. Tumor number is determined by dissecting out each sperical tumor and counting. Tumor burden is determined by calculating the sum of the volume of all tumors within the pancreas of a mouse. The effect on angiogogenesis is determined by calculating the mean number of angiogenic islets observed. Increases in efficacy of MRD-containing antibodies compared to antibodies are observed.

Although the invention has been described with reference to the above examples, it will be understood that modifications and variations are encompassed within the spirit and scope of the invention. Accordingly, the invention is limited only by the following claims All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

What is claimed is:

1. A complex comprising an antibody and at least one modular recognition domain (MRD), wherein the MRD competitively inhibits binding of angiopoietin-2 (Ang2) to a polypeptide consisting of the amino acid sequence of SEQ ID NO:8 or SEQ ID NO: 21, wherein the antibody is (a) murine, (b) chimeric, (c) humanized, or (d) human, and wherein the antibody binds to a cell surface tumor antigen.

2. The complex of claim 1, wherein the antibody is multi-specific.

3. The complex of claim 1, wherein the antibody is an IgG.

4. The complex of claim 1, wherein the antibody binds to a target selected from the group consisting of an integrin, insulin-like growth factor-I receptor (IGF-IR), a CD20, epidermal growth factor receptor (EGFR), ErbB2 receptor, ErbB3 receptor, and tumor associated surface antigen epithelial cell adhesion molecule (Ep-CAM).

5. The complex of claim 1, wherein the antibody binds to the same epitope as trastuzumab, cetuximab, or panitumumab.

6. The complex of claim 1, wherein the MRD is located on a terminus selected from the group consisting of (a) the N-terminus of the antibody heavy chain, (b) the N-terminus of the antibody light chain, (c) the C-terminus of the antibody heavy chain, and (d) the C-terminus of the antibody light chain.

7. The complex of claim 6, wherein a first MRD is located on (c) the C-terminus of the antibody heavy chain and a second MRD is located on (d) the C-terminus of the antibody light chain.

8. The complex of claim 1, wherein the antibody and the MRD are operably linked through a linker peptide.

9. The complex of claim 8, wherein the linker comprises a sequence selected from the group consisting of: SEQ ID NO:1, SEQ ID NO:2, and SEQ ID NO:19.

10. The complex of claim 1, wherein the antibody and the at least one MRD bind to their targets simultaneously.

11. The complex of claim 1, wherein the antibody comprises at least two MRDs.

12. The complex of claim 11, wherein the two MRDs are homo-multimeric.

13. The complex of claim 11, wherein the two MRDs are hetero-multimeric.

14. The complex of claim 13, wherein the hetero-multimeric MRDs bind to different targets.

15. The complex of claim 11, wherein the two MRDs are located on the same antibody terminus or on different antibody termini.

16. The complex of claim 11, wherein the complex is capable of binding to the antibody target and two MRD targets simultaneously.

17. The complex of claim 1, wherein the antibody comprises at least three MRDs.

18. The complex of claim 17, wherein the antibody and the three MRDs bind to their targets simultaneously.

19. The complex of claim 1, wherein the antibody comprises at least four MRDs.

20. The complex of claim 19, wherein the antibody and the four MRDs bind to their targets simultaneously.

21. The complex of claim 1, wherein the complex has ADCC activity.

22. A fusion polypeptide comprising an antibody heavy chain and an MRD, wherein the MRD competitively inhibits binding of Ang2 to a polypeptide consisting of the amino acid sequence of SEQ ID NO:8 or SEQ ID NO: 21, wherein the antibody is (a) murine, (b) chimeric, (c) humanized, or (d) human, and wherein the antibody binds to a cell surface tumor antigen.

23. A fusion polypeptide comprising an antibody light chain and an MRD, wherein the MRD competitively inhibits binding of Ang2 to a polypeptide consisting of the amino acid sequence of SEQ ID NO:8 or SEQ ID NO: 21, wherein the antibody is (a) murine, (b) chimeric, (c) humanized, or (d) human, and wherein the antibody can bind to a cell surface tumor antigen.

24. A pharmaceutical composition comprising the complex of claim 1.

25. A method for inhibiting the growth of a cell comprising contacting the cell with the complex of claim 1.

26. A method for inhibiting angiogenesis in a patient comprising administering to said patient a therapeutically effective amount of the complex of claim 1.

27. The complex of claim 1, wherein the complex further comprises a MRD consisting of the animo acid sequence of SEQ ID NO: 7-11, 21, 23, 24, 26, 27, 29, 30, 32, 33, or 34.

28. The complex of claim 1, wherein the antibody binds to the same epitope as trastuzumab.

29. The complex of claim 27, wherein the antibody binds to the same epitope as trastuzumab.

30. The complex of claim 29, wherein the antibody is trastuzumab.

31. The complex of claim 3, wherein the IgG is an IgG1.

32. A complex comprising an antibody and at least one modular recognition domain (MRD), wherein the MRD binds to Ang2 and consists of the amino acid sequence of SEQ ID NO: 7-12, 21, 23, 24, 26, 27, 29, 30, or 32-34, and wherein the antibody binds to the same epitope as trastuzumab.

* * * * *